United States Patent [19]
Dorner et al.

[11] Patent Number: 5,445,953
[45] Date of Patent: Aug. 29, 1995

[54] DIRECT MOLECULAR CLONING OF A MODIFIED POXVIRUS GENOME

[75] Inventors: Friedrich Dorner, Vienna; Friedrich Scheiflinger, Orth/Donau; Falko G. Falkner, Mannsdorf, all of Austria

[73] Assignee: Immuno Aktiengesellschaft, Vienna, Austria

[21] Appl. No.: 750,080
[22] Filed: Aug. 26, 1991
[51] Int. Cl.6 .................. C12N 15/09; C12N 7/01; C12N 15/64; C12N 15/86
[52] U.S. Cl. .................. 435/172.3; 435/235.1; 435/320.1; 935/32; 935/57
[58] Field of Search .............. 435/172.3, 172.1, 235.1, 435/320.1; 935/32, 57

[56] References Cited

PUBLICATIONS

Fenner, F. et al. 1960 *Virology* vol. 11 pp. 185–201.
Boyle, D. B. 1989 *Research in Virology* vol. 140 pp. 483–491.
Bostock, C. J. 1990, *Vet. Microbiol.* vol. 23 pp. 55–71 (Abstract only).
Burke, D. T. 1990, *Genet. Anal. Tech. Appl.* vol. 7 pp. 54–59.
Sternberg, N. L. 1990, *Genet. Anal. Tech. Appl.* vol. 7, pp. 126–132.
Rixon, F. J. et al. 1990, *J. Gen. Virol.* vol. 71 pp. 2931–2939.
Langridge, W. H. R. 1983, *J. Invert. Pathol.* vol. 42 pp. 77–82.
Scheiflinger, F. et al. 1992, *Proc. Natl. Acad. Sci. USA* vol. 89 pp. 9977–9981.
Merchlinsky, M. et al. 1992, *Virology* vol. 190 pp. 522–526.
Gritz et al. "Generation of Hybrid Genes and Proteins by Vaccinia Virus–Mediated Recombination: Application to Human Immunodeficiency Virus Type 1 env", *J. of Virology*, Dec. 1990; vol. 64: 5948–5957.
Hruby et al. "Assembly and Analysis of a Functional Vaccinia Virus amplicon containing the C-Repeat Region from the M Protein of Streptococcus Pyogenes", *Proc. Natl. Acad. Sci. USA;* Apr. 1991; vol. 88: 3190–3194.
Harley et al. "Vaccinia Virus Expression and Sequence of an Avian Influenza Nucleoprotein Gene: Potential Use in a Diagnosis", *Arch Virol.,* (1990), 113, 13–141.
Sam & Dumbell "Expression of Poxvirus DNA In Coinfected Cells and Marker Rescue Of Thermosensitive Mutants . . ." *Ann. Virol.* (*Inst. Pasteur*), 132E, 135–150 (1981).
Panicali et al. "Construction of Poxviruses as Cloning Vectors: Insertion of the Thymidine Kinase Gene From Herpes Simplex Virus Into the DNA of Infectious Vaccinia Virus", *Proc. Natl. Acad. Sci. USA,* 79, 4927–4931 (1982).
Fenner et al. "Vaccinia Virus as a Vector for Vacine Antigens", *The Poxviruses* (Acad. Press), 12: 355–356 (1989).
Mackett et al. "Vaccinia Virus Expression Vectors", *J. Gen. Virol.* 67: 2067–2082 (1986).
Miner et al. "Vaccinia Virus: A Versatile Tool for Molecular Biologists", *TIBTECH,* 8: 20–25 (1990).
Moss et al. "Vaccinia Virus Expression Vectors", *Rev. Immunol.,* 5: 305–324 (1987).

Primary Examiner—Mary E. Mosher
Attorney, Agent, or Firm—Foley & Lardner

[57] ABSTRACT

A method is disclosed for producing a modified eukaryotic cytoplasmic DNA virus by direct molecular cloning of a modified DNA molecule comprising a modified cytoplasmic DNA virus genome. The inventive method comprises the steps of (I) modifying under extracellular conditions a DNA molecule comprising a first cytoplasmic DNA virus genome to produce a modified DNA molecule comprising the modified cytoplasmic DNA virus genome; (II) introducing the modified DNA molecule into a first most cell which packages the modified DNA molecule into infectious virions; and (III) recovering from the host cell virions comprised of the modified vital genome. The host cell is infected with a helper virus which is expressed to package the modified viral genome into infectious virions. Examples of packaging a modified poxvirus genome by a helper poxvirus of the same or different genus are described. Also disclosed are novel poxvirus vectors for direct molecular cloning of open reading frames into a restriction enzyme cleavage site that is unique in the vector. In one model poxvirus vector, the open reading frame is transcribed by a promoter located in the vector DNA upstream of a multiple cloning site comprised of several unique cleavage sites.

26 Claims, 34 Drawing Sheets

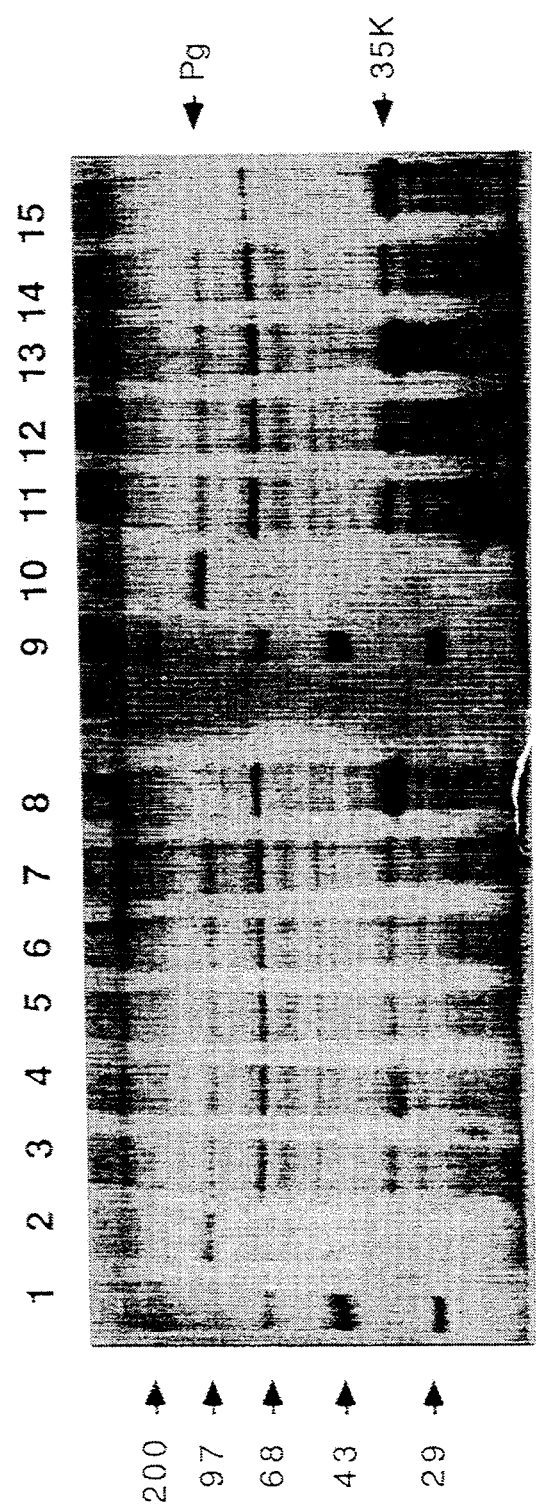
FIG. 1.1

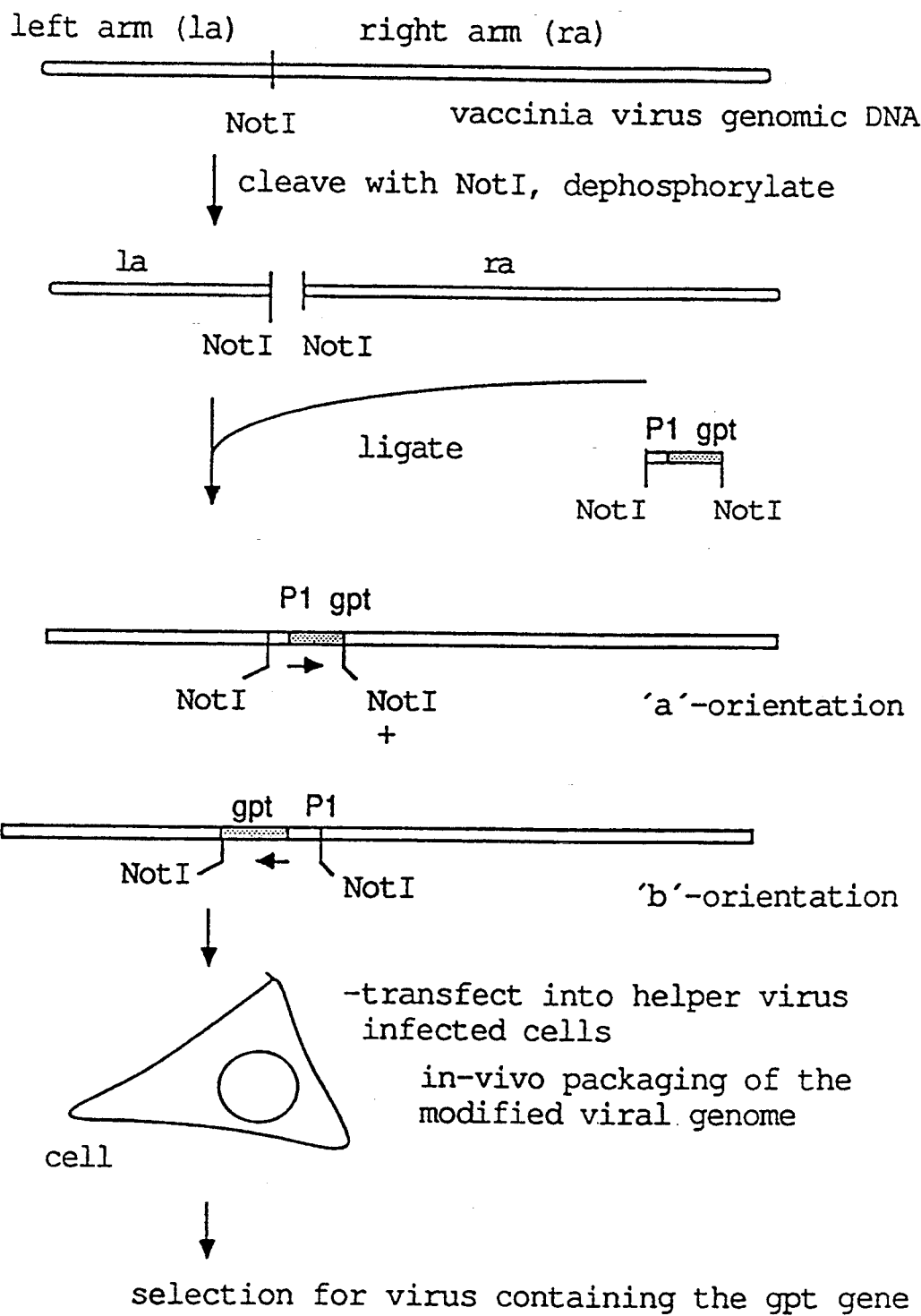
FIG. 1.2

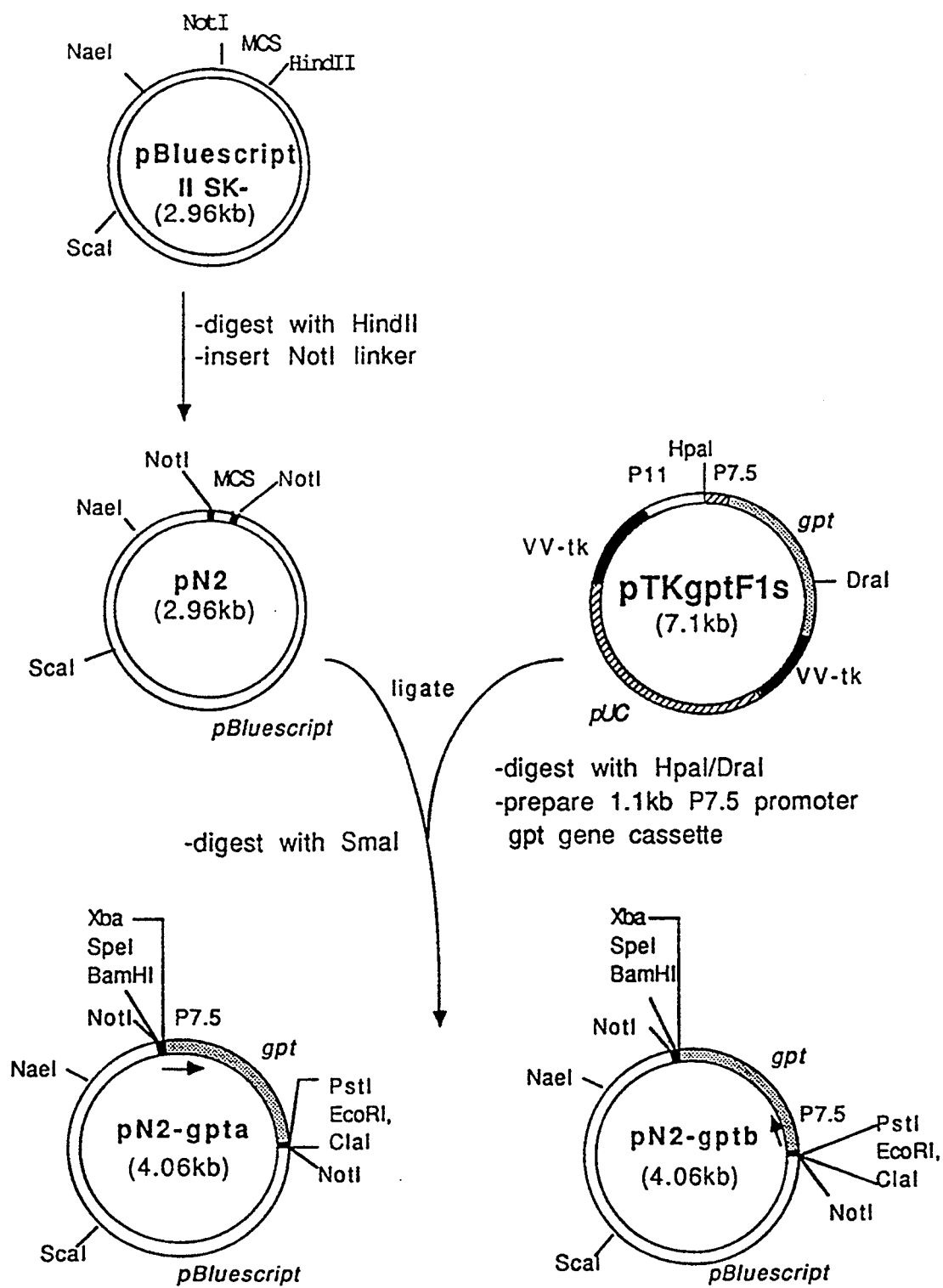
FIG. 1.3
Construction of the plasmids pN2-gpta and pN2-gptb

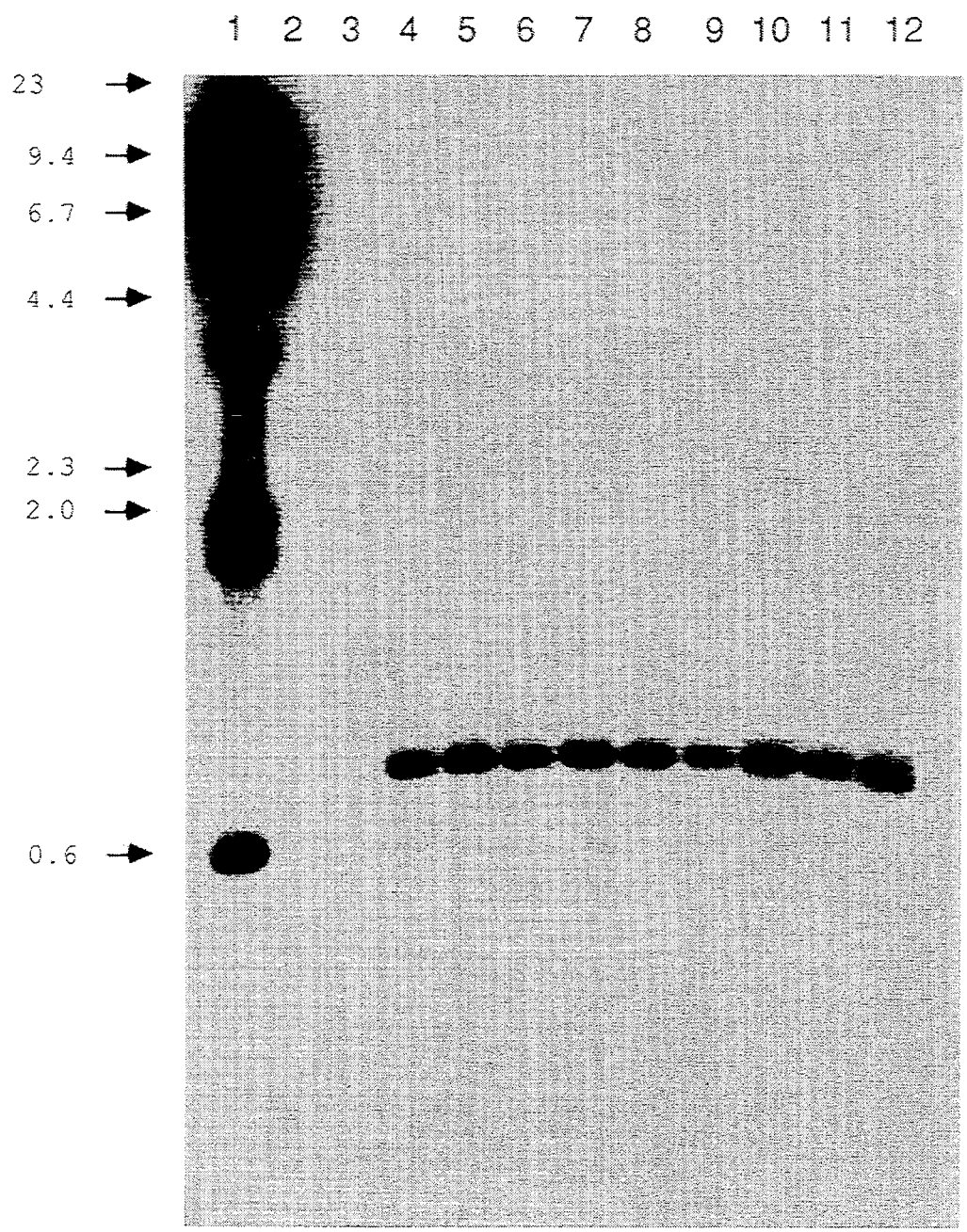

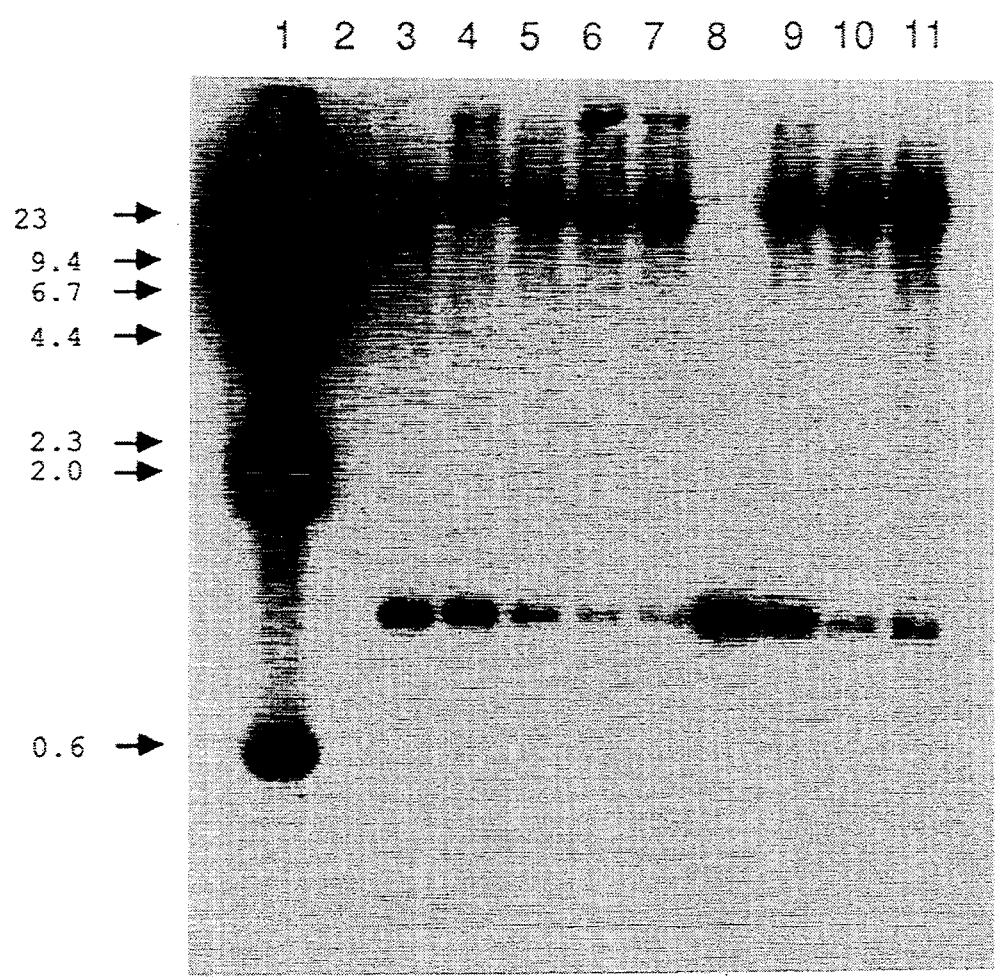
FIG. 1.5

FIG. 1.6
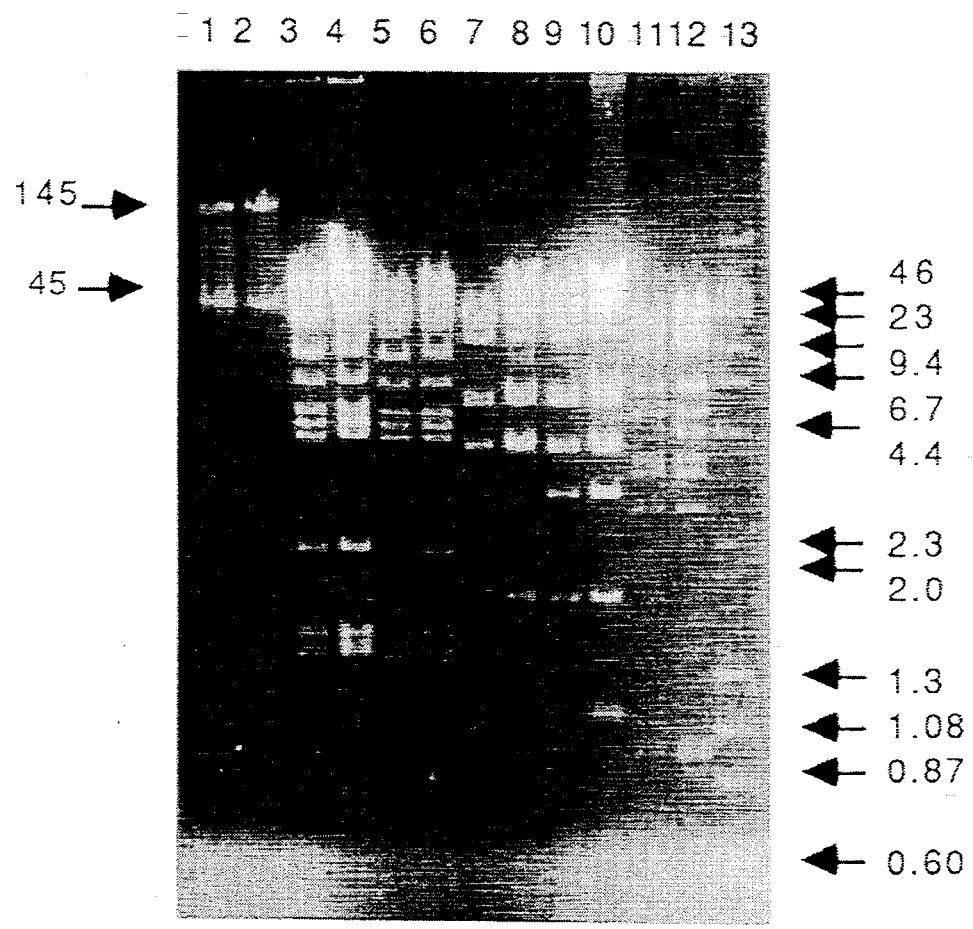

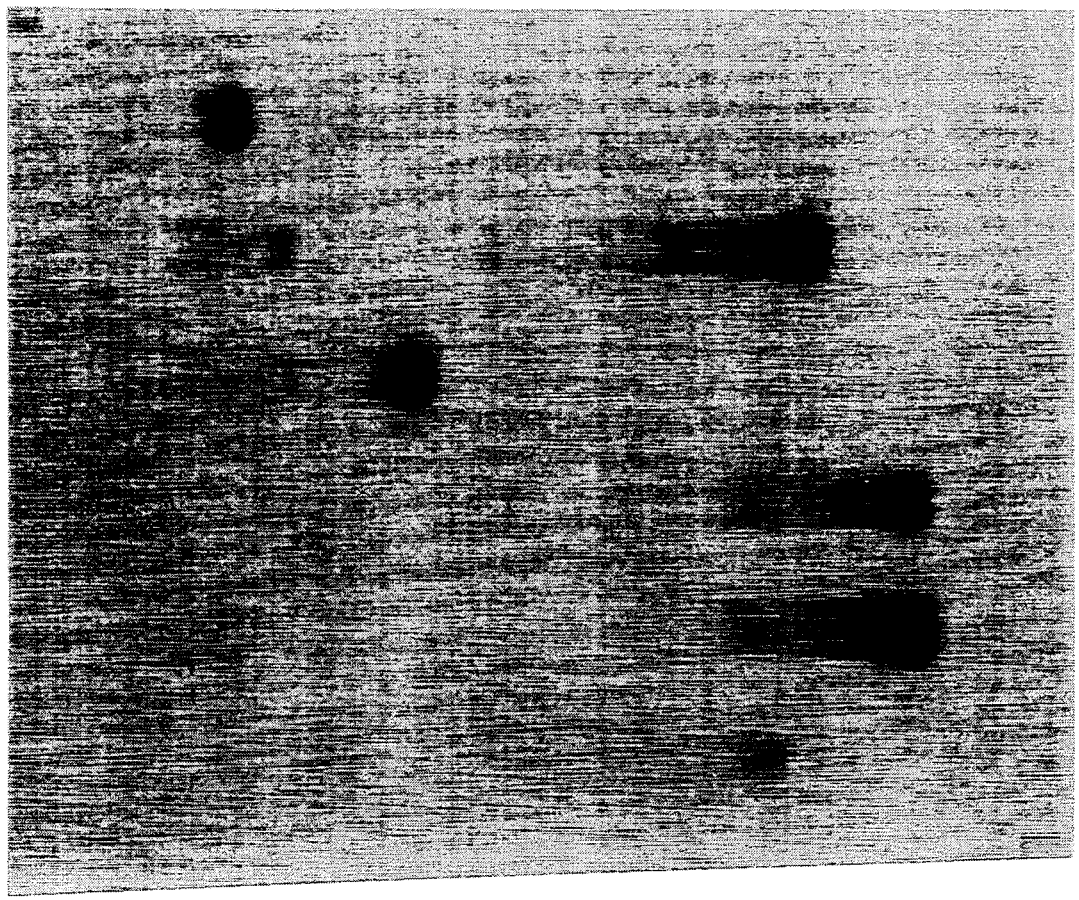
FIG. 1.7

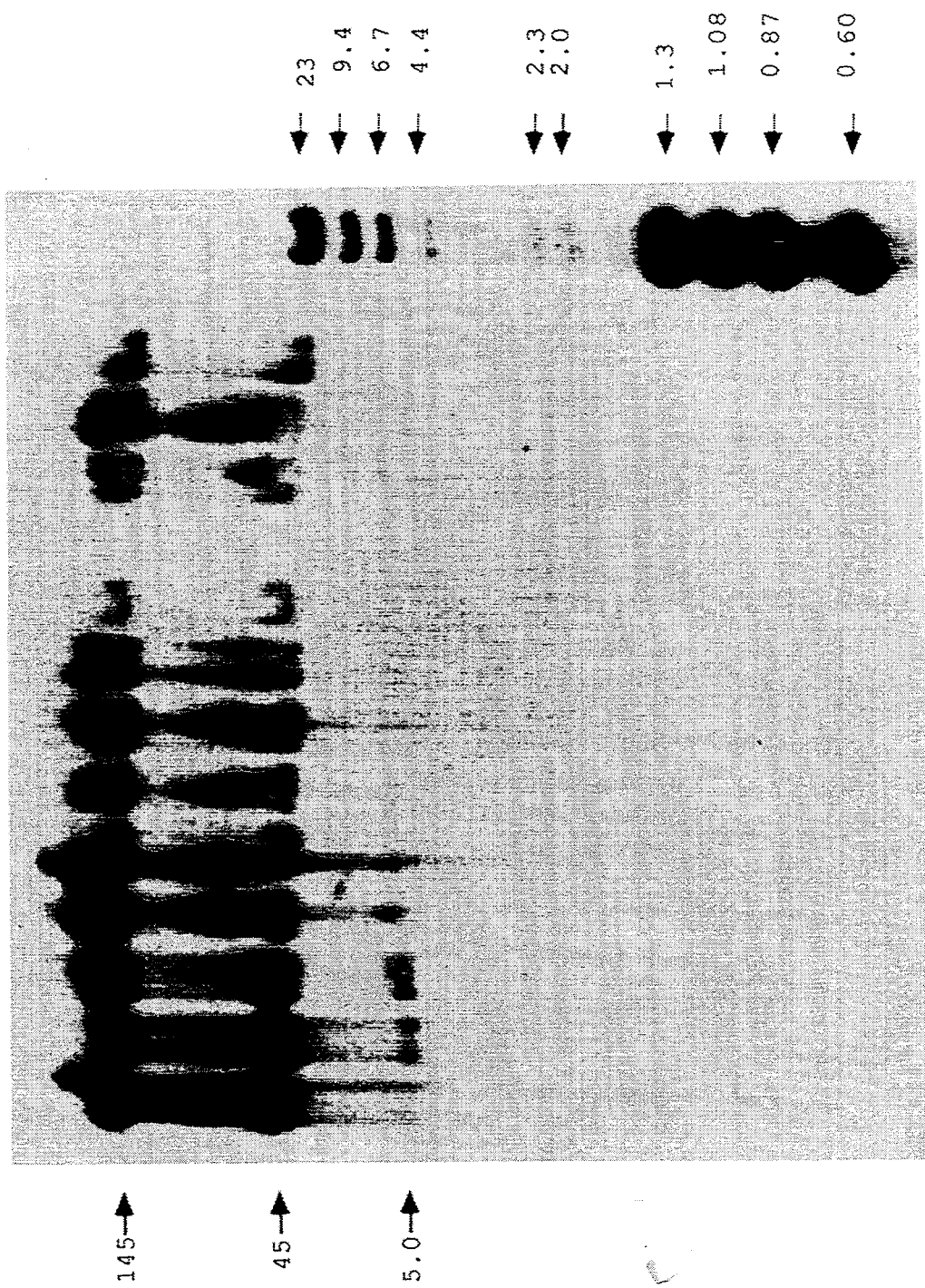
FIG. 1.8

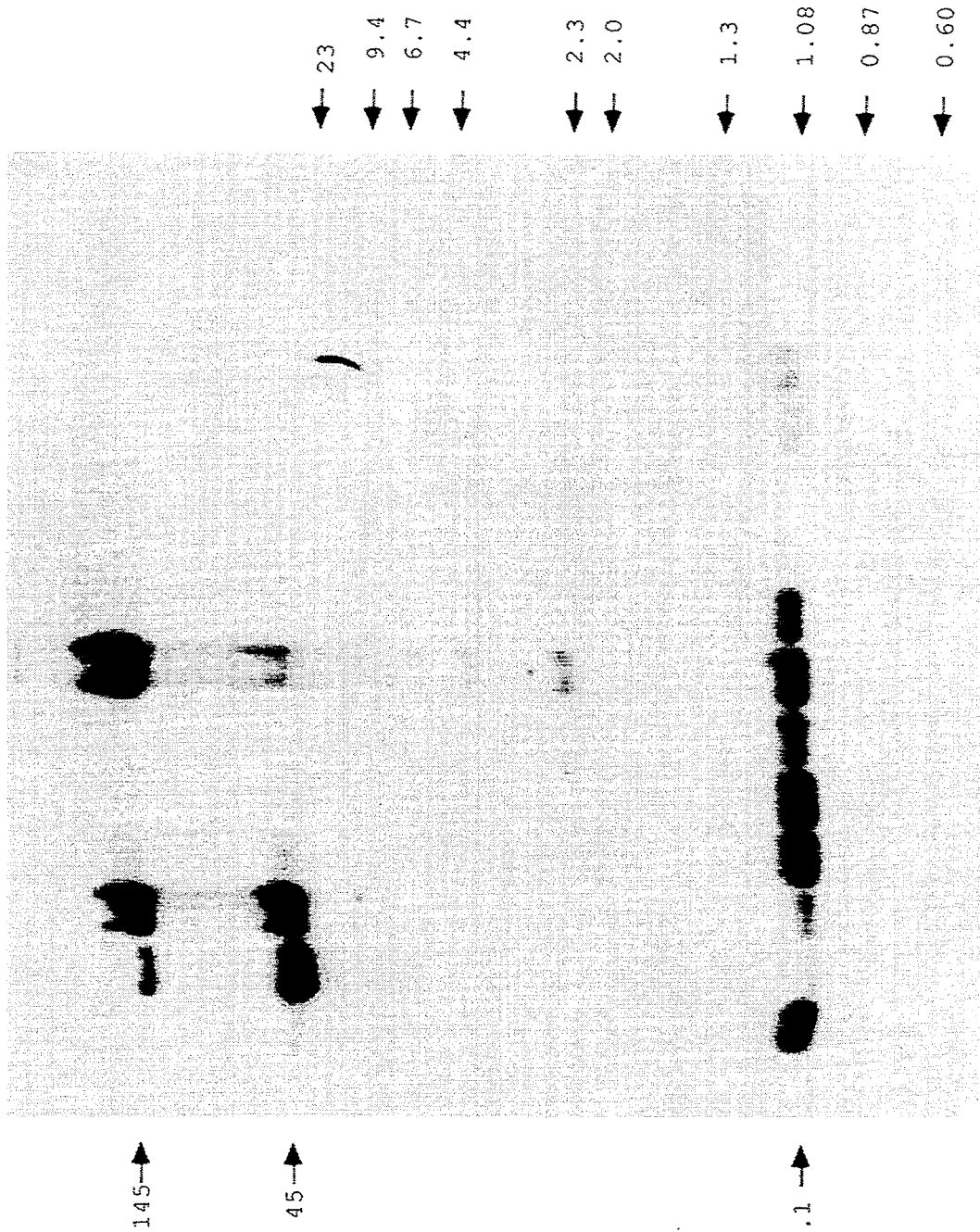
FIG. 1.9

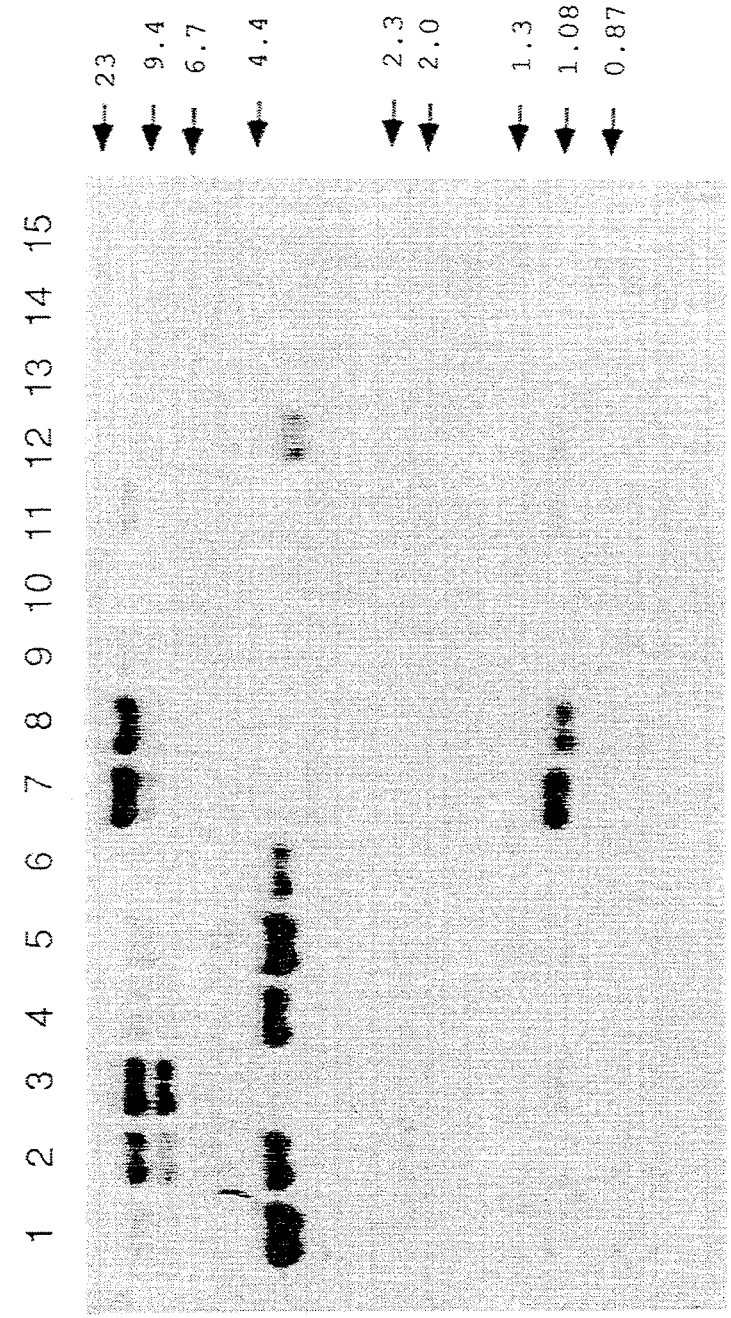
FIG. 1.10

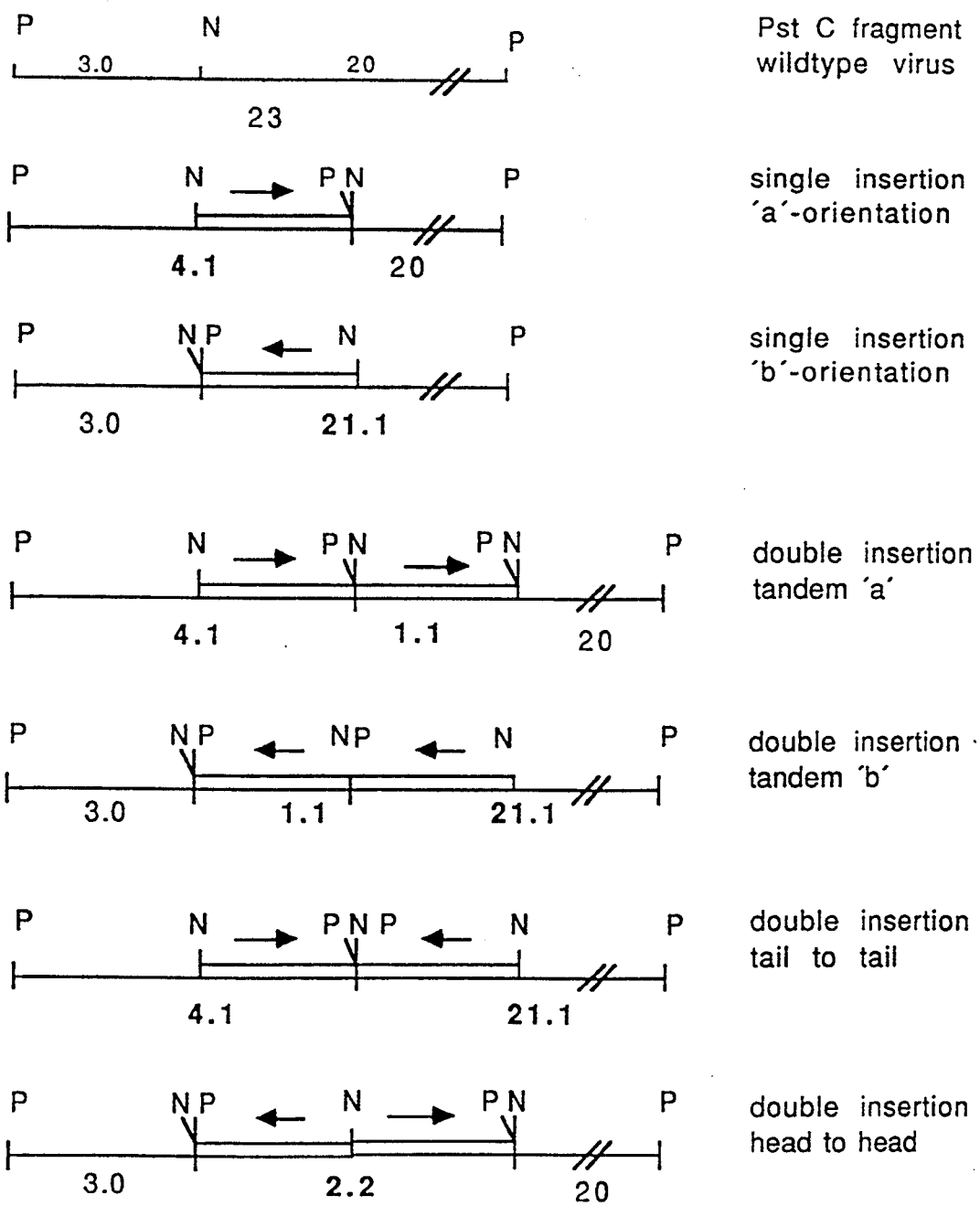
FIG. 1.11

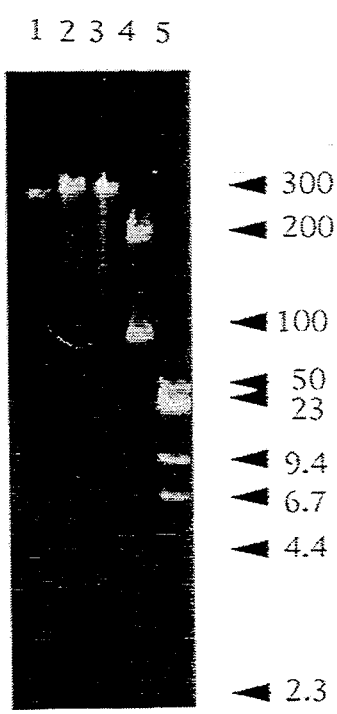
FIG. 2.1

FIG. 2.2
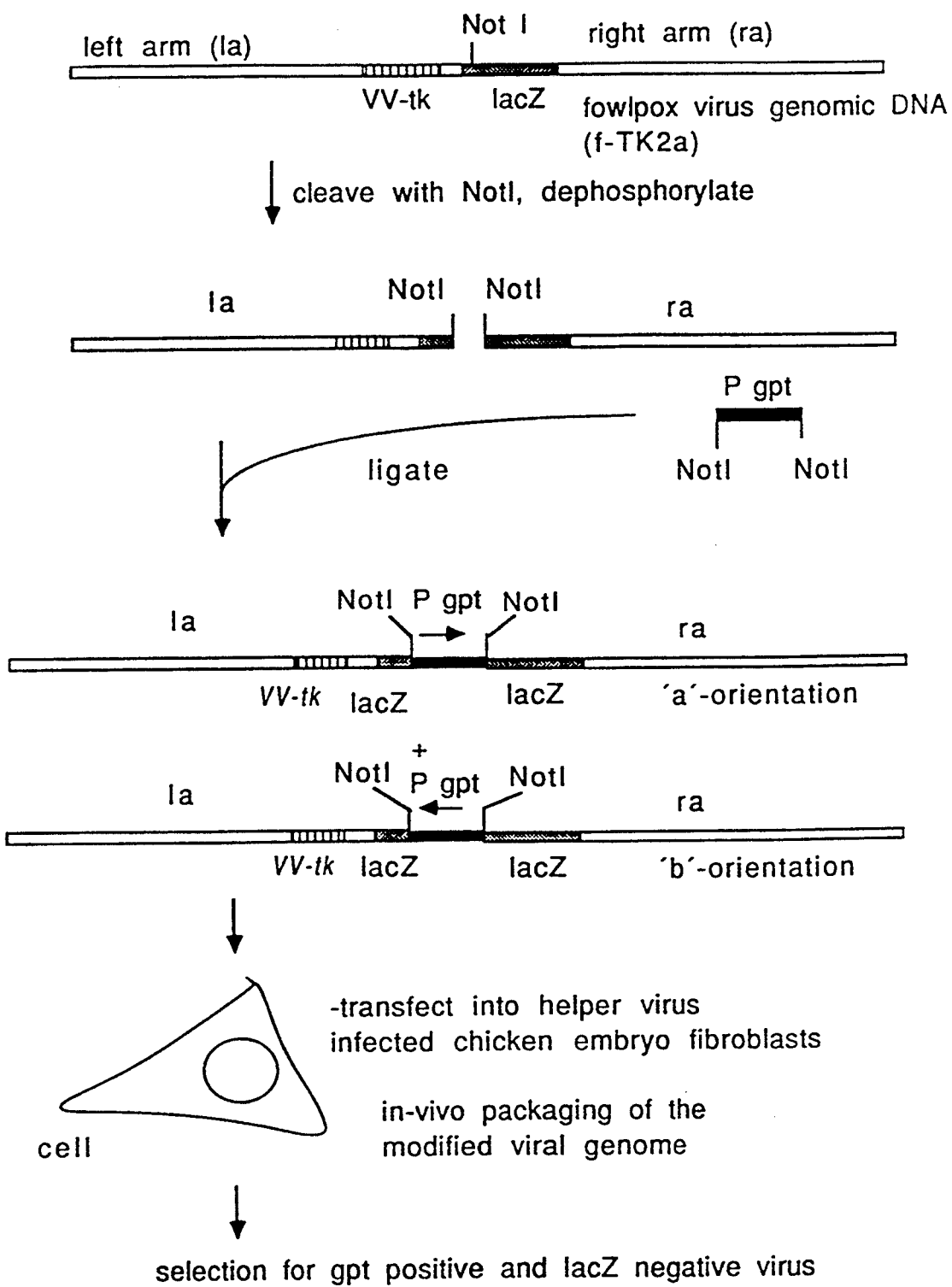

FIG. 3.1
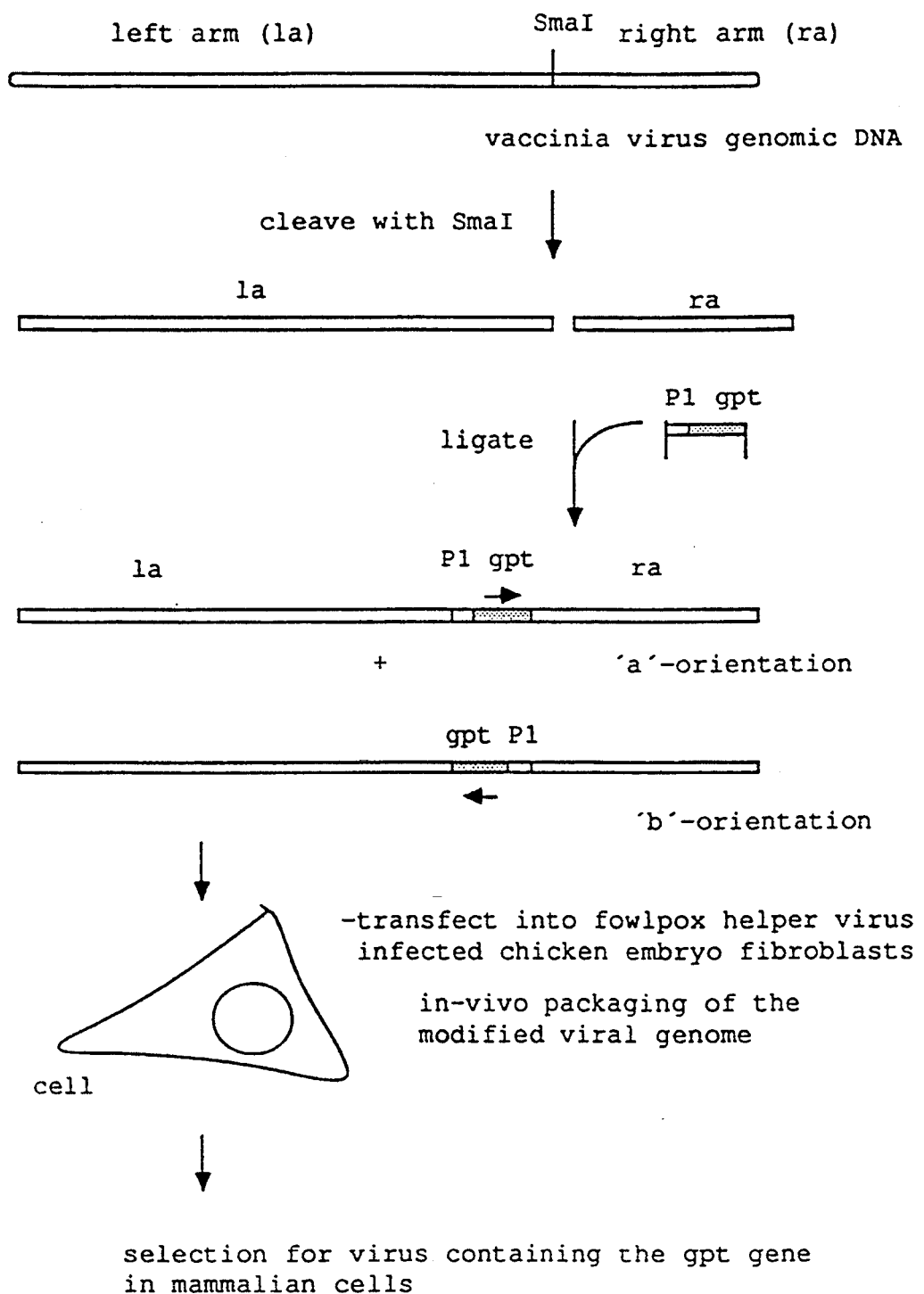

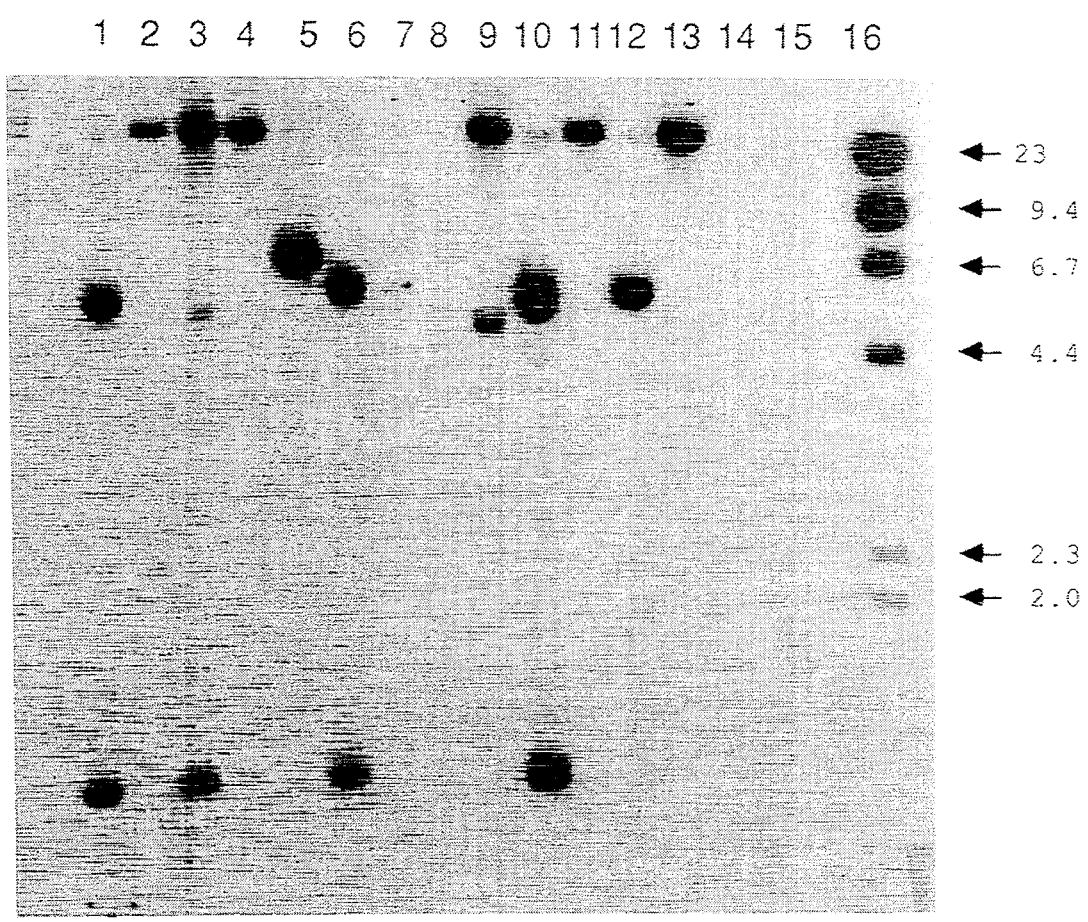
FIG. 3.2

FIG. 3.3
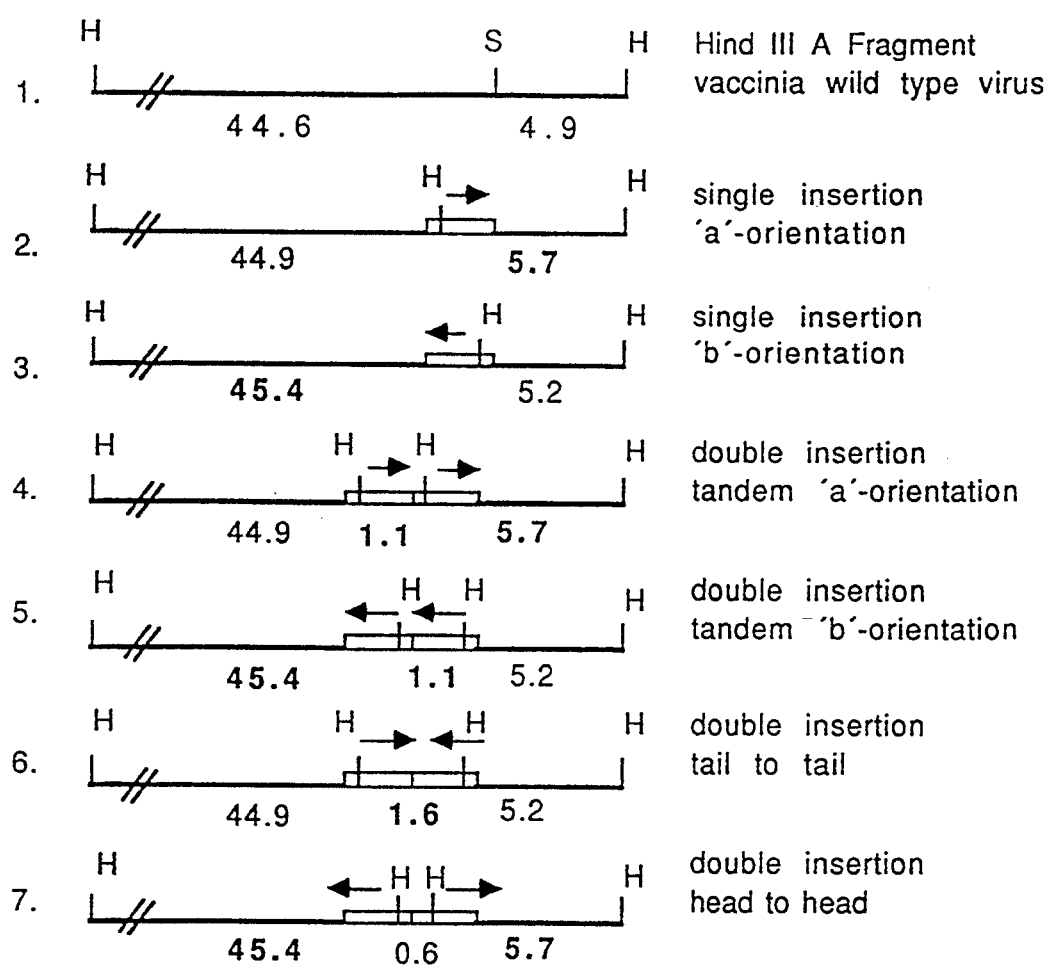

FIG. 4.1A
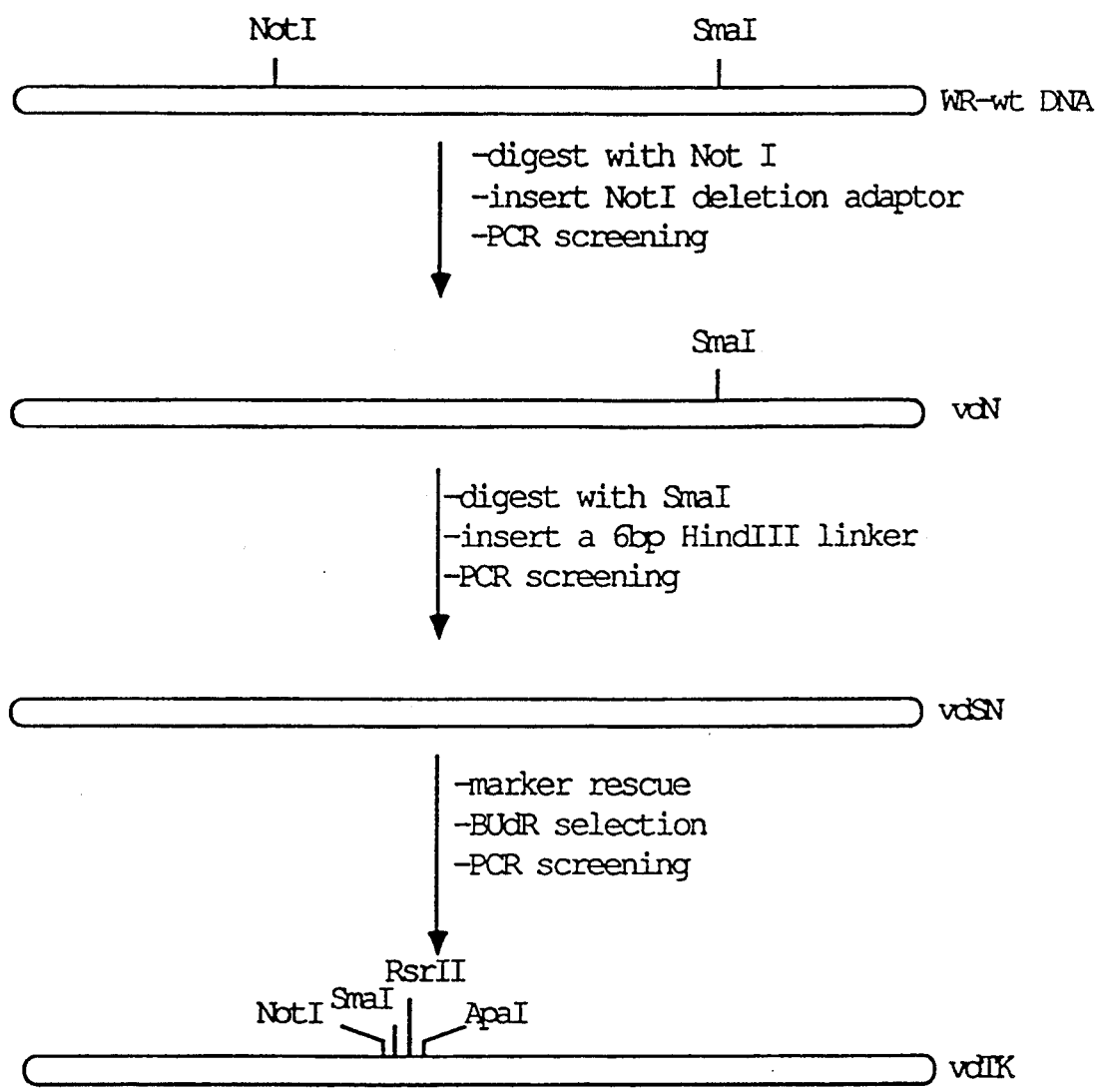

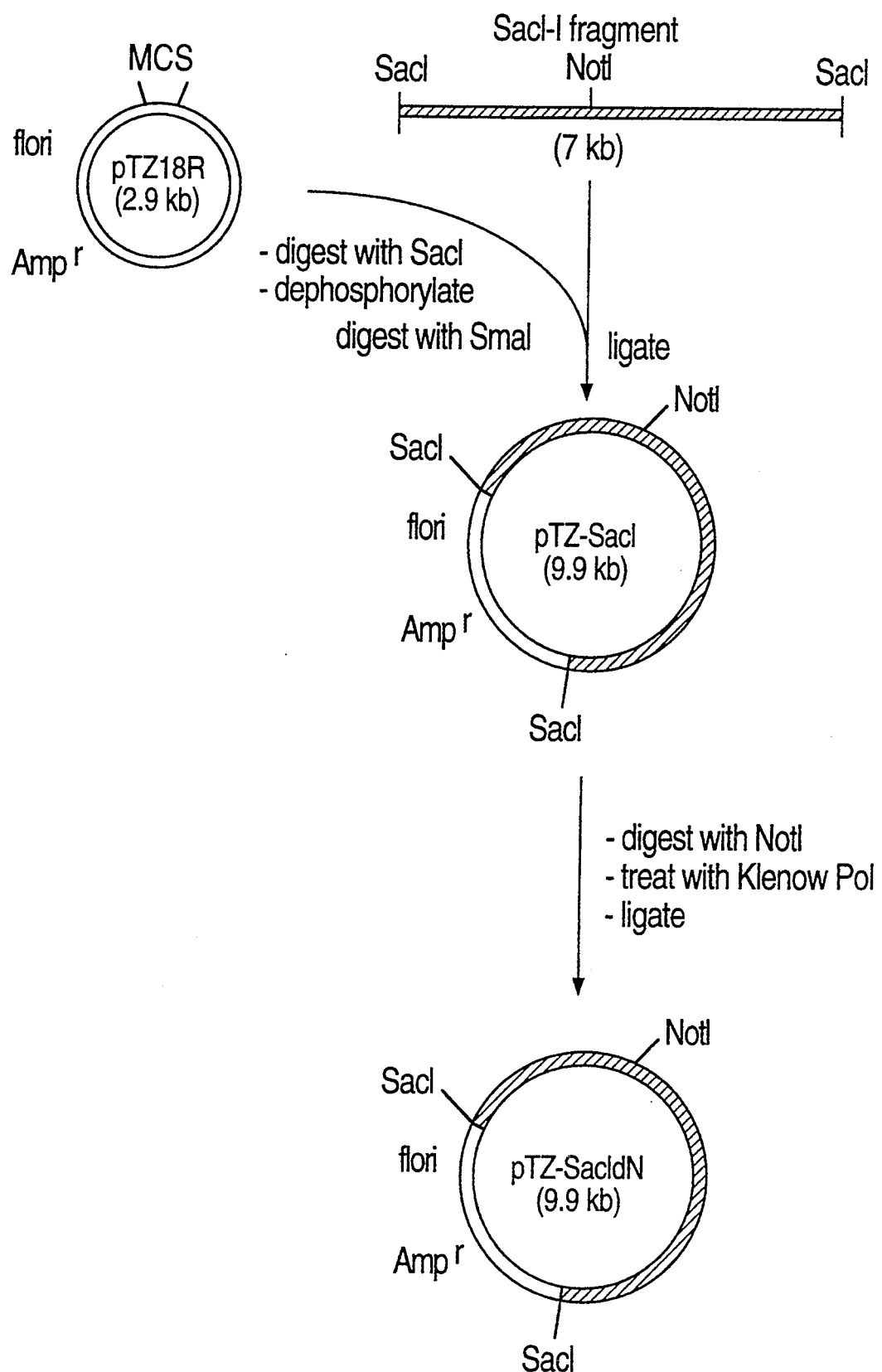
FIG. 4.1B

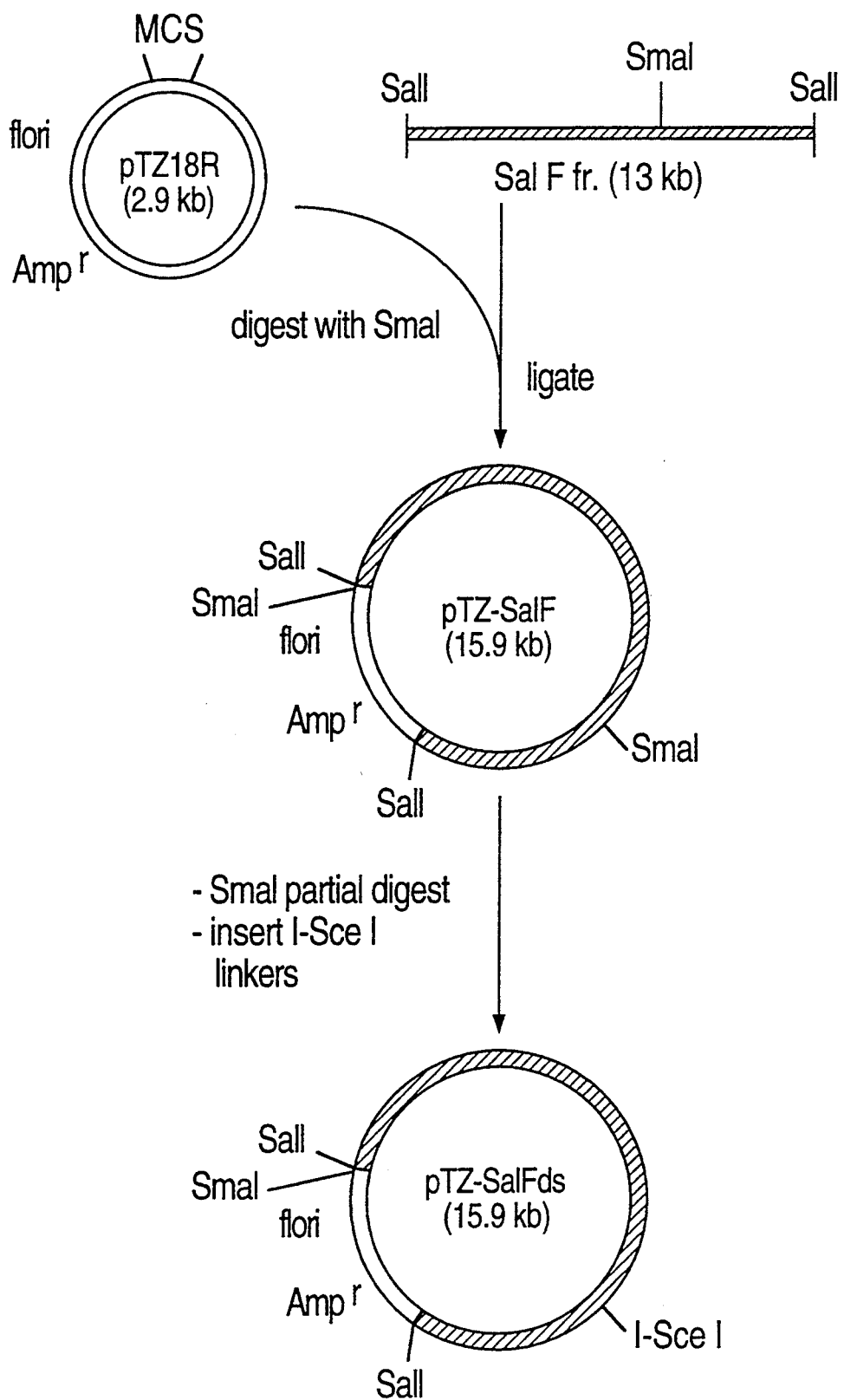
FIG. 4.1C

FIG. 4.2
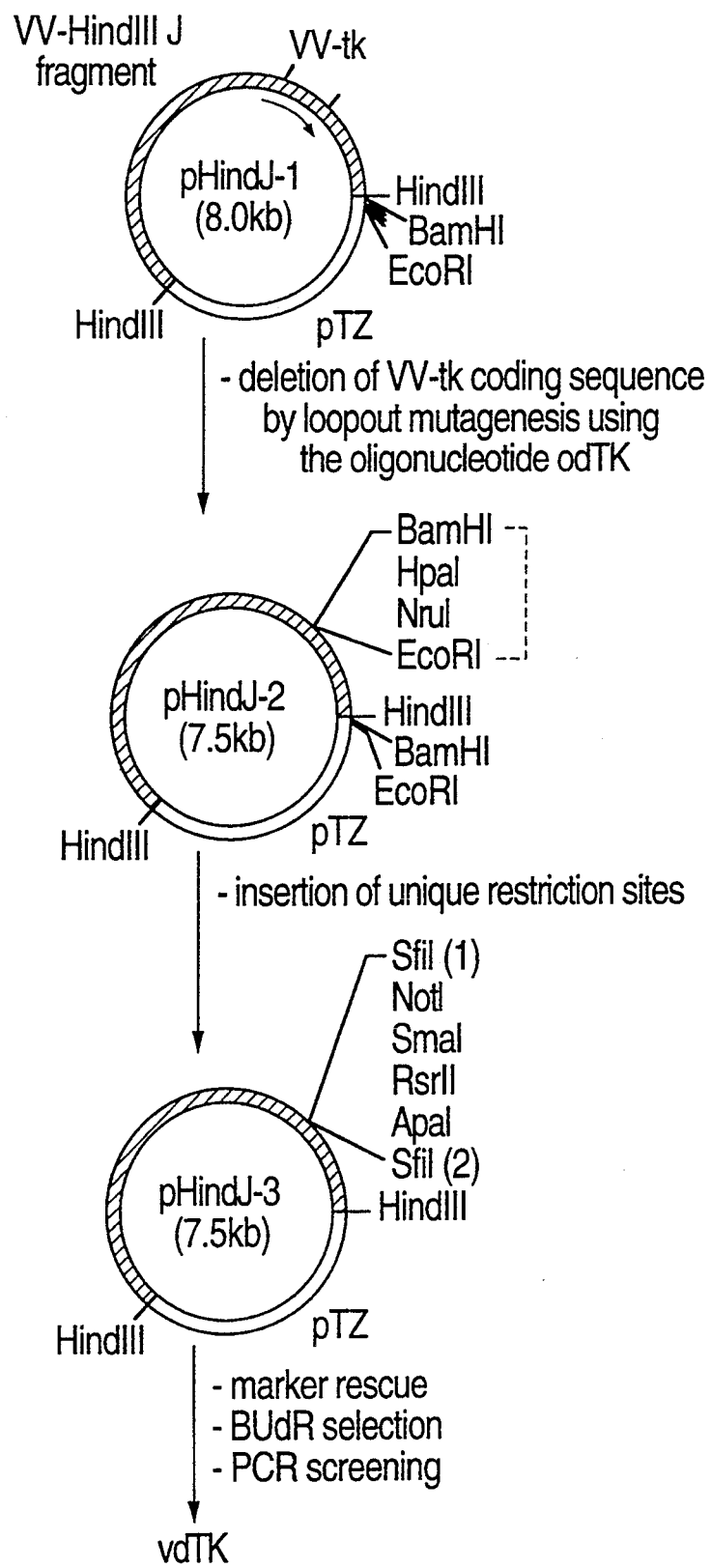

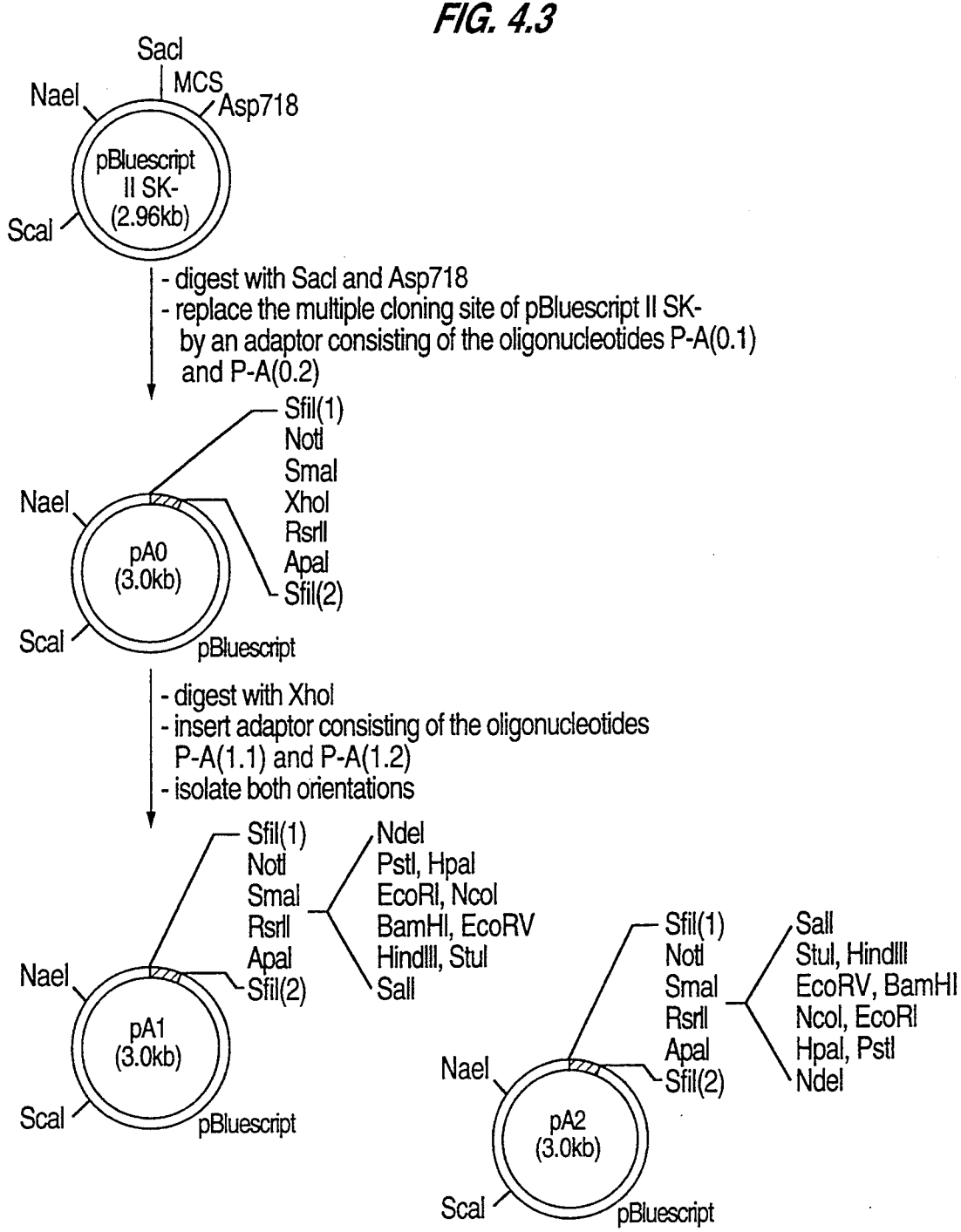
FIG. 4.3

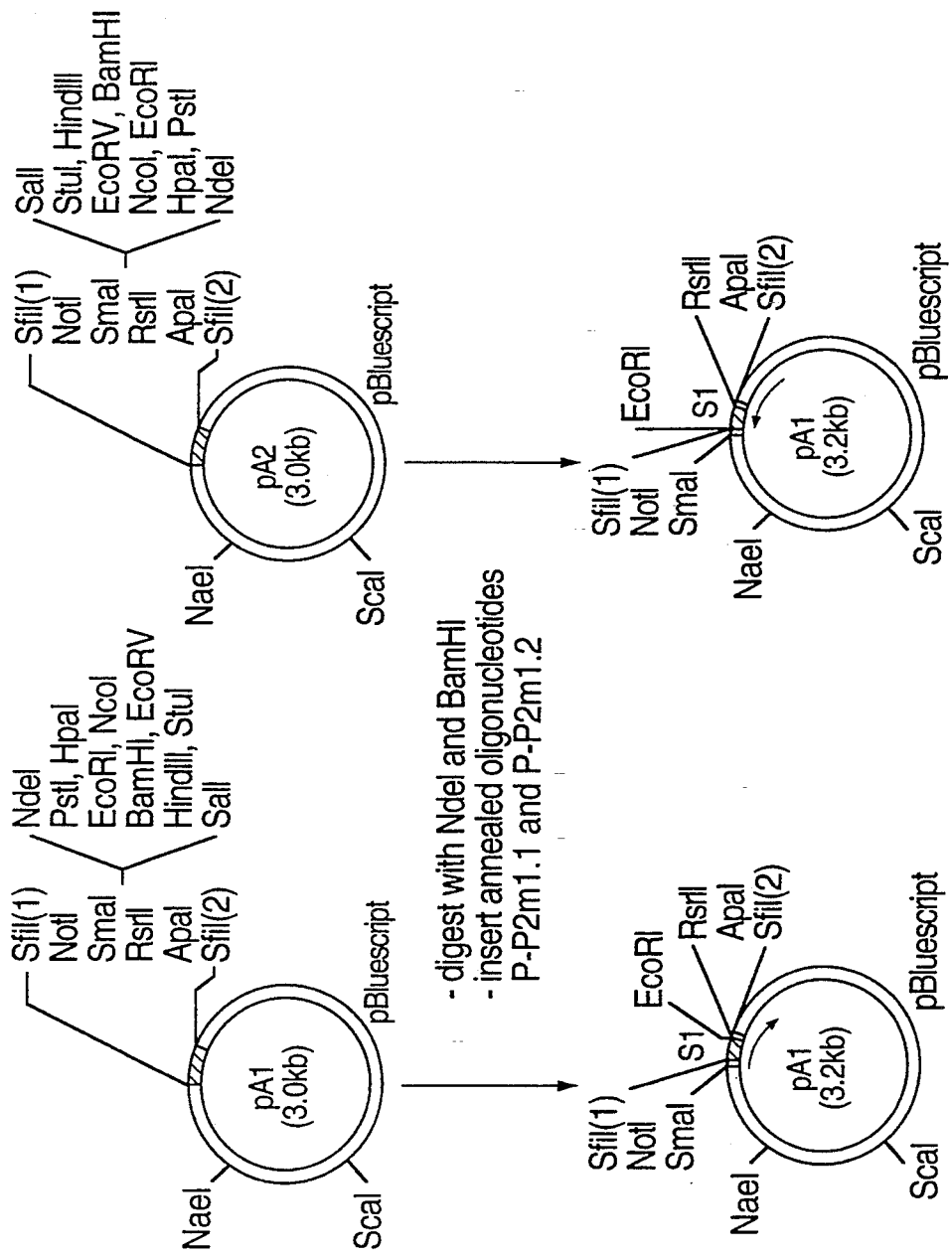
FIG. 4.4A

FIG. 4.4B
FIG. 4.5B

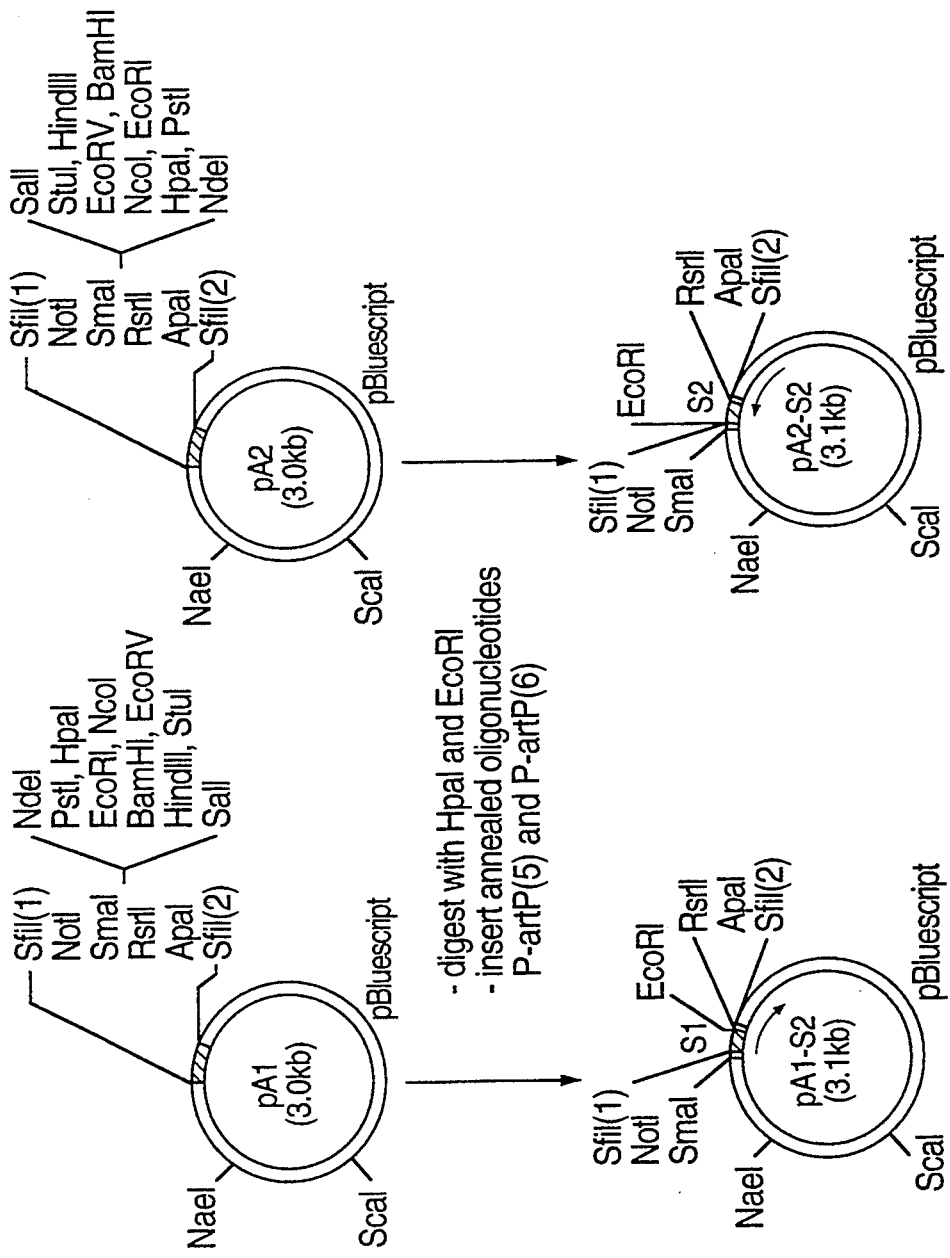
FIG. 4.5A

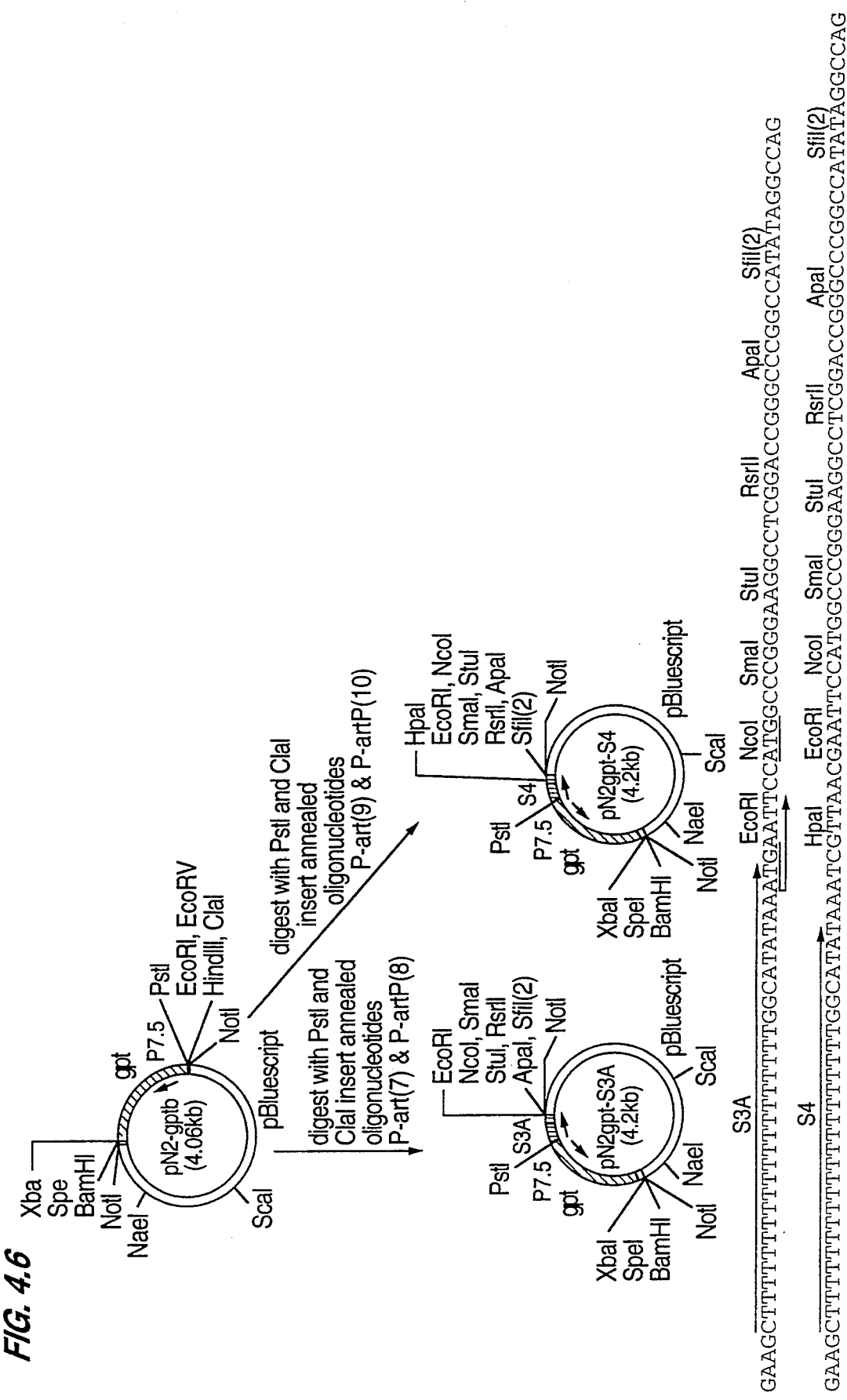
FIG. 4.6

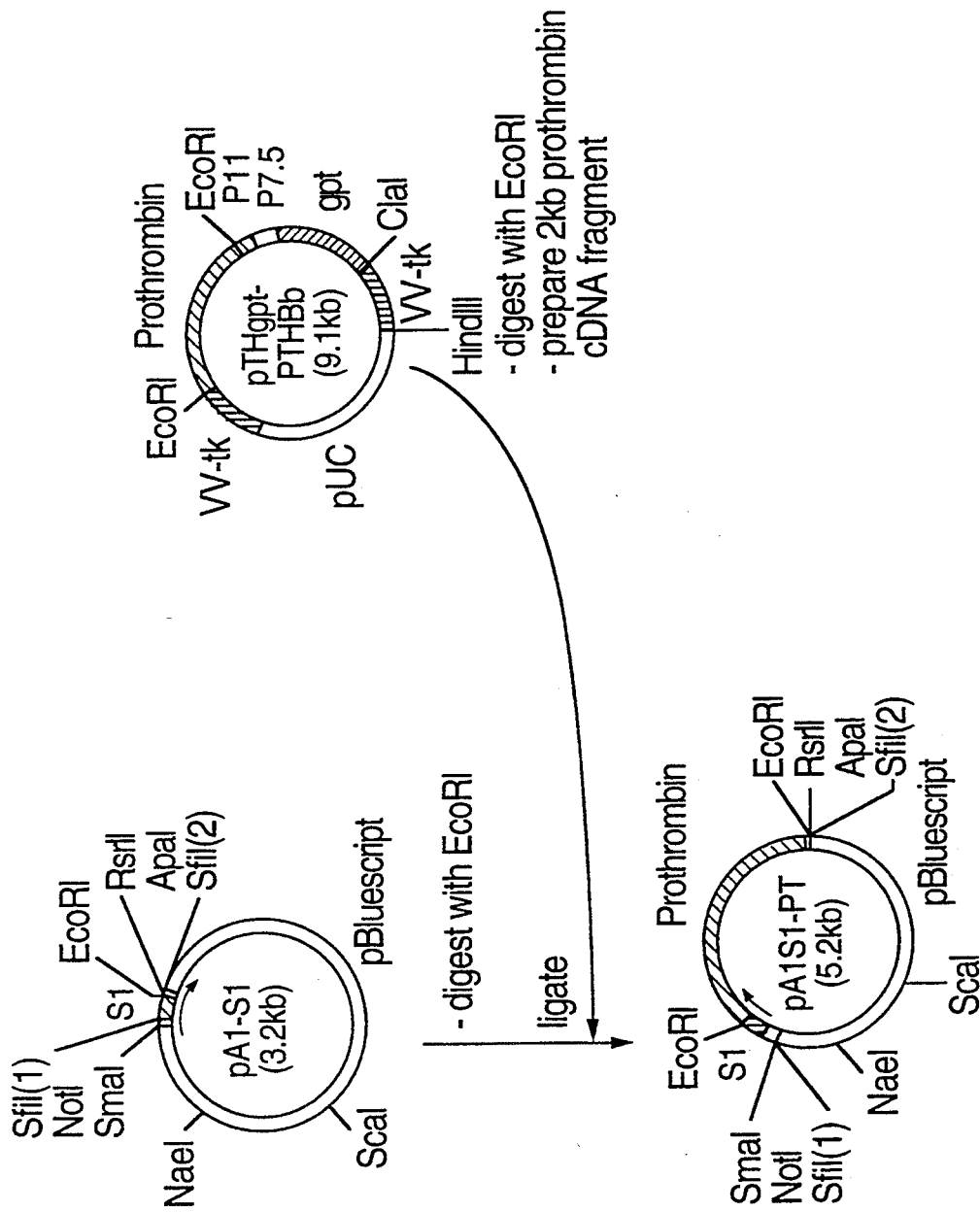
FIG. 5.1

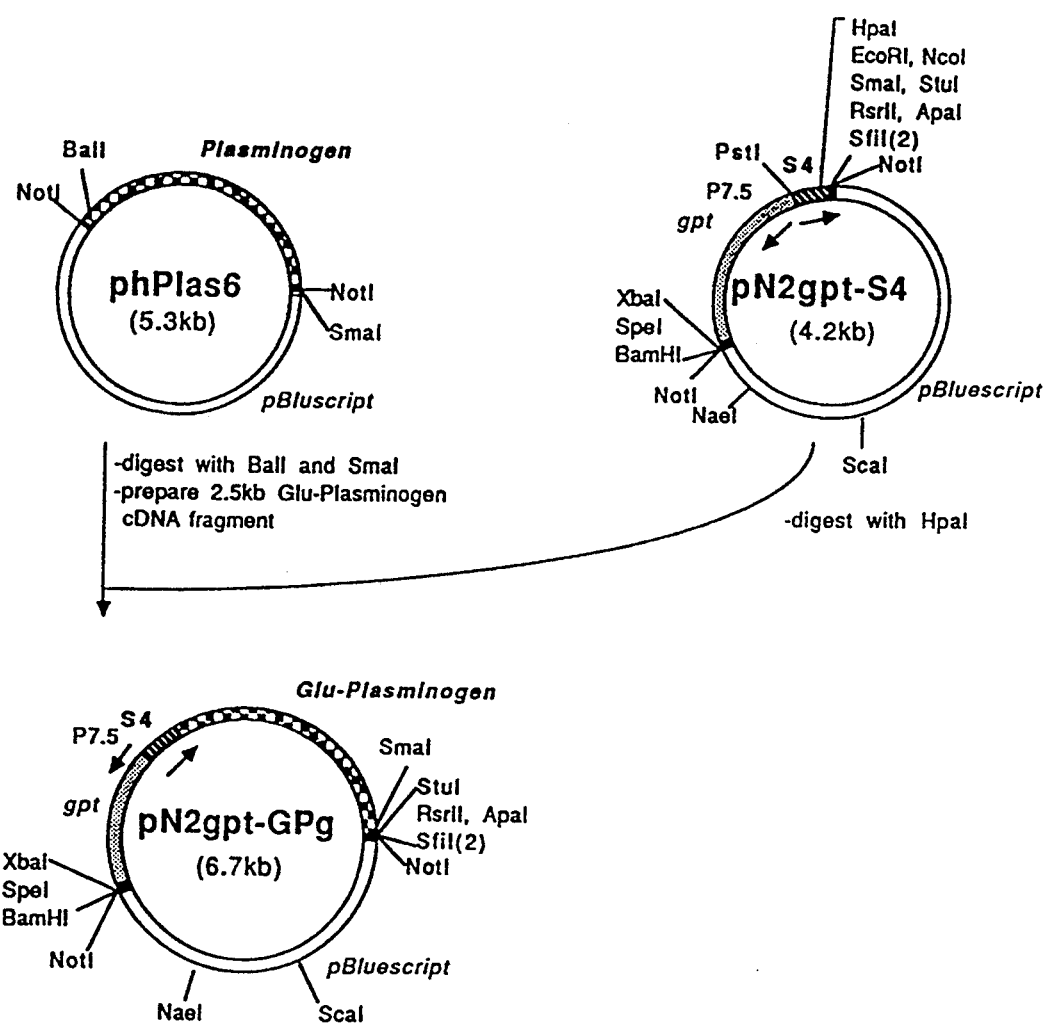
FIG. 5.2
Construction of the plasmid pN2gpt-GPg

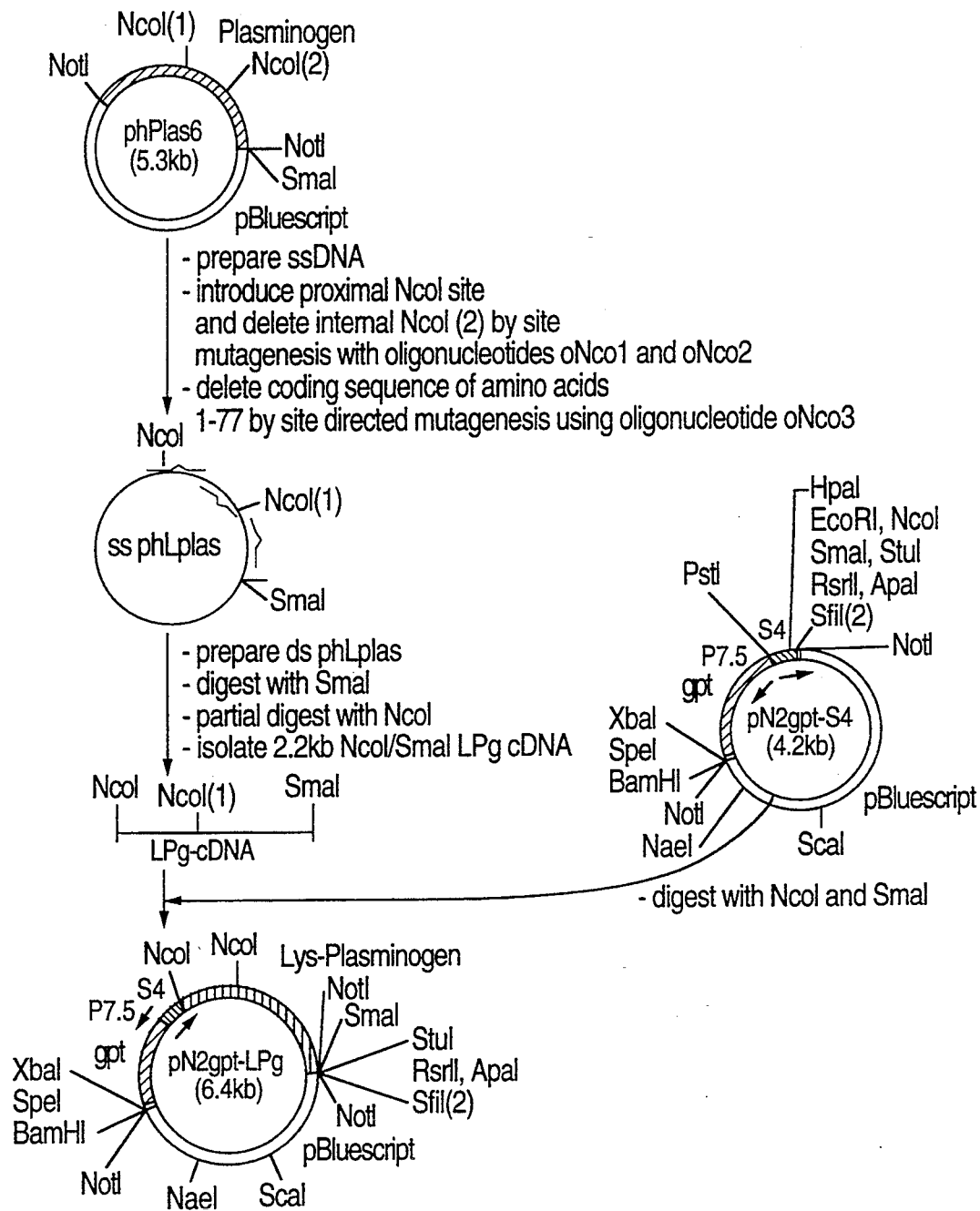
FIG. 5.3

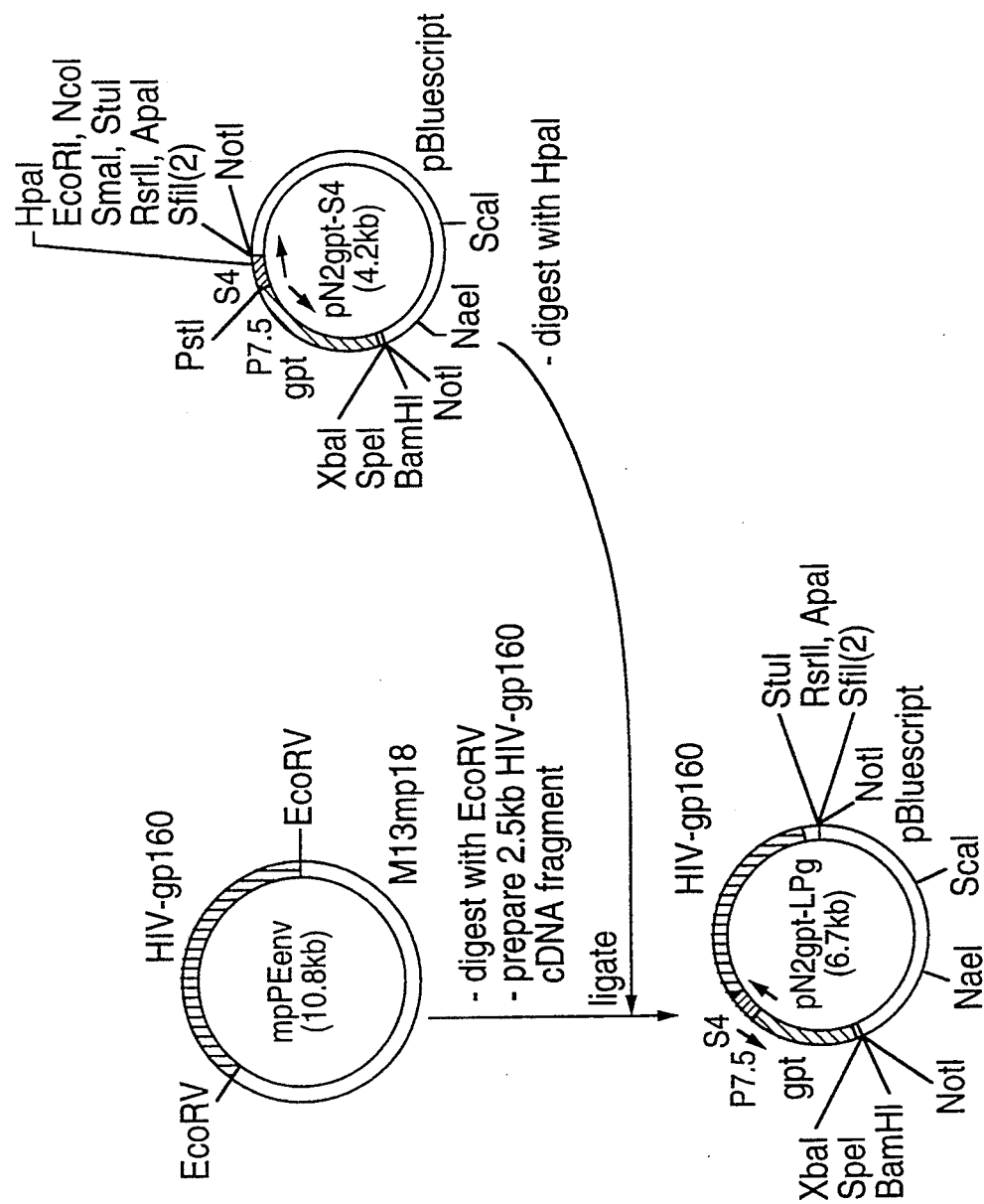
FIG. 5.4

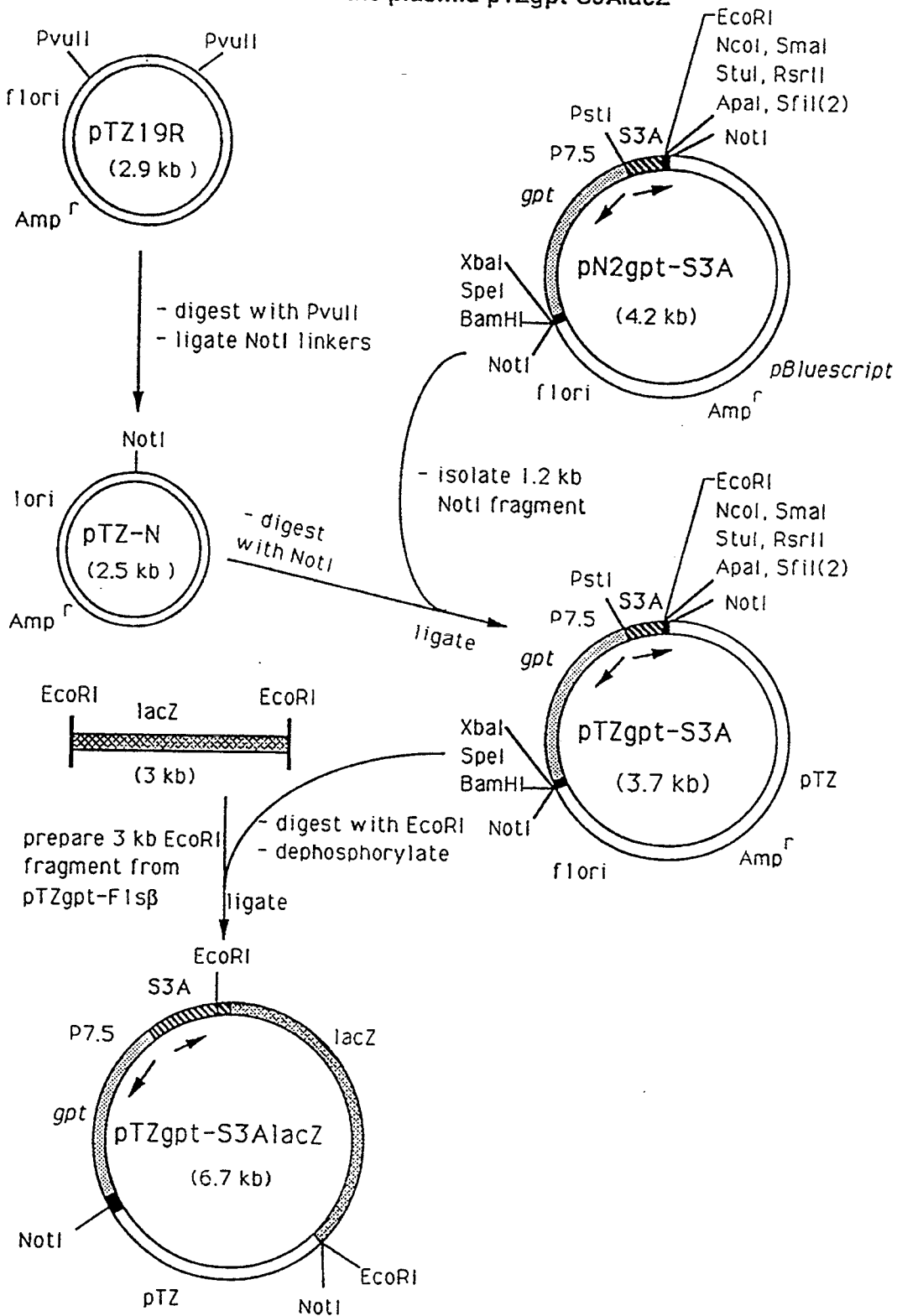
FIG. 5.5
Construction of the plasmid pTZgpt-S3AlacZ

FIG. 6.1
Construction of the VV vector vS4
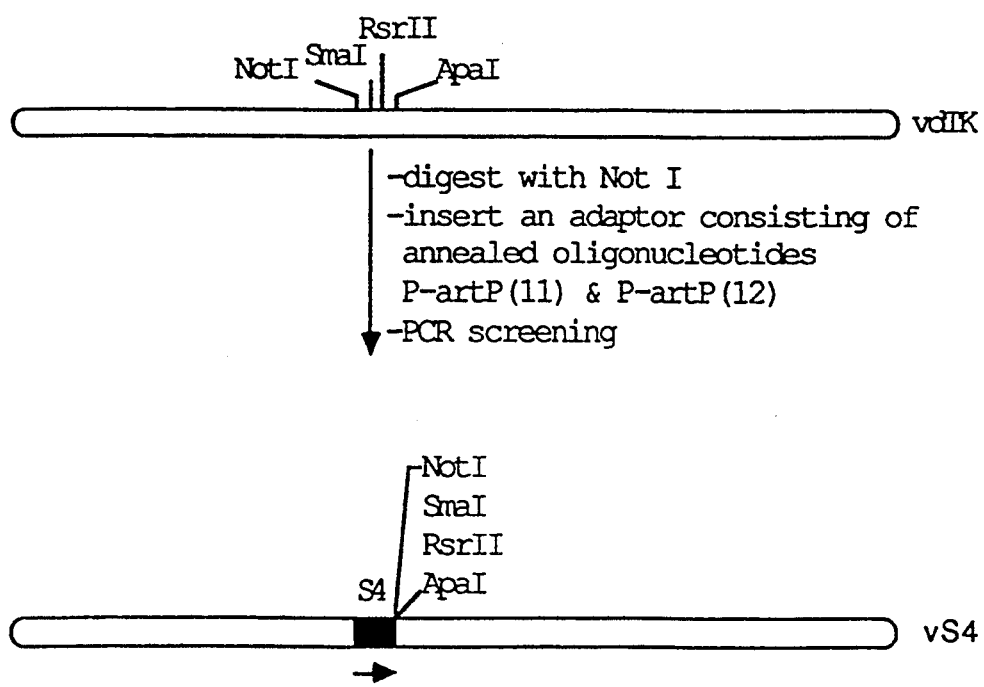
Structure of the promoter-adaptor in vS4
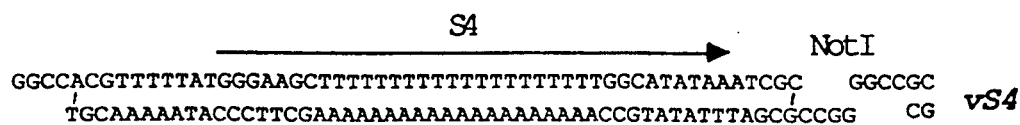

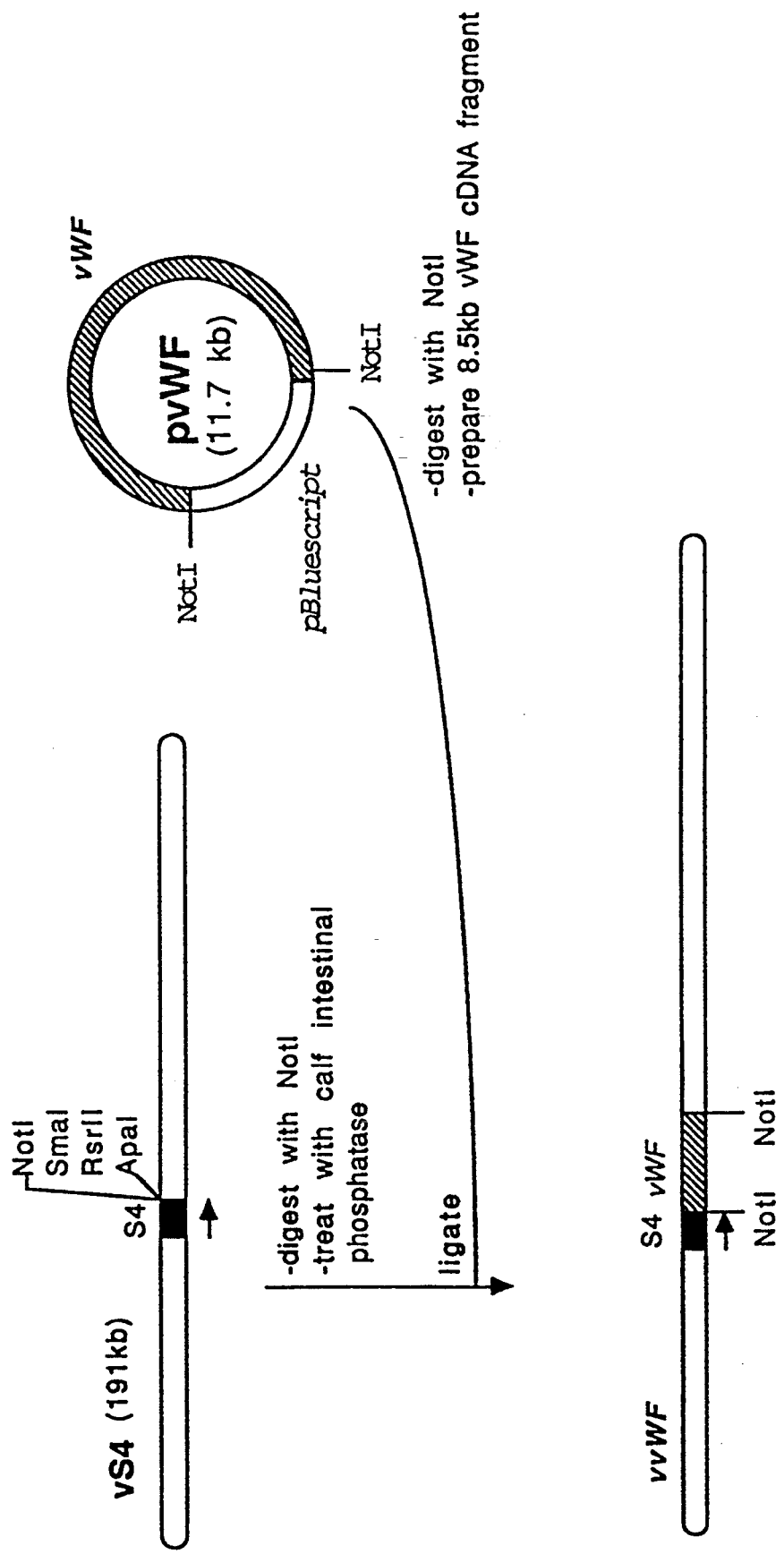
FIG. 6.2
Construction of the vaccinia virus strain vvWF

FIG. 7.1

Titer
x 10 6
(pfu/ml)

| vaccinia virus DNA added | 0.0 | 0.1 | 1.0 | 10.0 | 0.0 (ug) |
|---|---|---|---|---|---|
| | | 0,2 | 1 | 3,3 | |

In vivo packaging of vaccinia virus DNA with fowlpox virus in mammalian cells (CV-1)

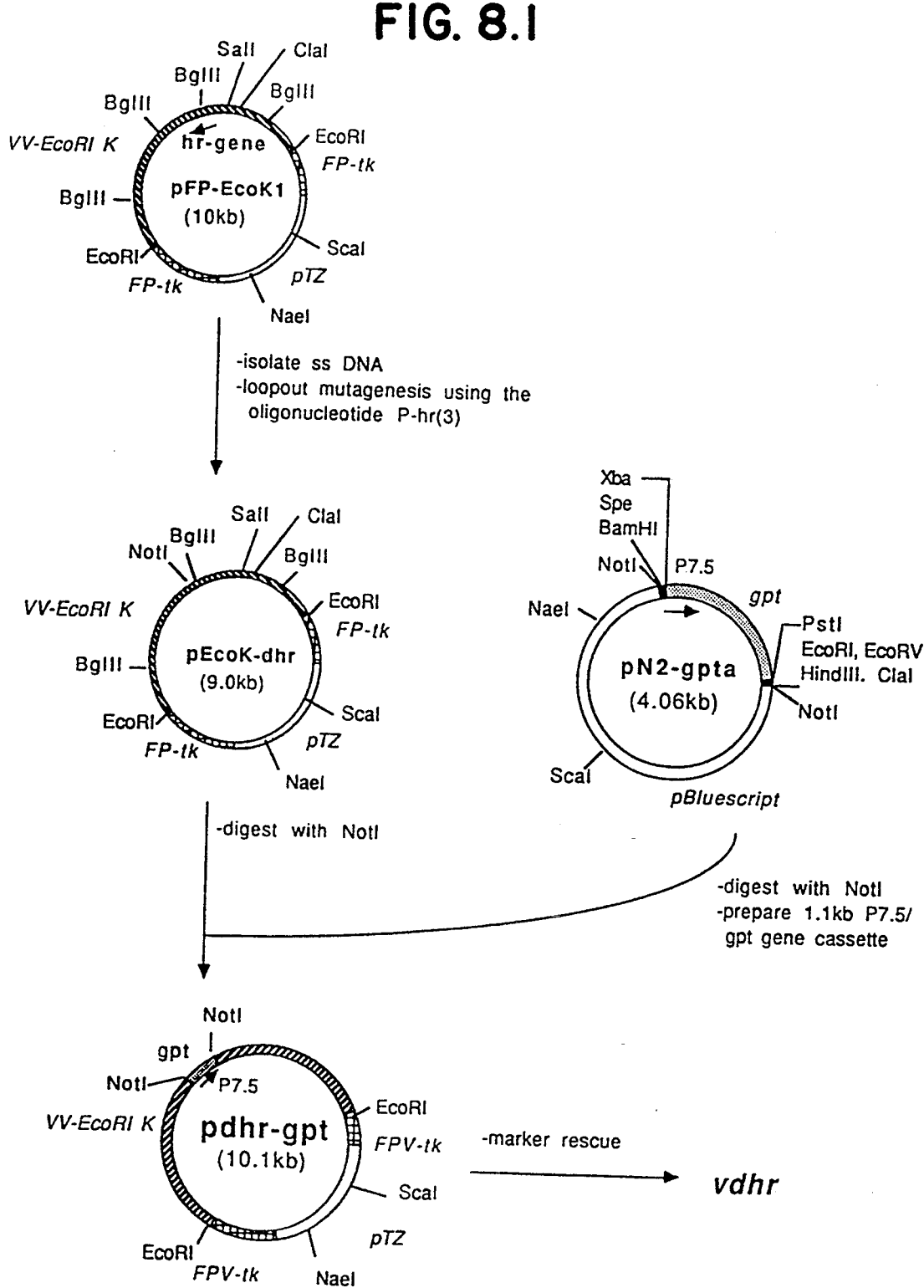
FIG. 8.1

SEQUENCE LISTING ( 1 ) GENERAL INFORMATION:

( i i i ) NUMBER OF SEQUENCES: 42

( 2 ) INFORMATION FOR SEQ ID NO:1:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: pN2 (Fig. 1.3)

( x i ) SEQUENCE DESCRIPTION: SEQ ID NO:1:

TCAAGCTTAT CGATACCGTC GCGGCCGCGA CCTCGAGGGG GGGCCCGG 48

( 2 ) INFORMATION FOR SEQ ID NO:2:

( i ) SEQUENCE CHARACTERISTICS:
( A ) LENGTH: 1133 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: pN2-gpta (Fig. 1.3)

( x i ) SEQUENCE DESCRIPTION: SEQ ID NO:2:

| | | | | | |
|---|---|---|---|---|---|
| CTAGAACTAG | TGGATCCCCC | AACTTAAGGG | TACCGCCTCG | ACATCTATAT | ACTATATAGT | 60 |
| AATACCAATA | CTCAAGACTA | CGAAACTGAT | ACAATCTCTT | ATCATGTGGG | TAATGTTCTC | 120 |
| GATGTCGAAT | AGCCATATGC | CGGTAGTTGC | GATATACATA | AACTGATCAC | TAATTCCAAA | 180 |
| CCCACCCGCT | TTTTATAGTA | AGTTTTCAC | CCATAAATAA | TAAATACAAT | AATTAATTTC | 240 |
| TCGTAAAAGT | AGAAAATATA | TTCTAATTTA | TTGCACGGTA | AGGAAGTAGA | ATCATAAAGA | 300 |
| ACAGTGACGG | ATGATCCCCA | AGCTTGGACA | CAAGACAGGC | TTGCGAGATA | TGTTTGAGAA | 360 |
| TACCACTTTA | TCCCGCGTCA | GGGAGAGGCA | GTGCGTAAAA | AGACGCGGAC | TCATGTGAAA | 420 |
| TACTGGTTTT | TAGTGCGCCA | GATCTCTATA | ATCTCGCGCA | ACCTATTTC | CCCTCGAACA | 480 |
| CTTTTTAAGC | CGTAGATAAA | CAGGCTGGGA | CACTTCACAT | GAGCGAAAAA | TACATCGTCA | 540 |
| CCTGGGACAT | GTTGCAGATC | CATGCACGTA | AACTCGCAAG | CCGACTGATG | CCTTCTGAAC | 600 |
| AATGGAAAGG | CATTATTGCC | GTAAGCCGTG | GCGGTCTGGT | ACCGGGTGCG | TTACTGGCGC | 660 |
| GTGAACTGGG | TATTCGTCAT | GTCGATACCG | TTTGTATTTC | CAGCTACGAT | CACGACAACC | 720 |
| AGCGCGAGCT | TAAAGTGCTG | AAACGCGCAG | AAGGCGATGG | CGAAGGCTTC | ATCGTTATTG | 780 |
| ATGACCTGGT | GGATACCGGT | GGTACTGCGG | TTGCGATTCG | TGAAATGTAT | CCAAAAGCGC | 840 |
| ACTTTGTCAC | CATCTTCGCA | AAACCGGCTG | GTCGTCCGCT | GGTTGATGAC | TATGTTGTTG | 900 |
| ATATCCCGCA | AGATACCTGG | ATTGAACAGC | CGTGGGATAT | GGGCGTCGTA | TTCGTCCCGC | 960 |
| CAATCTCCGG | TCGCTAATCT | TTTCAACGCC | TGGCACTGCC | GGGCGTTGTT | CTTTTAACT | 1020 |
| TCAGGCGGGT | TACAATAGTT | TCCAGTAAGT | ATTCTGGAGG | CTGCATCCAT | GACACAGGCA | 1080 |
| AACCTGAGCG | AAACCCTGTT | CAAACCCCGC | TTTGGGCTGC | AGGAATTCGA | TAT | 1133 |

( 2 ) INFORMATION FOR SEQ ID NO:3:

( i ) SEQUENCE CHARACTERISTICS:
        ( A ) LENGTH: 1133 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: pN2-gptb (Fig. 1.3)

( x i ) SEQUENCE DESCRIPTION: SEQ ID NO:3:

| | | | | | |
|---|---|---|---|---|---|
| CTAGAACTAG | TGGATCCCCC | AAAGCGGGGT | TTGAACAGGG | TTTCGCTCAG | GTTTGCCTGT | 60 |
| GTCATGGATG | CAGCCTCCAG | AATACTTACT | GGAAACTATT | GTAACCCGCC | TGAAGTTAAA | 120 |
| AGAACAACG | CCCGGCAGTG | CCAGGCGTTG | AAAAGATTAG | CGACCGGAGA | TTGGCGGGAC | 180 |
| GAATACGACG | CCCATATCCC | ACGGCTGTTC | AATCCAGGTA | TCTTGCGGGA | TATCAACAAC | 240 |
| ATAGTCATCA | ACCAGCGGAC | GACCAGCCGG | TTTTGCGAAG | ATGGTGACAA | AGTGCGCTTT | 300 |
| TGGATACATT | TCACGAATCG | CAACCGCAGT | ACCACCGGTA | TCCACCAGGT | CATCAATAAC | 360 |
| GATGAAGCCT | TCGCCATCGC | CTTCTGCGCG | TTTCAGCACT | TTAAGCTCGC | GCTGGTTGTC | 420 |
| GTGATCGTAG | CTGGAAATAC | AAACGGTATC | GACATGACGA | ATACCCAGTT | CACGCGCCAG | 480 |
| TAACGCACCC | GGTACCAGAC | CGCCACGGCT | TACGGCAATA | ATGCCTTTCC | ATTGTTCAGA | 540 |
| AGGCATCAGT | CGGCTTGCGA | GTTTACGTGC | ATGGATCTGC | AACATGTCCC | AGGTGACGAT | 600 |
| GTATTTTTCG | CTCATGTGAA | GTGTCCCAGC | CTGTTTATCT | ACGGCTTAAA | AAGTGTTCGA | 660 |
| GGGGAAAATA | GGTTGCGCGA | GATTATAGAG | ATCTGGCGCA | CTAAAAACCA | GTATTTCACA | 720 |
| TGAGTCCGCG | TCTTTTTACG | CACTGCCTCT | CCCTGACGCG | GGATAAAGTG | GTATTCTCAA | 780 |

| ACATATCTCG | CAAGCCTGTC | TTGTGTCCAA | GCTTGGGGAT | CATCCGTCAC | TGTTCTTTAT | 840 |
| GATTCTACTT | CCTTACCGTG | CAATAAATTA | GAATATATTT | TCTACTTTTA | CGAGAAATTA | 900 |
| ATTATTGTAT | TTATTATTTA | TGGGTGAAAA | ACTTACTATA | AAAAGCGGGT | GGGTTTGGAA | 960 |
| TTAGTGATCA | GTTTATGTAT | ATCGCAACTA | CCGGCATATG | GCTATTCGAC | ATCGAGAACA | 1020 |
| TTACCCACAT | GATAAGAGAT | TGTATCAGTT | TCGTAGTCTT | GAGTATTGGT | ATTACTATAT | 1080 |
| AGTATATAGA | TGTCGAGGCG | GTACCCTTAA | GTTGGGCTGC | AGGAATTCGA | TAT | 1133 |

( 2 ) INFORMATION FOR SEQ ID NO:4:

( i ) SEQUENCE CHARACTERISTICS:
          ( A ) LENGTH: 66 base pairs
          ( B ) TYPE: nucleic acid
          ( C ) STRANDEDNESS: single
          ( D ) TOPOLOGY: linear ( i i ) MOLECULE TYPE: DNA (genomic)

( v i i ) IMMEDIATE SOURCE:
          ( B ) CLONE: pHindJ-2 (Fig. 4.2)

( x i ) SEQUENCE DESCRIPTION: SEQ ID NO:4:

| CGCATTTTCT | AACGTGATGG | GATCCGTTAA | CTCGCGAGAA | TTCTGTAGAA | AGTGTTACAT | 60 |
| CGACTC | | | | | | 66 |

( 2 ) INFORMATION FOR SEQ ID NO:5:

( i ) SEQUENCE CHARACTERISTICS:
          ( A ) LENGTH: 127 base pairs
          ( B ) TYPE: nucleic acid
          ( C ) STRANDEDNESS: single
          ( D ) TOPOLOGY: linear ( i i ) MOLECULE TYPE: DNA (genomic)

( v i i ) IMMEDIATE SOURCE:
          ( B ) CLONE: pHindJ-3 (Fig. 4.2)

( x i ) SEQUENCE DESCRIPTION: SEQ ID NO:5:

| CGCATTTTCT | AACGTGATGG | GATCCGGCCG | GCTAGGCCGC | GGCCGCCCGG | GTTTTATCT | 60 |
| CGAGACAAAA | AGACGGACCG | GGCCCGGCCA | TATAGGCCCA | ATTCTGTAGA | AAGTGTTACA | 120 |
| TCGACTC | | | | | | 127 |

( 2 ) INFORMATION FOR SEQ ID NO:6:

( i ) SEQUENCE CHARACTERISTICS:
          ( A ) LENGTH: 115 base pairs
          ( B ) TYPE: nucleic acid
          ( C ) STRANDEDNESS: single
          ( D ) TOPOLOGY: linear ( i i ) MOLECULE TYPE: DNA (genomic)

( v i i ) IMMEDIATE SOURCE:
          ( B ) CLONE: pA0 (Fig. 4.3)

( x i ) SEQUENCE DESCRIPTION: SEQ ID NO:6:

| AGGGAACAAA | AGCTGGAGCT | AGGCCGGCTA | GGCCGCGGCC | GCCCGGGTTT | TTATCTCGAG | 60 |
| ACAAAAAGAC | GGACCGGGCC | CGGCCATATA | GGCCAGTACC | CAATTCGCCC | TATAG | 115 |

( 2 ) INFORMATION FOR SEQ ID NO:7:

( i ) SEQUENCE CHARACTERISTICS:
          ( A ) LENGTH: 103 base pairs
          ( B ) TYPE: nucleic acid
          ( C ) STRANDEDNESS: single
          ( D ) TOPOLOGY: linear ( i i ) MOLECULE TYPE: DNA (genomic)

( v i i ) IMMEDIATE SOURCE:
        ( B ) CLONE: pA1 (Fig. 4.3)

( x i ) SEQUENCE DESCRIPTION: SEQ ID NO:7:

| CGGCCGCCCG | GGTTTTTATC | TCGACATATG | CTGCAGTTAA | CGAATTCCAT | GGGGATCCGA | 60 |
| TATCAAGCTT | AGGCCTGTCG | ACGTCGAGAC | AAAAGACGG | ACC | | 103 |

( 2 ) INFORMATION FOR SEQ ID NO:8:

( i ) SEQUENCE CHARACTERISTICS:
        ( A ) LENGTH: 103 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: pA2 (Fig. 4.3)

( x i ) SEQUENCE DESCRIPTION: SEQ ID NO:8:

| CGGCCGCCCG | GGTTTTTATC | TCGACGTCGA | CAGGCCTAAG | CTTGATATCG | GATCCCCATG | 60 |
| GAATTCGTTA | ACTGCAGCAT | ATGTCGAGAC | AAAAGACGG | ACC | | 103 |

( 2 ) INFORMATION FOR SEQ ID NO:9:

( i ) SEQUENCE CHARACTERISTICS:
        ( A ) LENGTH: 213 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: pA1-S1 (Fig. 4.4)

( x i ) SEQUENCE DESCRIPTION: SEQ ID NO:9:

| CCCGGGTTTT | TATCTCGACA | TACGGCTTGG | TATAGCGGAC | AACTAAGTAA | TTGTAAAGAA | 60 |
| GAAAACGAAA | CTATCAAAAC | CGTTTATGAA | ATGATAGAAA | AAAGAATATA | AATAATCCTG | 120 |
| TATTTTAGTT | TAAGTAACAG | TAAAATAATG | AGTAGAAAAT | ACTATTTTTT | ATAGCCTATA | 180 |
| AATCATGAAT | TCGGATCCGA | TATCAAGCTT | AGG | | | 213 |

( 2 ) INFORMATION FOR SEQ ID NO:10:

( i ) SEQUENCE CHARACTERISTICS:
        ( A ) LENGTH: 215 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: pA2-S1 (Fig. 4.4)

( x i ) SEQUENCE DESCRIPTION: SEQ ID NO:10:

| CAGGCCTAAG | CTTGATATCG | GATCCGAATT | CATGATTTAT | AGGCTATAAA | AAATAGTATT | 60 |
| TTCTACTCAT | TATTTTACTG | TTACTTAAAC | TAAAATACAG | GATTATTTAT | ATTCTTTTTT | 120 |
| CTATCATTTC | ATAAACGGTT | TTGATAGTTT | CGTTTTCTTC | TTTACAATTA | CTTAGTTGTC | 180 |
| CGCTATACCA | AGCCGTATGT | CGAGACAAAA | AGACG | | | 215 |

( 2 ) INFORMATION FOR SEQ ID NO:11:

( i ) SEQUENCE CHARACTERISTICS:
( A ) LENGTH: 88 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: pA1-S2 (Fig. 4.5)

( x i ) SEQUENCE DESCRIPTION: SEQ ID NO:11:

```
TCTCGACATA TGCTGCAGTT GGGAAGCTTT TTTTTTTTT TTTTTTGGC ATATAAATAG      60
GCTGCAGGAA TTCCATGGGG ATCCGATA                                       88
```

( 2 ) INFORMATION FOR SEQ ID NO:12:

( i ) SEQUENCE CHARACTERISTICS:
( A ) LENGTH: 92 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: pA2-S2 (Fig. 4.5)

( x i ) SEQUENCE DESCRIPTION: SEQ ID NO:12:

```
TTGATATCGG ATCCCCATGG AATTCCTGCA GCCTATTTAT ATGCCAAAAA AAAAAAAAA     60
AAAAGCTTC CCAACTGCAG CATATGTCGA GA                                   92
```

( 2 ) INFORMATION FOR SEQ ID NO:13:

( i ) SEQUENCE CHARACTERISTICS:
( A ) LENGTH: 127 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: pN2gpt-S3A (fig. 4.7)

( x i ) SEQUENCE DESCRIPTION: SEQ ID NO:13:

```
TACCCTTAAG TTGGGCTGCA GAAGCTTTTT TTTTTTTTT TTTTGGCAT ATAAATGAAT      60
TCCATGGCCC GGGAAGGCCT CGGACCGGGC CCGGCCATAT AGGCCAGCGA TACCGTCGCG   120
GCCGCGA                                                              127
```

( 2 ) INFORMATION FOR SEQ ID NO:14:

( i ) SEQUENCE CHARACTERISTICS:
( A ) LENGTH: 134 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: pN2gpt-S4

( x i ) SEQUENCE DESCRIPTION: SEQ ID NO:14:

```
TACCCTTAAG TTGGGCTGCA GAAGCTTTTT TTTTTTTTT TTTTGGCAT ATAAATCGTT      60
AACGAATTCC ATGGCCCGGG AAGGCCTCGG ACCGGGCCCG GCCATATAGG CCAGCGATAC   120
CGTCGCGGCC GCGA                                                      134
```

( 2 ) INFORMATION FOR SEQ ID NO:15:

( i ) SEQUENCE CHARACTERISTICS:
    ( A ) LENGTH: 1988 base pairs
    ( B ) TYPE: nucleic acid
    ( C ) STRANDEDNESS: single
    ( D ) TOPOLOGY: linear ( i i ) MOLECULE TYPE: DNA (genomic)

( v i i ) IMMEDIATE SOURCE:
    ( B ) CLONE: pA1S1-PT (Fig. 5.1)

( x i ) SEQUENCE DESCRIPTION: SEQ ID NO:15:

| | | | | | | |
|---|---|---|---|---|---|---|
| TTTTATAGCC | TATAAATCAT | GAATTCCGCG | CACGTCCGAG | GCTTGCAGCT | GCCTGGCTGC | 60 |
| CTGGCCCTGG | CTGCCCTGTG | TAGCCTTGTG | CACAGCCAGC | ATGTGTTCCT | GGCTCCTCAG | 120 |
| CAAGCACGGT | CGCTGCTCCA | GCGGGTCCGG | CGAGCCAACA | CCTTCTTGGA | GGAGGTGCGC | 180 |
| AAGGGCAACC | TAGAGCGAGA | GTGCGTGGAG | GAGACGTGCA | GCTACGAGGA | GGCCTTCGAG | 240 |
| GCTCTGGAGT | CCTCCACGGC | TACGGATGTG | TTCTGGGCCA | AGTACACAGC | TTGTGAGACA | 300 |
| GCGAGGACGC | CTCGAGATAA | GCTTGCTGCA | TGTCTGGAAG | GTAACTGTGC | TGAGGGTCTG | 360 |
| GGTACGAACT | ACCGAGGGCA | TGTGAACATC | ACCCGGTCAG | GCATTGAGTG | CCAGCTATGG | 420 |
| AGGAGTCGCT | ACCCACATAA | GCCTGAAATC | AACTCCACTA | CCCATCCTGG | GGCCGACCTA | 480 |
| CAGGAGAATT | TCTGCCGCAA | CCCCGACAGC | AGCAACACGG | GACCATGGTG | CTACACTACA | 540 |
| GACCCCACCG | TGAGGAGGCA | GGAATGCAGC | ATCCTGTCT | GTGGCCAGGA | TCAAGTCACT | 600 |
| GTAGCGATGA | CTCCACGCTC | CGAAGGCTCC | AGTGTGAATC | TGTCACCTCC | ATTGGAGCAG | 660 |
| TGTGTCCCTG | ATCGGGGGCA | GCAGTACCAG | GGGCGCCTGG | CGGTGACCAC | ACATGGGCTC | 720 |
| CCCTGCCTGG | CCTGGGCCAG | CGCACAGGCC | AAGGCCCTGA | GCAAGCACCA | GGACTTCAAC | 780 |
| TCAGCTGTGC | AGCTGGTGGA | GAACTTCTGC | CGCAACCCAG | ACGGGGATGA | GGAGGGCGTG | 840 |
| TGGTGCTATG | TGGCCGGGAA | GCCTGGCGAC | TTTGGGTACT | GCGACCTCAA | CTATTGTGAG | 900 |
| GAGGCCGTGG | AGGAGGAGAC | AGGAGATGGG | CTGGATGAGG | ACTCAGACAG | GGCCATCGAA | 960 |
| GGGCGTACCG | CCACAAGTGA | GTACCAGACT | TTCTTCAATC | CGAGGACCTT | TGGCTCGGGA | 1020 |
| GAGGCAGACT | GTGGGCTGCG | ACCTCTGTTC | GAGAAGAAGT | CGCTGGAGGA | CAAAACCGAA | 1080 |
| AGAGAGCTCC | TGGAATCCTA | CATCGACGGG | CGCATTGTGG | AGGGCTCGGA | TGCAGAGATC | 1140 |
| GGCATGTCAC | CTTGGCAGGT | GATGCTTTTC | CGGAAGAGTC | CCCAGGAGCT | GCTGTGTGGG | 1200 |
| GCCAGCCTCA | TCAGTGACCG | CTGGGTCCTC | ACCGCCGCCC | ACTGCCTCCT | GTACCCGCCC | 1260 |
| TGGGACAAGA | ACTTCACCGA | GAATGACCTT | CTGGTGCGCA | TTGGCAAGCA | CTCCCGCACC | 1320 |
| AGGTACGAGC | GAAACATTGA | AAAGATATCC | ATGTTGGAAA | AGATCTACAT | CCACCCCAGG | 1380 |
| TACAACTGGC | GGGAGAACCT | GGACCGGGAC | ATTGCCCTGA | TGAAGCTGAA | GAAGCCTGTT | 1440 |
| GCCTTCAGTG | ACTACATTCA | CCCTGTGTGT | CTGCCCGACA | GGGAGACGGC | AGCCAGCTTG | 1500 |
| CTCCAGGCTG | GATACAAGGG | GCGGGTGACA | GGCTGGGGCA | ACCTGAAGGA | GACGTGGACA | 1560 |
| GCCAACGTTG | GTAAGGGGCA | GCCCAGTGTC | CTGCAGGTGG | TGAACCTGCC | CATTGTGGAG | 1620 |
| CGGCCGGTCT | GCAAGGACTC | CACCCGGATC | CGCATCACTG | ACAACATGTT | CTGTGCTGGT | 1680 |
| TACAAGCCTG | ATGAAGGGAA | ACGAGGGGAT | GCCTGTGAAG | GTGACAGTGG | GGGACCCTTT | 1740 |
| GTCATGAAGA | GCCCCTTTAA | CAACCGCTGG | TATCAAATGG | GCATCGTCTC | ATGGGGTGAA | 1800 |
| GGCTGTGACC | GGGATGGGAA | ATATGGCTTC | TACACACATG | TGTTCCGCCT | GAAGAAGTGG | 1860 |
| ATACAGAAGG | TCATTGATCA | GTTTGGAGAG | TAGGGGGCCA | CTCATATTCT | GGGCTCCTGG | 1920 |
| AACCAATCCC | GTGAAAGAAT | TATTTTTGTG | TTTCTAAAAC | TAGAATTCGG | ATTCGATATC | 1980 |

AAGCTTAG 1988

( 2 ) INFORMATION FOR SEQ ID NO:16:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: odN1

( x i ) SEQUENCE DESCRIPTION: SEQ ID NO:16:

GGCCAGGCCT TTTAAATTAA GATATC 26

( 2 ) INFORMATION FOR SEQ ID NO:17:

( i ) SEQUENCE CHARACTERISTICS:
        ( A ) LENGTH: 111 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: pN2gpt-GPg (Fig. 5.2)

( x i ) SEQUENCE DESCRIPTION: SEQ ID NO:17:

TTTTTGGCAT ATAAATCGTT CCAGTCCCAA AATGTAATTG GACGGGAGAC AGAGTGACGC 60
ACGCGGCCGC TCTAGAACTA GTGGATCCCC CAACGAATTC CATGGCCCGG G 111

( 2 ) INFORMATION FOR SEQ ID NO:18:

( i ) SEQUENCE CHARACTERISTICS:
        ( A ) LENGTH: 2296 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: pN2gpt-LPg (Fig. 5.3)

( x i ) SEQUENCE DESCRIPTION: SEQ ID NO:18:

ATAAATCGTT AACGAATTCC ATGGAACATA AGGAAGTGGT TCTTCTACTT CTTTTATTTC 60
TGAAATCAGG TCAAGGAAAA GTGTATCTCT CAGAGTGCAA GACTGGGAAT GGAAAGAACT 120
ACAGAGGGAC GATGTCCAAA ACAAAAAATG GCATCACCTG TCAAAATGG AGTTCCACTT 180
CTCCCCACAG ACCTAGATTC TCACCTGCTA CACACCCCTC AGAGGGACTG GAGGAGAACT 240
ACTGCAGGAA TCCAGACAAC GATCCGCAGG GGCCCTGGTG CTATACTACT GATCCAGAAA 300
AGAGATATGA CTACTGCGAC ATTCTTGAGT GTGAAGAGGA ATGTATGCAT TGCAGTGGAG 360
AAAACTATGA CGGCAAAATT TCCAAGACCA TGTCTGGACT GGAATGCCAG GCCTGGGACT 420
CTCAGAGCCC ACACGCTCAT GGATACATTC CTTCCAAATT TCCAAACAAG AACCTGAAGA 480
AGAATTACTG TCGTAACCCC GATAGGGAGC TGCGGCCTTG GTGTTTCACC ACCGACCCCA 540
ACAAGCGCTG GGAACTTTGC GACATCCCCC GCTGCACAAC ACCTCCACCA TCTTCTGGTC 600
CCACCTACCA GTGTCTGAAG GGAACAGGTG AAAACTATCG CGGGAATGTG GCTGTTACCG 660
TTTCCGGGCA CACCTGTCAG CACTGGAGTG CACAGACCCC TCACACACAT AACAGGACAC 720
CAGAAAACTT CCCCTGCAAA AATTTGGATG AAAACTACTG CCGCAATCCT GACGGAAAAA 780

| | | | | | |
|---|---|---|---|---|---|
| GGGCCCCATG | GTGCCATACA | ACCAACAGCC | AAGTGCGGTG | GGAGTACTGT | AAGATACCGT | 840 |
| CCTGTGACTC | CTCCCCAGTA | TCCACGGAAC | AATTGGCTCC | CACAGCACCA | CCTGAGCTAA | 900 |
| CCCCTGTGGT | CCAGGACTGC | TACCACGGTG | ATGGACAGAG | CTACCGAGGC | ACATCCTCCA | 960 |
| CCACCACCAC | AGGAAAGAAG | TGTCAGTCTT | GGTCATCTAT | GACACCACAC | CGGCACCAGA | 1020 |
| AGACCCCAGA | AAACTACCCA | AATGCTGGCC | TGACAATGAA | CTACTGCAGG | AATCCAGATG | 1080 |
| CCGATAAAGG | CCCCTGGTGT | TTTACCACAG | ACCCCAGCGT | CAGGTGGGAG | TACTGCAACC | 1140 |
| TGAAAAAATG | CTCAGGAACA | GAAGCGAGTG | TTGTAGCACC | TCCGCCTGTT | GTCCTGCTTC | 1200 |
| CAGATGTAGA | GACTCCTTCC | GAAGAAGACT | GTATGTTTGG | GAATGGGAAA | GGATACCGAG | 1260 |
| GCAAGAGGGC | GACCACTGTT | ACTGGGACGC | CATGCCAGGA | CTGGGCTGCC | AGGAGCCCC | 1320 |
| ATAGACACAG | CATTTTCACT | CCAGAGACAA | ATCCACGGGC | GGGTCTGGAA | AAAAATTACT | 1380 |
| GCCGTAACCC | TGATGGTGAT | GTAGGTGGTC | CCTGGTGCTA | CACGACAAAT | CCAAGAAAAC | 1440 |
| TTTACGACTA | CTGTGATGTC | CCTCAGTGTG | CGGCCCCTTC | ATTTGATTGT | GGGAAGCCTC | 1500 |
| AAGTGGAGCC | GAAGAAATGT | CCTGGAAGGG | TTGTGGGGGG | GTGTGTGGCC | CACCCACATT | 1560 |
| CCTGGCCCTG | GCAAGTCAGT | CTTAGAACAA | GGTTTGGAAT | GCACTTCTGT | GGAGGCACCT | 1620 |
| TGATATCCCC | AGAGTGGGTG | TTGACTGCTG | CCCACTGCTT | GGAGAAGTCC | CCAAGGCCTT | 1680 |
| CATCCTACAA | GGTCATCCTG | GGTGCACACC | AAGAAGTGAA | TCTCGAACCG | CATGTTCAGG | 1740 |
| AAATAGAAGT | GTCTAGGCTG | TTCTTGGAGC | CCACACGAAA | AGATATTGCC | TTGCTAAAGC | 1800 |
| TAAGCAGTCC | TGCCGTCATC | ACTGACAAAG | TAATCCCAGC | TTGTCTGCCA | TCCCCAAATT | 1860 |
| ATGTGGTCGC | TGACCGGACC | GAATGTTTCA | TCACTGGCTG | GGGAGAAACC | CAAGGTACTT | 1920 |
| TTGGAGCTGG | CCTTCTCAAG | GAAGCCCAGC | TCCCTGTGAT | TGAGAATAAA | GTGTGCAATC | 1980 |
| GCTATGAGTT | TCTGAATGGA | AGAGTCCAAT | CCACCGAACT | CTGTGCTGGG | CATTTGGCCG | 2040 |
| GAGGCACTGA | CAGTTGCCAG | GGTGACAGTG | GAGGTCCTCT | GGTTTGCTTC | GAGAAGGACA | 2100 |
| AATACATTTT | ACAAGGAGTC | ACTTCTTGGG | GTCTTGGCTG | TGCACGCCCC | AATAAGCCTG | 2160 |
| GTGTCTATGT | TCGTGTTTCA | AGGTTTGTTA | CTTGGATTGA | GGGAGTGATG | AGAAATAATT | 2220 |
| AATTGGACGG | GAGACAGAGT | GACGCACGCG | GCCGCTCTAG | AACTAGTGGA | TCCCCCGGGA | 2280 |
| AGGCCTCGGA | CCGGGC | | | | | 2296 |

(2) INFORMATION FOR SEQ ID NO:19:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: pN2gpt-gp160 (Fig. 5.4)

(xi) SEQUENCE DESCRIPTION: SEQ ID NO:19:

| | | | | | |
|---|---|---|---|---|---|
| TTTTTGGCAT | ATAAATCGTT | ATCCACCATG | TAAGATAACG | AATTCCATGG | CCCGGG | 56 |

(2) INFORMATION FOR SEQ ID NO:20:

(i) SEQUENCE CHARACTERISTICS:
        (A) LENGTH: 331 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:

( B ) CLONE: pvWF (Fig. 6.2)

( x i ) SEQUENCE DESCRIPTION: SEQ ID NO:20:

| | | | | | |
|---|---|---|---|---|---|
| TTTTTTTGG | CATATAAATC | GCGGCCGCGG | GTGGTTGGTG | GATGTCACAG | CTTGGGCTTT | 60 |
| ATCTCCCCCA | GCAGTGGGAT | TCCACAGCCC | CTGGGCTACA | TAACAGCAAG | ACAGTCCGGA | 120 |
| GCTGTAGCAG | ACCTGATTGA | GCCTTTGCAG | CAGCTGAGAG | CATGGCCTAG | GGTGGGCGGC | 180 |
| ACCATTGTCC | AGCAGCTGAG | TTTCCCAGGG | ACCTTGGAGA | TAGCCGCAGC | CCTCATTTGC | 240 |
| AGGGGAAGAT | GTGAGGCTGC | TGCAGCTGCA | TGGGTGCCTG | CTGCTGCCTG | CCTTGGCCTG | 300 |
| ATGGCGGCCG | CCCGGGTTTT | TATCTCGAGA | C | | | 331 |

( 2 ) INFORMATION FOR SEQ ID NO:21:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: pEcoK-dhr (Fig. 8.1)

( x i ) SEQUENCE DESCRIPTION: SEQ ID NO:21:

| | | | | |
|---|---|---|---|---|
| ATTAGCGTCT | CGTTTCAGAC | GCGGCCGCGG | TAATTAGATT | CTCCCACATT | 50 |

( 2 ) INFORMATION FOR SEQ ID NO:22:

( i ) SEQUENCE CHARACTERISTICS:
        ( A ) LENGTH: 1209 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: pdhr-gpt (Fig. 8.1)

( x i ) SEQUENCE DESCRIPTION: SEQ ID NO:22:

| | | | | | |
|---|---|---|---|---|---|
| ATTAGCGTCT | CGTTTCAGAC | GCGGCCGCTC | TAGAACTAGT | GGATCCCCCA | ACTTAAGGGT | 60 |
| ACCGCCTCGA | CATCTATATA | CTATATAGTA | ATACCAATAC | TCAAGACTAC | GAAACTGATA | 120 |
| CAATCTCTTA | TCATGTGGGT | AATGTTCTCG | ATGTCGAATA | GCCATATGCC | GGTAGTTGCG | 180 |
| ATATACATAA | ACTGATCACT | AATTCCAAAC | CCACCCGCTT | TTTATAGTAA | GTTTTTCACC | 240 |
| CATAAATAAT | AAATACAATA | ATTAATTTCT | CGTAAAAGTA | GAAAATATAT | TCTAATTTAT | 300 |
| TGCACGGTAA | GGAAGTAGAA | TCATAAAGAA | CAGTGACGGA | TGATCCCCAA | GCTTGGACAC | 360 |
| AAGACAGGCT | TGCGAGATAT | GTTTGAGAAT | ACCACTTTAT | CCCGCGTCAG | GGAGAGGCAG | 420 |
| TGCGTAAAAA | GACGCGGACT | CATGTGAAAT | ACTGGTTTTT | AGTGCGCCAG | ATCTCTATAA | 480 |
| TCTCGCGCAA | CCTATTTTCC | CCTCGAACAC | TTTTTAAGCC | GTAGATAAAC | AGGCTGGGAC | 540 |
| ACTTCACATG | AGCGAAAAAT | ACATCGTCAC | CTGGGACATG | TTGCAGATCC | ATGCACGTAA | 600 |
| ACTCGCAAGC | CGACTGATGC | CTTCTGAACA | ATGGAAAGGC | ATTATTGCCG | TAAGCCGTGG | 660 |
| CGGTCTGGTA | CCGGGTGCGT | TACTGGCGCG | TGAACTGGGT | ATTCGTCATG | TCGATACCGT | 720 |
| TTGTATTTCC | AGCTACGATC | ACGACAACCA | GCGCGAGCTT | AAAGTGCTGA | AACGCGCAGA | 780 |
| AGGCGATGGC | GAAGGCTTCA | TCGTTATTGA | TGACCTGGTG | GATACCGGTG | GTACTGCGGT | 840 |
| TGCGATTCGT | GAAATGTATC | CAAAAGCGCA | CTTTGTCACC | ATCTTCGCAA | AACCGGCTGG | 900 |
| TCGTCCGCTG | GTTGATGACT | ATGTTGTTGA | TATCCCGCAA | GATACCTGGA | TTGAACAGCC | 960 |

```
GTGGGATATG  GGCGTCGTAT  TCGTCCCGCC  AATCTCCGGT  CGCTAATCTT  TTCAACGCCT      1020

GGCACTGCCG  GGCGTTGTTC  TTTTTAACTT  CAGGCGGGTT  ACAATAGTTT  CCAGTAAGTA      1080

TTCTGGAGGC  TGCATCCATG  ACACAGGCAA  ACCTGAGCGA  AACCCTGTTC  AAACCCCGCT      1140

TTGGGCTGCA  GGAATTCGAT  ATCAAGCTTA  TCGATACCGT  CGCGGCCGCG  GTAATTAGAT      1200

TCTCCCACA                                                                  1209
```

(2) INFORMATION FOR SEQ ID NO:23:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: odN2

(xi) SEQUENCE DESCRIPTION: SEQ ID NO:23:

```
GGCCGATATC  TTAATTTAAA  AGGCCT                                             26
```

(2) INFORMATION FOR SEQ ID NO:24:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: odN3

(xi) SEQUENCE DESCRIPTION: SEQ ID NO:24:

```
CCAATGTTAC  GTGGGTTACA  TCAG                                               24
```

(2) INFORMATION FOR SEQ ID NO:25:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: I-SceI linker 1

(xi) SEQUENCE DESCRIPTION: SEQ ID NO:25:

```
TAGGGATAAC  AGGGTAAT                                                       18
```

(2) INFORMATION FOR SEQ ID NO:26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: I-SceI linker 2

(xi) SEQUENCE DESCRIPTION: SEQ ID NO:26:

```
ATTACCCTGT  TATCCCTA                                                       18
```

( 2 ) INFORMATION FOR SEQ ID NO:27:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: odS2

( x i ) SEQUENCE DESCRIPTION: SEQ ID NO:27:

GTATAAAGTC CGACTATTGT TCT                       23

( 2 ) INFORMATION FOR SEQ ID NO:28:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: odS3

( x i ) SEQUENCE DESCRIPTION: SEQ ID NO:28:

TCTGAGGCCT AATAGACCTC TGTACA                 26

( 2 ) INFORMATION FOR SEQ ID NO:29:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: SfiI(1)

( x i ) SEQUENCE DESCRIPTION: SEQ ID NO:29:

GGCCGGCTAG GCC                                   13

( 2 ) INFORMATION FOR SEQ ID NO:30:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: SfiI(2)

( x i ) SEQUENCE DESCRIPTION: SEQ ID NO:30:

GGCCATATAG GCC                                   13

( 2 ) INFORMATION FOR SEQ ID NO:31:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: DNA (genomic)

(v i i) IMMEDIATE SOURCE:
   (B) CLONE: odTK1

(x i) SEQUENCE DESCRIPTION: SEQ ID NO:31:

GAGTCGATGT AACACTTTCT ACAGGATCCG TTAACTCGCG AGAATTCCAT CACGTTAGAA    60

AATGCG    66

(2) INFORMATION FOR SEQ ID NO:32:

(i) SEQUENCE CHARACTERISTICS:
       (A) LENGTH: 79 base pairs
       (B) TYPE: nucleic acid
       (C) STRANDEDNESS: single
       (D) TOPOLOGY: linear (i i) MOLECULE TYPE: DNA (genomic)

(v i i) IMMEDIATE SOURCE:
       (B) CLONE: P-J(1)

(x i) SEQUENCE DESCRIPTION: SEQ ID NO:32:

GATCCGGCCG GCTAGGCCGC GGCCGCCCGG GTTTTTATCT CGAGACAAAA AGACGGACCG    60

GGCCCGGCCA TATAGGCCC    79

(2) INFORMATION FOR SEQ ID NO:33:

(i) SEQUENCE CHARACTERISTICS:
       (A) LENGTH: 79 base pairs
       (B) TYPE: nucleic acid
       (C) STRANDEDNESS: single
       (D) TOPOLOGY: linear (i i) MOLECULE TYPE: DNA (genomic)

(v i i) IMMEDIATE SOURCE:
       (B) CLONE: P-J(2)

(x i) SEQUENCE DESCRIPTION: SEQ ID NO:33:

AATTGGGCCT ATATGGCCGG GCCCGGTCCG TCTTTTTGTC TCGAGATAAA AACCCGGGCG    60

GCCGCGGCCT AGCCGGCCG    79

(2) INFORMATION FOR SEQ ID NO:34:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (i i) MOLECULE TYPE: DNA (genomic)

(v i i) IMMEDIATE SOURCE:
       (B) CLONE: odTK2

(x i) SEQUENCE DESCRIPTION: SEQ ID NO:34:

AGAAGCCGTG GGTCATTG    18

(2) INFORMATION FOR SEQ ID NO:35:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (i i) MOLECULE TYPE: DNA (genomic)

(v i i) IMMEDIATE SOURCE:
       (B) CLONE: odTK3

( x i ) SEQUENCE DESCRIPTION: SEQ ID NO:35:

TACCGTGTCG CTGTAACTTA C                                                                                        21

( 2 ) INFORMATION FOR SEQ ID NO:36:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: P-A(0.1)

( x i ) SEQUENCE DESCRIPTION: SEQ ID NO:36:

AGGCCGGCTA GGCCGCGGCC GCCCGGGTTT TTATCTCGAG ACAAAAAGAC GGACCGGGCC                                              60

CGGCCATATA GGCCA                                                                                              75

( 2 ) INFORMATION FOR SEQ ID NO:37:

( i ) SEQUENCE CHARACTERISTICS:
        ( A ) LENGTH: 83 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: P-A(0.2)

( x i ) SEQUENCE DESCRIPTION: SEQ ID NO:37:

GTACTGGCCT ATATGGCCGG GCCCGGTCCG TCTTTTTGTC TCGAGATAAA AACCCGGGCG                                              60

GCCGCGGCCT AGCCGGCCTA GCT                                                                                     83

( 2 ) INFORMATION FOR SEQ ID NO:38:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: P-artP(11)

( x i ) SEQUENCE DESCRIPTION: SEQ ID NO:38:

GGCCACGTTT TTATGGGAAG CTTTTTTTTT TTTTTTTTT TGGCATATAA ATCGC                                                    55

( 2 ) INFORMATION FOR SEQ ID NO:39:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: P-artP(12)

( x i ) SEQUENCE DESCRIPTION: SEQ ID NO:39:

GGCCGCGATT TATATGCCAA AAAAAAAAA AAAAAAAGC TTCCCATAAA AACGT                                                     55

( 2 ) INFORMATION FOR SEQ ID NO:40:

-continued ( i ) SEQUENCE CHARACTERISTICS:
( A ) LENGTH: 93 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: P-artP(8)

( x i ) SEQUENCE DESCRIPTION: SEQ ID NO:40:

CGCTGGCCTA TATGGCCGGG CCCGGTCCGA GGCCTTCCCG GGCCATGGAA TTCATTTATA 60

TGCCAAAAAA AAAAAAAAAA AAAAGCTTCT GCA 93

( 2 ) INFORMATION FOR SEQ ID NO:41:

( i ) SEQUENCE CHARACTERISTICS:
( A ) LENGTH: 97 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: P-artP(10)

( x i ) SEQUENCE DESCRIPTION: SEQ ID NO:41:

CGCTGGCCTA TATGGCCGGG CGTCCGAGGC CTTCCCGGGC CATGGAATTC GTTAACGATT 60

TATATGCCAA AAAAAAAAAA AAAAAAAAGC TTCTGCA 97

( 2 ) INFORMATION FOR SEQ ID NO:42:

( i ) SEQUENCE CHARACTERISTICS:
( A ) LENGTH: 50 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: oligonucleotide P- hr(3)

( x i ) SEQUENCE DESCRIPTION: SEQ ID NO:42:

ATTAGCGTCT CGTTTCAGAC GCGGCCGCGG TAATTAGATT CTCCCACATT 50

DIRECT MOLECULAR CLONING OF A MODIFIED POXVIRUS GENOME

BACKGROUND OF THE INVENTION

The present invention relates to modified genomes of eukaryotic DNA viruses which replicate in the cytoplasm of a host cell, such as poxviruses and iridoviruses. More specifically, the invention relates to direct molecular cloning of a modified cytoplasmic DNA virus genome that is produced by modifying under extracellular conditions a purified DNA molecule comprising a cytoplasmic DNA virus genome. The modified DNA molecule is then packaged into infectious virions in a cell infected with a helper cytoplasmic DNA virus. In a preferred embodiment of the present invention, a foreign DNA fragment comprising a desired gene is inserted directly into a genomic poxvirus DNA at a restriction endonuclease cleavage site that is unique in the viral genome, and the modified viral DNA is packaged into virions by transfection into cells infected with a helper poxvirus.

Cytoplasmic DNA viruses of eukaryotes include diverse poxviruses and iridoviruses found in vertebrates and insects. Poxviruses having recombinant genomes have been used for expression of a variety of inserted genes. Such poxviruses can be used to produce biologically active polypeptides in cell cultures, for instance, and to deliver vaccine antigens directly to an animal or a human immune system. Construction of recombinant iridovirus genomes for expression of foreign genes appears not to be documented in the literature pertaining to genetic engineering.

Conventional techniques for construction of C recombinant poxvirus genomes comprised of foreign genes rely in part on in vivo (intracellular) recombination. The use of intracellular recombination was first described as a process of "marker rescue" with subgenomic fragments of viral DNA by Sam & Dumbell, *Ann. Virol.* (Institut Pasteur) 132E: 135 (1981). These authors demonstrated that a temperature-sensitive vaccinia virus mutant could be "rescued" by intracellular recombination with a subgenomic DNA fragment of a rabbit poxvirus. The methods they used for intracellular recombination are still used today.

Construction of recombinant vaccinia viruses comprised of non-poxvirus ("foreign") genes was later described by Panicali & Paoletti, *Proc. Nat'l Acad. Sci. U.S.A.* 79:4927–4931 (1982); Mackett, et al., Proc. Nat'l Acad. Sci. U.S.A. 79: 7415–7419 (1982); and U.S. Pat. No. 4,769,330. More specifically, the extant technology for producing recombinant poxviruses involves two steps. First, a DNA fragment is prepared that has regions of homology to the poxvirus genome surrounding a foreign gene. Alternatively, an "insertion" plasmid is constructed by in vitro (extracellular) recombination of a foreign gene with a plasmid. This plasmid comprises short viral DNA sequences that are homologous to the region of the poxvirus genome where gene insertion is ultimately desired. The foreign gene is inserted into the plasmid at a site flanked by the viral DNA sequences and, typically, downstream of a poxvirus promoter that will control transcription of the inserted gene. In the second step, the insertion plasmid is introduced into host cells infected with the target poxvirus. The gene is then indirectly inserted into the poxvirus genome by intracellular recombination between homologous viral sequences in the poxvirus genome and the portion of the plasmid including the foreign gene. The resulting recombinant genome then replicates, producing infectious poxvirus.

Thus, insertion of each particular gene into a poxvirus genome has heretofore required a distinct plasmid comprised of the gene flanked viral sequences selected for a desired insertion location. A difficulty with this approach is that a new insertion plasmid is required for each recombinant poxvirus. Each plasmid must be constructed by extracellular recombinant DNA methods, amplified in a bacterial cell, and then laboriously isolated and rigorously purified before addition to a poxvirus-infected host cell.

Another problem with extant methodology in this regard is a low yield of recombinant genomes, which can necessitate screening hundreds of individual viruses to find a single desired recombinant. The poor yield is a function of the low frequency of individual intracellular recombination events, compounded by the requirement for multiple events of this sort to achieve integration of the insertion plasmid into a viral genome. As a result, the majority of viral genomes produced by intracellular recombination methods are parental genomes that lack a foreign gene. It is often necessary, therefore, to introduce a selective marker gene into a poxvirus genome, along with any other desired sequence, to permit ready detection of the required rare recombinants without the need of characterizing isolated DNAs from numerous individual virus clones.

Purified DNAs of eukaryotic cytoplasmic DNA viruses are incapable of replicating when introduced into susceptible host cells using methods that initiate infections with vital DNAs that replicate in the nucleus. This lack of infectivity of DNAs of cytoplasmic DNA viruses results from the fact that viral transcription must be initiated in infected cells by a virus-specific RNA polymerase which is normally provided inside infecting virions.

"Reactivation" of poxvirus DNA, in which genomic DNA inside an inactivated, noninfectious poxvirus particle was packaged into infectious virions by coinfection with a viable helper poxvirus, has been known for decades. See, for instance, Fenner & Woodroofe, *Virology* 11: 185–201 (1960). In 1981 Sam and Dumbell demonstrated that isolated, noninfectious genomic DNA of a first poxvirus could be packaged into infectious poxvirus virions in cells infected with a second, genetically distinct poxvirus. Sam & Dumbell, *Ann. Virol.* (Institut Pasteur) 132E: 135 (1981). This packaging of naked poxvirus DNA was first demonstrated by transfection of unmodified DNA comprising a first wildtype orthopoxvirus genome, isolated from virions or infected cells, into cells infected with a second naturally occurring orthopoxvirus genome. However, heterologous packaging, packaging of DNA from one poxvirus genus (orthopox, for example) by viable virions of another genus (e.g., avipox), has not been demonstrated yet.

The use of intracellular recombination for constructing a recombinant poxvirus genome expressing non-poxvirus genes was reported shortly after Sam & Dumbell first reported intracellular packaging of naked poxvirus DNA into poxvirus virions and marker rescue with DNA fragments by intracellular recombination. See Panicali & Paoletti, 1982; Mackett, et al., 1982. The relevant literature of the succeeding decade, however, appears not to document the direct molecular cloning, i.e., construction solely by extracellular genetic engineering, of a modified genome of any eukaryotic cytoplasmic DNA virus, particularly a poxvirus. The literature does not even evidence widespread recognition of any advantage possibly realized from such a direct cloning approach. To the contrary, an authoritative treatise has stated that direct molecular cloning is not practical in the context of genetic engineering of poxviruses because poxvirus DNA is not infectious. F. FENNER, R. WITTEK & K. R. DUMBELL, THE POXVIRUSES (Academic Press, 1989). Others working in the area have likewise discounted endonucleolytic cleavage and religation of poxvirus DNAs, even while recognizing a potential for rescue by infectious virus of isolated DNA comprising a recombinant poxvirus genome. See, for example, Mackett & Smith, *J. Gen. Virol.* 67: 2067–2082 (1986). Moreover, recent reviews propound the thesis that the only way feasible to construct a recombinant poxvirus genome is by methods requiring intracellular recombination. See Miner & Hruby, TIBTECH 8:20–25 (1990), and Moss & Flexner, *Ann. Rev. Immunol.* 5:305–324 (1987).

SUMMARY OF THE INVENTION

It is therefore an object of the present invention to provide a method for constructing modified genomes of eukaryotic cytoplasmic DNA viruses, particularly of poxviruses, which overcomes the aforementioned limitations associated with conventional techniques based on intracellular recombination.

It is another object of the present invention to provide cytoplasmic DNA virus genome-construction techniques that produce substantially higher yields of recombinants than existing methodology.

It is a further object of this invention to provide methods for modifying a genome of a cytoplasmic DNA virus by direct modification of genomic viral DNA and intracellular packaging of the modified viral DNA into virions with the aid of helper virus functions.

It is another object of this invention to provide methods for construction of a genome of a cytoplasmic DNA virus that produce in one recombination reaction step modified genomes having a foreign DNA segment inserted in each of the two possible orientations and modified genomes having multiple insertions of a foreign DNA segment.

It is still another object of this invention to provide modified DNA molecules suitable for direct molecular cloning of foreign genes in a modified cytoplasmic DNA virus genome, comprising two portions of a genomic viral DNA produced by cleavage with a sequence-specific endonuclease at a site that is unique in the viral genome.

It is yet a further object of this invention to provide a cytoplasmic DNA virus, particularly a poxvirus, having a modified genome comprised of a foreign DNA inserted into a unique cleavage site for a sequence-specific endonuclease.

It is another object of this invention to provide plasmids which facilitate construction and transfer of gene cassettes into a cytoplasmic DNA virus, particularly a poxvirus, using direct molecular cloning.

In accomplishing these and other objects, there has been provided, in accordance with one aspect of the present invention, a method for producing a modified eukaryotic cytoplasmic DNA virus by direct molecular cloning of a modified DNA molecule comprising a modified cytoplasmic DNA virus genome. The inventive method comprises the steps of (I) modifying under extracellular conditions a purified DNA molecule comprising a first cytoplasmic DNA virus genome to produce a modified DNA molecule comprising the modified viral genome; (II) introducing the modified DNA molecule into a first host cell which packages the modified DNA molecule into infectious virions; and (III) recovering from the first host cell infectious virions comprised of the modified viral genome.

According to one embodiment of this method, the step of modifying the DNA molecule under extracellular conditions comprises a step of cleaving the DNA molecule with a sequence-specific endonuclease. According to another embodiment, the step of modifying the DNA molecule comprises a step of inserting a first DNA sequence into the first viral genome. Advantageously, this first DNA sequence is inserted into the first genome at a cleavage site for a sequence-specific endonuclease. It should be noted that where a particular sequence-specific endonuclease, such as a bacterial restriction enzyme, is described herein by name, that name also signifies any isoschizomer of the named nuclease.

Optionally, the step of modifying the DNA molecule according to this method also comprises a step of using a phosphatase to remove a phosphate moiety from an end of a DNA segment that is produced by cleaving the DNA molecule with a sequence-specific endonuclease.

In some embodiments of this method, the first viral genome is a vaccinia virus genome and the unique site is a cleavage site for the bacterial restriction endonuclease NotI or for the bacterial restriction endonuclease SmaI. The first genome also may comprise a second DNA sequence not naturally occurring in a eukaryotic cytoplasmic DNA virus genome where that second DNA sequence is comprised of the unique cleavage site. For instance, the first genome may be a fowlpox virus genome comprising a sequence of an *Escherichia coli* β-galactosidase gene and the unique site is a cleavage site for the bacterial restriction endonuclease NotI that is located in that gene.

In other forms of this method, the first DNA sequence is inserted into the first viral genome between a first cleavage site for a first sequence-specific endonuclease and a second cleavage site for a second sequence-specific endonuclease. Optionally, each of the first and second cleavage sites is unique in the first viral genome.

According to other embodiments of the method of this invention, at least a portion of the first DNA sequence which is inserted into the first genome is under transcriptional control of a promoter. This promoter may be located in the first DNA sequence that is inserted into the first viral genome. Alternatively, the promoter is located in the modified viral genome upstream of the first DNA sequence that is inserted into the first genome. In some cases, the promoter is utilized by an RNA polymerase encoded by the modified viral genome. This promoter may also be suitable for initiation of transcription by an RNA polymerase of the eukaryotic cytoplasmic DNA virus to be modified. In certain methods, the promoter comprises a modification of a naturally occurring promoter of the eukaryotic cytoplasmic DNA virus.

The step of modifying the DNA molecule according to the method of this invention may comprise a step of deleting a DNA sequence from the first genome. Alternatively, this step comprises a step of substituting a DNA sequence of the first genome.

The method of modifying a first viral genome may also comprise a step of infecting the first host cell with a second eukaryotic cytoplasmic DNA virus comprising a second genome which is expressed to package the modified viral genome into infectious virions. Advantageously, the step of introducing the modified DNA molecule into the first host cell is carried out about one hour after the step of infecting the first host cell with the second eukaryotic cytoplasmic DNA virus.

In one variation of this method, the first host cell is selected such that expression of the second genome in the first host cell does not produce infectious virions comprised of the second viral genome. For instance, where the modified viral genome is a modified vaccinia virus genome and the second genome is a fowlpox virus genome, the selected first host cell is a mammalian cell.

In some forms of the method of modifying a viral genome, the step of recovering infectious virions comprised of the modified viral genome comprises a step of infecting a second host cell with infectious virions produced by the first host cell. This is done under conditions such that expression of the second genome in the second host cell does not produce infectious virions comprised of the second genome. For instance, when the modified viral genome is a modified vaccinia virus genome, the second genome may be a fowlpox virus genome, and the second host cell is a mammalian cell. Alternatively, the modified viral genome comprises a functional host range gene required to produce infectious virions in the second host cell and the second genome lacks that functional host range gene. This is illustrated by the case where the modified viral genome is a modified vaccinia virus genome comprising a functional host range gene required to produce infectious virions in a human cell and the second host cell is a human cell.

In other forms of this method, the modified viral genome comprises a selective marker gene, the second genome lacks that selective marker gene, and the step of infecting the second host cell is carried out under conditions that select for a genome expressing that selective marker gene. Advantageously, expression of the selective marker gene in the second host cell confers on the second host cell resistance to a cytotoxic drug which is present during infection at a level sufficient to select for a genome expressing the selective marker gene.

According to another aspect of the present invention, there is provided a modified eukaryotic cytoplasmic DNA virus produced by direct molecular cloning of a modified viral genome according to methods summarized hereinabove.

Yet another aspect of the present invention relates to a modified eukaryotic cytoplasmic DNA virus comprised of a modified viral genome, wherein that modified viral genome comprises: (I) a first genome of a first eukaryotic cytoplasmic DNA virus. This first genome is comprised of a cleavage site for a sequence-specific endonuclease and this cleavage site is a unique site in the first genome. The modified genome further comprises (II) a first DNA sequence inserted into the unique site in the first genome.

According to a major embodiment of this aspect of the invention, the first DNA sequence is not naturally occurring in a genome of a eukaryotic cytoplasmic DNA virus. In some preferred cases, the first genome is a vaccinia virus genome and the unique site is a cleavage site for a bacterial restriction endonuclease selected from the group consisting of NotI and SmaI.

The first genome may comprise a second DNA sequence not naturally occurring in a genome of a eukaryotic cytoplasmic DNA virus and that second DNA sequence is comprised of the unique cleavage site. In one example, the first genome is a fowlpox virus genome comprising a second DNA sequence of an *Escherichia coli* $\beta$-galactosidase gene and the unique site in that gene is a cleavage site for the bacterial restriction endonuclease NotI.

In some modified viruses of this invention, at least a portion of said first DNA sequence that is inserted into the unique site is under transcriptional control of a promoter. This promoter is located in the first DNA sequence that is inserted into the first genome. In some cases the first genome is a poxvirus genome and the promoter comprises a poxvirus promoter, either a naturally occurring poxvirus promoter or a modification thereof.

Yet another aspect of the present invention relates to a modified eukaryotic cytoplasmic DNA virus comprised of a modified viral genome in which the modified viral genome comprises (I) a first genome of a first eukaryotic cytoplasmic DNA virus. This first genome is comprised of a first cleavage site for a first sequence-specific endonuclease and a second cleavage site for a second sequence-specific endonuclease. Each of these cleavage sites is a unique site in the first genome.

The modified genome in this modified virus further comprises (II) a first DNA sequence inserted into the first genome between the first unique site and the second unique site. In some forms of this modified virus the first DNA sequence is not naturally occurring in a genome of a eukaryotic cytoplasmic DNA virus. In some cases the first genome comprises a second DNA sequence not naturally occurring in a genome of a eukaryotic cytoplasmic DNA virus and that second DNA sequence is comprised of the first DNA sequence inserted between the first unique site and the second unique site. For an example, this modified virus may comprise a first genome that is a vaccinia virus genome and each of the first unique site and the second unique site is a cleavage site for a bacterial restriction endonuclease selected from the group consisting of NotI, SmaI, ApaI and RsrII.

Yet another modified eukaryotic cytoplasmic DNA virus of the present invention is comprised of a modified viral genome which comprises (I) a first genome of a first eukaryotic cytoplasmic DNA virus. This first genome is comprised of a first DNA sequence and this first DNA sequence is comprised of a cleavage site for a sequence-specific endonuclease that is a unique site in this modified viral genome. This genome of this modified virus further comprises (II) a promoter located such that a DNA sequence inserted into the unique site in the viral genome is under transcriptional control of the promoter. In certain forms, this first DNA sequence lacks a translation start codon between the promoter and the unique insertion site. This first DNA sequence may be one that is not naturally occurring in a genome of a eukaryotic cytoplasmic DNA virus. This modified virus is exemplified by one in which the first genome is a vaccinia virus genome and the first DNA sequence is comprised of a multiple cloning site comprising cleavage sites for the bacterial restriction endonucleases NotI, SmaI, ApaI and RsrII.

Yet another aspect of the present invention relates to a modified eukaryotic cytoplasmic DNA virus of this invention, wherein a first sequence in the modified viral genome (an inserted sequence of interest) is expressed in a host cell resulting in production of a protein.

According to another aspect, the present invention also relates to a DNA molecule comprising a modified viral genome of a modified virus according to the present invention. In particular, some forms of this DNA molecule comprise one end of a modified viral genome of a eukaryotic cytoplasmic DNA virus in which (I) that end of the modified viral genome comprises a DNA sequence not naturally occurring in a genome of a eukaryotic cytoplasmic DNA virus. In this DNA molecule, (II) the modified viral genome is comprised of a cleavage site for a sequence-specific endonuclease that is a unique site in the modified viral genome; and (III) the DNA molecule has a terminus that is homologous to a terminus that is produced by cleaving the unique site in the modified viral genome with the sequence-specific endonuclease.

In some forms of this DNA molecule, the DNA sequence not naturally occurring in a genome of a eukaryotic cytoplasmic DNA virus is comprised of the cleavage site for a sequence-specific endonuclease that is a unique site in the modified viral genome.

Still another aspect of this invention relates to a kit for direct molecular cloning of a modified viral genome of a eukaryotic cytoplasmic DNA virus, comprising: (I) purified DNA molecules according to this invention; (II) a DNA ligase; and (III) solutions of a buffer and reagents suitable for ligation of DNA segments together to produce a modified DNA molecule comprising the modified viral genome. In one form, this kit further comprises a plasmid comprised of a gene expression cassette flanked by sites for cleavage with a sequence-specific endonuclease that are compatible for insertion of that cassette into a unique cleavage site of the modified viral genome encoded by the DNA molecule in the kit. The kit may further comprise a first host cell and a second virus suitable for packaging of the modified viral genome into infectious virions.

According to a further aspect, this invention relates to a plasmid comprising a DNA segment having a cleavage site for the bacterial restriction endonuclease NotI at each end. In this plasmid, this DNA segment comprises a sequence-specific endonuclease cleavage site that is unique in the plasmid. An example of this plasmid as shown in FIG. 1.3, is designated pN2 and comprises the sequence of SEQ. ID. NO. 1. In this plasmid the DNA segment may further comprise a selective marker gene under transcriptional control of a poxvirus promoter. For instance, such plasmids include plasmids designated pN2-gpta comprising the sequence of SEQ. ID. NO. 2, and pN2-gptb comprising the sequence of SEQ. ID. NO. 3.

Another plasmid of the invention contains a DNA segment that further comprises a poxvirus promoter operatively linked to a DNA sequence comprising a restriction endonuclease cleavage site. Thus, a DNA segment inserted into this cleavage site is under transcriptional control of this promoter. Examples are plasmids designated pA1-S2 comprising the sequence of SEQ. ID. NO. 11, and pA2-S2 comprising the sequence of SEQ. ID. NO. 12. An example of such a plasmid which further comprises a selective marker gene under control of a separate poxvirus promoter is plasmid pN2gpt-S4, comprising the sequence of SEQ. ID. NO. 14.

Still another plasmid comprises a segment of a poxvirus genome that comprises a thymidine kinase gene of that poxvirus. This thymidine kinase gene has been modified to prevent expression of active thymidine kinase, as in plasmids designated pHindJ-2 comprising the sequence of SEQ. ID. NO. 4, and pHindJ-3 comprising the sequence of SEQ. ID. NO. 5.

Another plasmid comprises a poxvirus promoter operatively linked to a translational start codon. This start codon is immediately followed by a second restriction endonuclease cleavage site suitably arranged to permit translation of an open reading frame inserted into that second restriction endonuclease cleavage site. Examples of this plasmid include plasmids designated pA1-S1 comprising the sequence of SEQ. ID. NO. 9 and pA2-S1 comprising the sequence of SEQ. ID. NO. 10, and plasmid pN2gpt-S3A comprising the sequence of SEQ. ID. NO. 13.

One particular plasmid of this type further comprises a DNA sequence encoding human prothrombin, where that DNA sequence is operatively linked to the poxvirus promoter and a start codon, as illustrated in FIG. 5.1 by a plasmid designated plasmid pA1S1PT, and comprising the sequence of SEQ. ID. NO. 15.

Another plasmid further comprises a DNA sequence encoding human plasminogen and including a translation start codon, where that DNA sequence is operatively linked to the poxvirus promoter. As shown in FIG. 5.2, this is exemplified by plasmids derived from pN2gpt-S4, such as pN2gpt-GPg, encoding human gluplasminogen and comprising the sequence of SEQ. ID. NO. 17, and pN2gpt-LPg encoding lys-plasminogen and comprising a sequence of SEQ. ID. NO. 18.

Yet another plasmid of this invention, as above, further comprises a DNA sequence encoding human immunodeficiency virus (HIV) gp160, including a translation start codon, operatively linked to the poxvirus promoter, as shown in FIG. 5.4 by plasmid pN2gpt-gp160 comprising the sequence of SEQ. ID. NO. 19. Finally, another plasmid comprises a DNA sequence encoding human von Willebrand factor as shown in FIG. 6.2, an example being designated plasmid pvWF, comprising the sequence of SEQ. ID. NO. 20.

Some plasmids of this invention comprise a sequence-specific endonuclease cleavage site that is unique in the genome of the poxvirus. Examples are shown in FIG. 4.3, including pA0 comprising the sequence of SEQ. ID. NO. 6, pal comprising the sequence of SEQ. ID. NO. 7, and pA2 comprising the sequence of SEQ. ID. NO. 8.

Another plasmid comprises a modified EcoRI K fragment of vaccinia virus DNA from which the K1L host range gene is deleted, as depicted in FIG. 8.1. Two examples are pEcoK-dhr comprising the sequence of SEQ. ID. NO. 21, and pdhr-gpt comprising the sequence of SEQ. ID. NO. 22.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1.1 illustrates expression of marker genes by modified genomes of poxviruses produced by reactivation of naked poxvirus DNA. A silver-stained polyacrylamide gel of proteins produced in culture supernatants of cells infected with packaged viruses (vpPg#1-vpPg#8) and with wildtype (WT) virus controls is shown. The upper arrow points to plasminogen marker band, the lower arrow, to the band of major secreted 35K vaccinia marker protein. Lanes 1 and 9, marker proteins; lanes 2 and 10, human plasminogen standard (10 ng); lane 3, vaccinia recombinant vPgD (source of packaged DNA); lanes 4-7 and 11-14, vpPg#1-8; lanes 8 and 15, wildtype vaccinia (WR WT).

FIG. 1.2 is a schematic diagram illustrating direct molecular cloning of poxvirus genomes comprised of a gene cassette for expression of a marker gene (the E. coli gpt gene) under control of a vaccinia virus promoter.

FIG. 1.3 is a schematic illustration of construction of plasmids (pN2-gpta and pN2-gptb) which are precursors for construction of gene expression cassettes by insertion of a promoter and an open reading frame. Such cassettes are designed for direct molecular transfer into vaccinia virus vectors using a unique insertion site and a selectable marker gene (gpt) driven by a vaccinia virus promoter. MCS=multiple cloning site. P7.5=promoter for vaccinia 7.5K polypeptide gene; P11=promoter for vaccinia 11K polypeptide gene. Arrows indicate the directions of transcription from the promoters.

FIG. 1.4 demonstrates that poxvirus genomes produced by direct molecular cloning contain the gpt marker gene cassette inserted at a unique (NotI) cleavage site, as shown by Southern blot analyses of plaque-purified viral DNAs digested with the HindIII endonuclease using a gpt-gene probe. Lane 1, marker DNAs (HindIII digested phage λ DNA); lanes 2 and 3, wildtype vaccinia virus (WR) DNA cut with HindIII (500 and 100 ng, respectively); lanes 4-9, DNAs of cells infected with plaques designated 2.1.1 through 7.1.1; lanes 10-12, DNAs of cells infected with plaques 10.1.1-12.1.1. Arrows indicate sizes of the restriction fragments of the marker in kilobasepairs.

FIG. 1.5. further illustrates structures of modified poxvirus DNAs using Southern blots of NotI-digested DNAs of cells infected with various isolates and hybridized with a gpt-gene probe. Lane 1, marker DNAs (HindIII digested phage λ DNA); lane 2, vaccinia wildtype (WT) DNA cut with NotI (50 ng); lanes 3-8, DNAs of cells infected with recombinant plaques designated 2.1.1 through 7.1.1; lanes 9-11, DNAs of cells infected with plaques 10.1.1-12.1.1.

FIG. 1.6 shows a comparison of DNAs from wildtype (WT) vaccinia and a modified clone (vp7) using ethidium bromide staining of DNA fragments cleaved with indicated restriction endonucleases and separated on an agarose gel. Lanes 1 and 2, NotI digests of WT and vp7; lanes 3 and 4, HindIII digests of WT and vp7; lanes 5 and 6, HindIII and NotI combined digests of WT and vp7; lanes 7 and 8, PstI digests of WT and vp7; lanes 9 and 10, PstI and NotI combined digests of WT and vp7; lanes 11 and 12, SalI digests of WT and vp7; lane 13, marker DNAs (ligated and HindIII digested phage λ DNA; and phage φX cut with HaeIII). Arrows on the left indicate sizes of fragments (in kilobasepairs) of NotI digest of vaccinia WT; arrows on right, markers. Note that lanes 1 and 2 contain about tenfold less DNA than the other lanes.

FIG. 1.7 illustrates a Southern blot of the gel shown in FIG. 1.6 using a gpt-gene probe. Arrows indicate marker sizes.

FIG. 1.8 presents Southern blot analyses of vaccinia virus DNAs from infected cells digested with NotI and hybridized to a vaccinia virus probe. Lanes 1-4, DNAs of cells infected with plaques designated A1-A4; lanes 5-8, plaques C1-C4; lanes 9-12, plaques E1-E4; lane 13, vaccinia WT DNA; lane 14, DNA of uninfected CV-1 host cells; lane 15, marker DNAs (HindIII digested phage λ DNA; and phage φX cut with HaeIII).

FIG. 1.9 shows a Southern blot of the same samples as in the gel shown in FIG. 1.8 using a gpt-gene probe. Lanes 1-12 as in FIG. 1.8; lane 13, DNA of uninfected CV-1 host cells; lane 14, vaccinia WT DNA; lane 15, marker DNAs (HindIII digested phage λ DNA; and phage φX cut with HaeIII).

FIG. 1.10 shows a Southern blot of the same viral DNAs as in the gel in FIG. 1.8, restricted with PstI, using a gpt-gene probe. Lanes 1-12 as in FIG. 1.8; lane 13, DNA of uninfected CV-1 host cells; lane 14, vaccinia WT DNA; lane 15, marker DNAs (HindIII digested phage λ DNA; and phage φX cut with HaeIII).

FIG. 1.11 outlines a schematic of the predicted structure of the modified PstI "C" fragments of vaccinia virus DNAs with single or double insertions of the gpt-gene cassette. P=PstI and N=NotI cleavage sites. The numbers indicates sizes of respective PstI fragments; bold type numbers indicate fragments expected to hybridize with a gpt-gene probe. Arrows indicate direction of transcription of the gpt-gene (800 bp) by the vaccinia virus promoter (300 bp).

FIG. 2.1 presents analyses of recombinant avipox (fowlpox, FP) genomes by digestion with the restriction endonuclease NotI and separation by FIGE on a 1% agarose gel. Lane 5, marker (phage λ HindIII fragments, uncut phage λ and vaccinia WR); lanes 1 and 2, fowlpox virus HP1.441 DNA, uncut and cut with NotI; lanes 3 and 4, recombinant fowlpox virus f-TK2a DNA, uncut and cut with NotI.

FIG. 2.2 illustrates construction of fowlpox viruses expressing foreign genes by direct molecular cloning. A gene expression cassette, consisting of the E. coli gpt gene controlled by a poxvirus promoter (P) is ligated with the right and left DNA arms (ra and la, respectively) of fowlpox virus (f-TK2a) obtained by cleavage with NotI. Packaging is performed by fowlpox helper virus (strain HP2) in chicken embryo fibroblasts.

FIG. 3.1 illustrates a process for construction of modified poxviruses by extracellular genome engineering and intracellular packaging. A gene cassette consisting of the gpt gene controlled by a vaccinia virus promoter, is ligated with the "right arm" (ra) and the "left arm" (la) of vaccinia virus DNA cleaved at a unique site with the endonuclease SmaI. Packaging is done by the fowlpox helper virus (strain HP1,441) in chicken embryo fibroblasts. P1=promoter of the vaccinia virus gene coding for the 7.5 kDA polypeptide.

FIG. 3.2 demonstrates that engineered vaccinia virus genomes packaged by fowlpox helper virus contain the expected insert at a unique SmaI cleavage site, as determined by Southern blot analyses. Total DNA isolated from infected cells was digested with HindIII, and the blot was hybridized with a gpt-gene probe. Lanes 1-8, DNAs from cells infected with plaques designated F12.2-F12.9; lanes 9-13, plaques F13.1-F13.5; lanes 14 and 15, HindIII-digested DNA isolated from uninfected cells and cells infected with vaccinia (WR wildtype) virus, respectively; lane 16, markers (HindIII-digested phage λ DNA). The DNA in lane 8 does not hybridize because the virus isolate #F12.9 did not replicate.

FIG. 3.3 presents a schematic outline of the expected structures of modified vaccinia virus genomes having a gene cassette inserted into a unique SmaI site, particularly the modified HindIII "A" fragments of viruses with single and double insertions. H=HindIII and S=SmaI restriction endonuclease cleavage sites. Numbers indicate sizes of the HindIII fragments, with those in bold type indicating fragments expected to hybridize with a gpt-gene probe. The gpt gene cassette consists of a vaccinia virus promoter (about 300 bp in size) separated by an internal HindIII site from the gpt sequences (about 800 bp). Arrows indicate the direction of transcription of the gpt-gene.

FIG. 4.1A–4.1C shows a schematic plan for the construction of vaccinia virus vector vdTK having a modified thymidine kinase (tk) gene. WR-WT=wildtype (WT) Western Reserve (WR) strain of vaccinia virus (VV). Panel A shows a method using only direct molecular modification of the vaccinia virus genome, including deletion of undesired NotI and SmaI sites. Panel B outlines an alternative approach for deletion of a NotI site using marker rescue techniques with vaccinia virus and a modified plasmid. Panel C shows an alternative method for deleting the SmaI site by marker rescue.

FIG. 4.2 illustrates construction of the vaccinia virus vector (vdTK) having the thymidine kinase (tk) gene replaced with a multiple cloning site. The arrow indicates the initiation and direction of transcription of the vaccinia virus tk gene (VV-tk) in the HindIII J fragment cloned in plasmid pHindJ-1. The tk gene was replaced, as shown, and the final plasmid pHindJ-3 was used to insert the modified HindIII J fragment into vaccinia virus.

FIG. 4.3 outlines construction of plasmids (pA1 and pA2) which are precursors for construction of gene expression cassettes by insertion of a promoter and an open reading frame. Such cassettes are suitable for direct molecular transfer into vaccinia virus vector vdTK using directional (forced) cloning.

FIG. 4.4 illustrates construction of plasmids (pA1-S1 and pA2-S1) comprised of gene expression cassettes suitable for association of open reading frames with a synthetic poxvirus promoter (S1) and a translation start codon. The cassettes are designed for direct molecular transfer into vaccinia virus vector vdTK by forced cloning. The S1 promoter is present in different orientations in the two plasmids, as indicated by the arrows showing the directions of transcription. The sequence of promotor S1 is set forth as bases 21-293 of SEQ ID NO:9.

FIG. 4.5 outlines the construction of plasmids (pA1-S2 and pA2-S2) comprised of gene expression cassettes suitable for association of open reading frames already having a translation start codon with a synthetic poxvirus promoter (S2), prior to direct molecular transfer into vaccinia virus vector vdTK by forced cloning. The S2 promoter is present in different orientations in the two plasmids, as indicated by the arrows showing the directions of transcription. The sequence of promotor S2 is set forth as bases 21-73 of SEQ ID NO:11.

FIG. 4.6 shows construction of plasmids (pN2gpt-S3A and pN2gpt-S4) comprised of gene expression cassettes suitable for association of an open reading frame, either lacking (S3A) or having (S4) a translation start codon, with a synthetic promoter (S3A or S4, respectively), prior to direct molecular transfer into a unique site in vaccinia virus vector vdTK. Abbreviations as in FIG. 1.3. The sequence of promotor S3A is set forth as bases 21-107 of SEQ ID NO:13. The sequence of promoter S4 is set forth as bases 21-114 of SEQ ID NO:14.

FIG. 5.1 illustrates construction of a gene expression cassette plasmid (pA1S1-PT) for expression of human prothrombin in vaccinia virus vector vdTK. Abbreviations as in FIG. 1.3. Arrows indicate the direction of transcription.

FIG. 5.2 presents construction of a gene expression cassette plasmid (pN2gpt-GPg) for expression of human glu-plasminogen in vaccinia virus vector vdTK. S4 =synthetic poxvirus promoter; other abbreviations as in FIG. 1.3.

FIG. 5.3 shows construction of a gene expression cassette plasmid (pN2gpt-LPg) for expression of human lys-plasminogen in vaccinia virus vector vdTK. Abbreviations as in FIG. 1.3.

FIG. 5.4 outlines construction of a gene expression cassette plasmid (pN2gpt-gp160) for expression of a human virus antigen (HIV gp160) in vaccinia virus vector vdTK. Abbreviations as in FIG. 1.3.

FIG. 5.5 illustrates an approach for screening of modified vaccinia viruses made by direct molecular cloning based on concurrent insertion of a marker gene (the E. coli lacZ gene) which confers a visually distinctive phenotype ("blue" plaque compared to normal "white" plaques of viruses lacking a lacZ gene).

FIG. 6.1 illustrates construction of a vaccinia virus vector (vS4) with a directional master cloning site under control of a strong late vaccinia virus promoter (S4). The sequence of the two strands of the promoter adapter in VS4 are set forth as SEQ ID NO:38 and SEQ ID NO:39.

FIG. 6.2 presents construction of a modified vaccinia virus (vvWF) for expression of von-Willebrand factor by direct molecular insertion of an open reading frame into vaccinia virus vector vS4. vWF=von Willebrand factor cDNA. The arrow indicates the direction of transcription from the S4 promoter.

FIG. 7.1 illustrates the effect of amount of added DNA on packaging of vaccinia virus DNA by fowlpox helper virus in mammalian (CV-1) cells in which fowlpox virus does not completely replicate. Five cultures were infected with fowlpox virus and subsequently transfected with the indicated amounts of vaccinia virus DNA. The first column indicates a culture with no added DNA and no fowlpox virus, and the fifth column, no added DNA but infected with fowlpox virus.

FIG. 8.1 outlines construction of a vaccinia virus (vdhr) suitable for use as a helper virus having host range mutations which prevent replication in some human cell lines. hr-gene=host range gene located in the EcoRI K fragment of vaccinia virus; other abbreviations as in FIG. 1.3.

DETAILED DESCRIPTION OF PREFERRED EMBODIMENTS

The present invention represents the first construction of a modified genome of a eukaryotic cytoplasmic DNA virus, as exemplified by a poxvirus, completely outside the confines of a living cell. This construction was accomplished using an isolated viral genomic DNA that was cleaved by a sequence-specific endonuclease and then religated with foreign DNA. The resulting modified DNA was then packaged into infectious poxvirus virions by transfection into a host cell infected with another poxvirus that served as a helper virus.

The present invention enables diverse strategies for vector development from eukaryotic cytoplasmic DNA viruses which have been applied previously to other DNA viruses to solve various genetic engineering problems. For instance, this direct cloning approach offers the possibility of cloning genes directly in cytoplasmic DNA viruses, such as poxviruses, that cannot be cloned in bacterial systems, either because they are too large for bacterial vectors or are toxic to bacteria or are unstable in bacteria. Direct molecular cloning allows greater precision over construction of engineered viral genomes and under optimum conditions can increase the speed of cloning as well as produce a variety of constructs in a single ligation reaction, having multiple inserts in various orientations, which permits rapid screening for arrangements affording optimal expression of a foreign gene.

As used in the present context, "eukaryotic cytoplasmic DNA virus" includes iridoviruses and poxviruses. "Iridovirus" includes any virus that is classified as a member of the family Iridoviridae, as exemplified by the African swine fever virus as well as certain amphibian and insect viruses.

"Poxvirus" includes any member of the family Poxviridae, including the subfamililes Chordopoxviridae (vertebrate poxviruses) and Entomopoxviridae (insect poxviruses). See, for example, B. Moss in B. N. FIELDS, D. M. KNIPE ET AL. VIROLOGY 2080 (Raven Press, 1990). The chordopoxviruses comprise, inter alia, the following genera from which particular examples are discussed herein, as indicated in parentheses: Orthopoxvirus (vaccinia); Avipoxvirus (fowlpox); Capripoxvirus (sheeppox) Leporipoxvirus (rabbit (Shope) fibroma, myxoma); and Suipoxvirus (swinepox). The entomopoxviruses comprise three genera: A, B and C.

According to one aspect of the present invention, a method is provided for producing a modified eukaryotic cytoplasmic DNA virus by direct molecular cloning of a modified cytoplasmic DNA virus genome. This method comprises a step of modifying under extracellular conditions a purified DNA molecule comprising a first cytoplasmic DNA virus genome to produce a modified DNA molecule comprising a modified cytoplasmic DNA virus genome.

A purified DNA molecule suitable for modification according to the present method is prepared, for example, by isolation of genomic DNA from virus particles, according to standard methods for isolation of genomic DNA from eukaryotic cytoplasmic DNA viruses. See, for instance, Example 1, hereinbelow. Alternatively, some or all of the purified DNA molecule may be prepared by molecular cloning or chemical synthesis.

Modifying a purified DNA molecule comprising a virus genome within the scope of the present invention includes making any heritable change in the DNA sequence of that genome. Such changes include, for example, inserting a DNA sequence into that genome, deleting a DNA sequence from that genome, or substitution of a DNA sequence in that genome with a different DNA sequence. The DNA sequence that is inserted, deleted or substituted is comprised of a single DNA base pair or more than one DNA base pair.

According to this aspect of the invention, the step of modifying a DNA molecule comprising a first DNA virus genome is performed with any technique that is suitable for extracellularly modifying the sequence of a DNA molecule. For instance, modifying a DNA molecule according to the present invention comprehends modifying the purified DNA molecule with a physical mutagen, such as ultraviolet light, or with a chemical mutagen. Numerous methods of extracellular mutagenesis of purified DNA molecules are well known in the field of genetic engineering.

In another embodiment, the step of modifying the DNA molecule comprises joining together DNA segments to form the modified DNA molecule which comprises the modified viral genome. According to one aspect of this embodiment, some or all of the DNA segments joined together to form the modified DNA molecule are produced by cleaving the DNA molecule comprising the first virus genome with a nuclease, preferably a sequence-specific endonuclease. Alternatively, some or all of the DNA segments joined together to form the modified DNA molecule may be produced by chemical synthesis using well known methods.

In some embodiments, the step of joining together DNA segments to produce the modified DNA molecule comprises an extracellular step of ligating those DNA segments together using a ligase, such as a bacterial or bacteriophage ligase, according to widely known recombinant DNA methods. Optionally, this DNA modification step also comprises treating ends of DNA segments cleaved from the DNA molecule comprising the first virus genome with a phosphatase, for instance, calf intestine phosphatase. This enzyme removes phosphate moieties and thereby prevents religation of one DNA segment produced by cleaving the DNA molecule with another such segment.

In an alternative approach to joining the DNA segments, some or all of the DNA segments are joined by extracellular annealing of cohesive ends that are sufficiently long to enable transfection of the modified DNA molecule into a host cell where ligation of the annealed DNA segments occurs.

In another embodiment of this method, the step of modifying the DNA molecule comprising the first virus genome includes a step of joining at least some DNA segments resulting from cleaving a genomic DNA molecule of the first virus together with an additional DNA segment to produce the modified DNA molecule. In a preferred embodiment of this aspect of the invention, this step comprises cleaving a genomic viral DNA molecule with a sequence-specific endonuclease at a unique cleavage site in the first virus genome, thereby producing two DNA "arms" of the genomic virus DNA. The two arms are then ligated together with a foreign DNA comprising a sequence of interest.

A DNA sequence of interest as used herein to describe the sequence of a foreign DNA segment that is ligated with virus DNA arms comprises, in the first instance, a DNA sequence that is not naturally occurring in a genome of a eukaryotic cytoplasmic DNA virus. Alternatively, a DNA sequence of interest comprises a sequence comprised of a sequence that is naturally occurring in a genome of a eukaryotic cytoplasmic DNA virus as well as a sequence that is not naturally occurring in such a genome. Furthermore, a sequence of interest may comprise only sequences that are naturally occurring in a eukaryotic cytoplasmic DNA virus, where such a sequence is inserted into a location in the genome of that cytoplasmic DNA virus different from the location where that sequence naturally occurs. Moreover, insertion of a naturally occurring viral sequence of interest from one DNA virus into another, or from one part of a single viral genome into another part of that genome, will necessarily create a sequence that is "not naturally occurring in the genome of a cytoplasmic DNA virus" according to the present invention, at the junction of the viral genome and the inserted viral sequence of interest.

The foreign DNA segment that is ligated to the two arms of genomic virus DNA comprises ends that are compatible for ligation with the ends of the viral DNA arms. The compatible ends may be complementary cohesive ends or blunt ends. The ligation step in this particular method produces a modified DNA molecule comprising the first virus genome with the DNA sequence of the foreign DNA inserted into the first virus genome at the unique cleavage site.

This embodiment of a method in which a DNA sequence is inserted into the genome of the first virus is exemplified herein by, inter alia, a method for inserting a gene expression cassette into a vaccinia virus genome at a unique cleavage site for the bacterial restriction endonuclease NotI or SmaI, as described in Examples 1 and 3, respectively. This embodiment is also exemplified by insertion of a gene cassette into the genome of a recombinant fowlpox virus vector, at a unique NotI site within the sequence of a bacterial gene within the recombinant fowlpox virus genome, as described in Example 2.

Inserting a foreign DNA into a unique site in a eukaryotic cytoplasmic DNA virus genome according to the present invention is useful for the purpose of expressing a desired protein, particularly a human protein. For instance, Example 5 describes insertion of genes for plasminogen, prothrombin and human immunodeficiency virus glycoprotein 160 (HIV gp160) into a unique cleavage site of a vaccinia virus vector and the use of the resulting modified vaccinia viruses for production of these proteins. The foreign proteins may be produced in cell cultures, for preparing purified proteins, or directly in human or animal hosts, for immunizing the host with a vaccine comprising a modified virus according to the present invention.

In certain embodiments, the step of modifying a virus genome by inserting a DNA sequence comprises introducing or eliminating a marker gene function for distinguishing the modified virus genome from the first virus genome. In one such embodiment, a DNA sequence inserted into the first virus genome comprises a selective marker gene and the step of recovering the infectious modified poxvirus virions produced by the first host cell comprises a step of infecting a second host cell with those infectious virions under conditions that select for a poxvirus genome expressing the selective marker gene. In a preferred embodiment of this aspect of the invention, expression of the selective marker gene in the second host cell confers on the second host cell resistance to a cytotoxic drug. This drug is present during infection of the second host cell at a level sufficient to select for a poxvirus genome expressing the selective marker gene. In this case the drug selects for a modified virus genome having the inserted selective marker gene and selects against any genome lacking that marker gene.

Insertion of a DNA sequence comprising a selective marker gene for distinguishing the modified virus genome from the first virus genome is particularly useful when a genomic DNA molecule of the first virus has been cleaved at a unique cleavage site and, therefore, the resulting viral DNA arms are likely to religate without insertion of the desired DNA sequence. This approach is exemplified by a method for inserting a gene for the enzyme xanthine-guanine-phosphoribosyltransferase of *Escherichia coli* (hereinafter, the "gpt" gene) into, inter alia, a vaccinia virus genome or a fowlpox virus genome at a unique NotI site, as described in Examples 1 and 2, respectively.

A method for eliminating a marker gene function from the first virus genome to distinguish the modified viral genome from the first genome is exemplified in Example 2. This method relates to insertion of a foreign DNA sequence into a fowlpox virus genome into a NotI site residing in an *E. coli* lacZ gene coding for β-galactosidase. As described in Example 2 (avipox), insertion of a DNA sequence into this site disrupts the lacZ coding sequence and thereby prevents production of β-galactosidase. Expression of this enzyme produces a "blue plaque" phenotype for a virus carrying the lacZ gene. Accordingly, a modified viral genome carrying an insertion of a DNA sequence in this site exhibits a white plaque phenotype that distinguishes the modified virus from the first virus. In other embodiments of methods according to this invention, a functioning *E. coli* lacZ gene is transferred into the vector with another gene of interest to serve as a marker for modified viruses containing the desired insert.

In still other embodiments of the method of this invention, the step of modifying a DNA molecule comprises introducing a new cleavage site for a sequence-specific endonuclease into the first virus genome. One example of this embodiment comprises inserting into a existing unique site in a first poxvirus genome a foreign DNA comprised of a synthetic DNA "linker" as described in Example 6 This linker comprises a "multiple cloning site" comprised of several closely adjacent cleavage sites that are useful for insertion of foreign DNA into the modified poxvirus genome. Advantageously, the cleavage sites in the multiple cloning site are not present in the first viral genome and, therefore, are unique in the modified viral genome.

More particularly, the step of modifying a DNA molecule comprising a first viral genome also includes inserting a DNA sequence between a first and a second cleavage site for a sequence-specific endonuclease. In one such embodiment, the first viral genome comprises a multiple cloning site comprised of cleavage sites that are unique in the first viral genome. According to this method, cleaving a DNA molecule comprising a first viral genome at two such unique sites in the multiple cloning site produces two viral DNA arms having cohesive ends that are not compatible for ligation with each other. The intervening DNA segment between the two unique cleavage sites in the multiple cloning site is removed from the cleaved viral DNA arms, for example, by ethanol precipitation of these arms, as described for inserting a human prothrombin gene into a modified poxvirus vector in Example 5.

Inserting a DNA segment into a viral genome between two unique cleavage sites is useful for "forced" cloning of DNA inserts having cohesive ends compatible for ligation with each of the vector arms. In other words, this method involving cleavage of viral DNA at two sites is useful for increasing the yield of viral genomes resulting from ligation of viral DNA arms compared to arms prepared by cleavage of viral DNA at a single site, because the arms of this method do not have ends compatible for ligation. This forced cloning method also directs orientation of the DNA inserted within the modified viral genome because only one viral DNA arm is compatible for ligation to each end of the inserted DNA.

The forced cloning method of the present invention is demonstrated, for example, by insertion of a gene expression cassette comprised of a human prothrombin gene into a multiple cloning site of a vaccinia virus vector, as described in Example 5.

In a preferred embodiment, the intervening DNA segment between two unique cleavage sites in the first viral genome is not essential for replication of the first viral genome and, therefore, neither deleting this sequence nor replacing it with another DNA segment prevents replication of the resulting modified genome. Alternatively, the intervening DNA segment is replaced by a DNA segment comprising that portion of the intervening sequence that is essential for viral replication linked to an additional DNA sequence that is to be inserted into the first viral genome.

In another aspect of the present method, the step of modifying the first viral genome comprises eliminating an undesirable cleavage site for a sequence-specific endonuclease. Modifications of this type can be made repeatedly, if necessary, for example, to delete redundant cleavage sites for the same nuclease, thereby ultimately producing a modified viral genome having a unique cleavage site for a particular nuclease.

Methods that are particularly suitable for eliminating a cleavage site from a viral genome are known in the art. These include various general site-specific mutagenesis methods. One particular method for eliminating an endonuclease cleavage site from a viral genome involves extracellular treatment of genomic viral DNA to select for mutant genomic DNA molecules that are resistant to cleavage by the pertinent endonuclease.

Another method for eliminating a cleavage site from a viral genome is by ligating a cleaved viral DNA molecule with a DNA segment, for instance, a synthetic DNA segment, comprising an end compatible for ligation with the cleaved viral DNA but lacking a portion of the recognition sequence for the nuclease that cleaved the viral DNA. In this method, the cleavage site for the sequence-specific endonuclease that cleaves the viral DNA comprises a nuclease recognition sequence that extends beyond the sequences encompassed in the cohesive ends into the sequences immediately adjacent to the cohesive ends. The synthetic insert comprises cohesive ends compatible for ligation with the viral DNA arms cleaved at a single site. However, the sequence immediately adjacent to one cohesive end of the synthetic insert differs from the recognition sequence that is required for cleavage by the enzyme that cleaved the viral DNA. Therefore, ligation of this end of the synthetic DNA segment with a viral arm does not reconstitute a functional cleavage site for the nuclease that cleaved the viral DNA. This method for eliminating a cleavage site from a viral genome is exemplified in Example 4 by insertion of a synthetic DNA segment comprising a multiple cloning site into a unique cleavage site of a viral genome.

To prevent inactivation of a viral genome as a result of modification, it is evident that the modification of a viral genome according to the present method must be made in a region of the viral genome that is not essential for virus multiplication in cell culture under the conditions employed for propagation of the resulting modified virus. DNA virus genomic regions comprising sequences that are nonessential for multiplication in cell culture and otherwise suitable for modification according to the present methods include sequences between genes (i.e., intergenic regions) and sequences of genes that are not required for multiplication of the modified viral genome.

A nonessential site suitable for modifying a selected genome of a eukaryotic cytoplasmic DNA virus according to the present invention may be identified by making a desired modification and determining whether such modification interferes with replication of that genome under the desired infection conditions. More in particular, restriction enzyme cleavage sites in a viral genome, including unique sites in that genome, are identified, for instance, by digestion of genomic DNA and analysis of the resulting fragments, using procedures widely known in the art. The genome may be disrupted by trial insertion of a short synthetic DNA segment into a selected target cleavage site by the direct cloning method of the present invention. Recovery of a virus comprised of the trial insert at the selected target site provides a direct indication that the target site is in a nonessential region of that genome. Alternatively, if no useful cleavage site exists at a particular genomic target location, such a site may be introduced using either direct molecular cloning or conventional genome construction based on marker rescue techniques. In this case, successful recovery of a virus comprised of the inserted cleavage site at the target location directly indicates that the target location is in a nonessential region suitable for modification according to the present invention.

Certain nonessential genomic regions suitable for practicing the present invention with poxviruses have been described. See, for instance, Goebel et al., *Virology* 179: 247–266 (1990), Table 1, the disclosure of which is hereby incorporated herein by reference.

In further embodiments of the method, at least a portion of the DNA sequence which is inserted into the first viral genome is under transcriptional control of a promoter. In certain embodiments, this promoter is located in the DNA sequence that is inserted into the first viral genome and, therefore, controls transcription of that portion of the inserted DNA sequence downstream from the promoter. This approach is exemplified by insertion into a poxviral genome of a gene cassette comprising a promoter functionally linked to an open reading frame, as described in Examples 1 through 5.

In another preferred embodiment, the promoter controlling transcription of the DNA sequence that is inserted into the first viral genome is located in the modified viral genome upstream of the inserted DNA sequence. This approach is illustrated by insertion of a cDNA encoding the human von Willebrand factor protein into a multiple cloning site that is functionally linked to an upstream promoter in a vaccinia virus vector, as described in Example 6.

In certain embodiments, the promoter controlling the inserted DNA sequence is recognized by an RNA polymerase encoded by the modified viral genome. Alternatively, this promoter might be recognized only by an RNA polymerase encoded by another genome, for example, another viral or cellular genome. For example, this RNA polymerase might be a bacteriophage T7 polymerase that is encoded by another cytoplasmic DNA virus genome or by the genome of a modified host cell. The T7 polymerase and promoter have been used, for instance, in recombinant poxviruses to enhance expression of an inserted DNA sequence. See, for example, Fuerst, T. R. et al., *J. Mol. Biol.* 205: 333–348 (1989). Provision of the T7 RNA polymerase on a separate genome is used to prevent expression of a DNA sequence inserted into the modified poxvirus genome except when the separate genome is present.

In still other embodiments, the promoter controlling the insert is suitable for initiation of transcription by a cytoplasmic DNA virus RNA polymerase. In some embodiments, the promoter comprises a modification of a DNA sequence of a naturally occurring viral promoter. One such embodiment is exemplified by use of a "synthetic" vaccinia virus promoter, such as the "S3A" and "S4" promoters described, inter alia, in Examples 5 and 6.

The eukaryotic cytoplasmic DNA virus genomic construction method of the present invention further comprises a step of introducing the modified DNA molecule comprising the modified viral genome into a first host cell which packages the modified DNA molecule into infectious modified cytoplasmic DNA virus virions. The modified DNA molecule is introduced into the first host cell by a method suitable for transfection of that first host cell with a DNA molecule, for instance, by methods known in the art for transfection of other DNAs into comparable host cells. For example, in a preferred embodiment, the modified DNA is introduced into the first host cell using the calcium phosphate precipitation technique of Graham and van der Eb, *Virology* 52:456–467 (1973).

In a preferred embodiment, this method for producing a modified eukaryotic cytoplasmic DNA virus further comprises a step of infecting the first host cell with a second cytoplasmic DNA virus comprising a second cytoplasmic DNA virus genome which is expressed to package the modified DNA molecule into infectious modified cytoplasmic DNA virus virions. In the method comprising infection of the first host cell with a second virus, introducing the recombinant DNA molecule into the first host cell is carried out advantageously about one hour after infecting the first host cell with the second virus.

In another embodiment of this method, the necessary packaging functions in the first host cell are supplied by a genetic element other than a complete genome of a second virus, such as a plasmid or other expression vector suitable for transforming the first host cell and expressing the required helper virus functions. Use of a nonviral genetic element to provide helper functions enables production of genetically stable helper cells that do not produce infectious helper virus. Use of such a helper cell as a first host cell for packaging of a modified DNA molecule advantageously produces only virions comprised of that modified DNA.

In the method comprising infection of the first host cell with a second virus, the second virus is selected so that expression of the second viral genome in the first host cell packages the modified DNA molecule into infectious virions comprised of the modified viral genome. Pursuant to the present invention, it is feasible to effect intracellular packaging of a modified DNA comprising a eukaryotic cytoplasmic DNA virus genome by transfection into cells infected with a closely related virus. For instance, DNA of a first poxvirus genus is packaged by a host cell infected with a second poxvirus of the same poxvirus subfamily, whether from the same or a different genus.

In certain embodiments, expression of the second viral genome in the first host cell produces infectious virions comprised of the second viral genome as well as of the modified viral genome. This situation obtains, for instance, in the case of homologous packaging of a first poxvirus DNA from one genus by a second poxvirus of the same genus. Here, although the transfected DNA theoretically could be packaged directly, i.e., without transcription of the transfected genome, homologous packaging of the transfected DNA molecule probably involves transcription and replication of both the transfected DNA and the DNA of the helper virus. This situation is illustrated, inter alia, with homologous packaging of poxvirus DNA in Examples 1 and 2.

However, in other embodiments expression of the second viral genome in the first host cell does not produce infectious virions comprised of the second viral genome. In cases involving heterologous packaging, for instance, passive packaging alone cannot produce viable virus particles from the transfected DNA. In such a case it is advantageous to select a second (helper) virus which provides an RNA polymerase that recognizes the transfected DNA as a template and thereby serves to initiate transcription and, ultimately, replication of the transfected DNA. This case is exemplified by the reactivation of a modified genome of an orthopoxvirus (vaccinia) vector by an avipox (fowlpox) helper virus in a mammalian first host cell in which the avipox virus is unable to produce infectious virions comprised of the avipoxvirus genome, as described in Examples 3 and 7.

The use of a heterologous virus to package the modified DNA molecule, such as the use of fowlpox or ectromelia (mouse pox) virus as a helper for vaccinia virus constructs, advantageously minimizes recombination events between the helper virus genome and the transfected genome which take place when homologous sequences of closely related viruses are present in one cell. See Fenner & Comben (1958); Fenner (1959).

In certain embodiments of the method for using a helper virus for DNA packaging, the step of recovering the infectious virions comprised of the modified viral genome comprises a step of infecting a second host cell with infectious virions produced by the first host cell. Advantageously, the second host cell is infected under conditions such that expression of the second viral genome in the second host cell does not produce infectious virions comprised of the second virus genome. In other words, the second host cell is infected under conditions that select for replication of the modified virus and against the helper virus. This method is exemplified by a method in which the modified genome is a modified vaccinia virus genome, the second genome is a fowlpox virus genome, and the second host cell is a mammalian cell. In this method, the modified virus is plaque purified in cultures of the mammalian host cell in which fowlpox virus does not produce infectious virions, as described in Example 3.

In another embodiment in which the second host cell is infected under conditions that select for the modified virus, the modified viral genome comprises a functional host range gene required to produce infectious virions in the second host cell. The second viral genome lacks this functional host range gene. This embodiment is illustrated by a method in which the modified viral genome is a modified vaccinia virus genome comprising a functional host range gene required to produce infectious vaccinia virus in a human (MRC 5) cell which is used as the second host cell, as described in Example 8.

In yet another embodiment involving selection for modified virus in a second host cell, the modified viral genome comprises a selective marker gene which the second viral genome lacks, and the step of infecting the second host cell is carried out under conditions that select for a viral genome expressing the selective marker gene. For example, expression of the selective marker gene in the second host cell may confer on that cell resistance to a cytotoxic drug. The drug is provided during infection of the second host cell at a level sufficient to select for a viral genome expressing the selective marker gene. This approach is exemplified by a method for inserting a gene for the *E. coli* gpt gene into a vaccinia virus genome, as in Example 1, or a fowlpox virus genome, as in Example 2, using in each case a homologous helper virus lacking the selective marker gene.

In still another embodiment involving selection for a modified virus in a second host cell, the modified viral genome comprises a deletion of a selective marker gene that is present in the second viral genome. Here, the step of infecting the second host cell is carried out under conditions that select against a viral genome expressing that selective marker gene. For example, expression of a poxvirus thymidine kinase (tk) gene in the second host cell (i.e., a thymidine kinase-negative host cell) renders the second (helper) virus sensitive to the metabolic inhibitor, 5-bromo-deoxyuridine. Example 4 describes the use of these inhibitors during infection of a second host cell to select for a vaccinia virus vector (vdTK) in which the tk gene is deleted and replaced by a multiple cloning site.

Another aspect of the present invention relates to a eukaryotic cytoplasmic DNA virus comprised of a modified viral genome. A modified genome of a cytoplasmic DNA virus within the scope of the present invention comprises distinct component DNA sequences which are distinguishable from each other, for example, by routine nucleic acid hybridization or DNA sequencing methods.

In certain embodiments, for instance, the modified viral genome comprises a first genome of a first eukaryotic cytoplasmic DNA virus. This first genome is comprised of a cleavage site for a sequence-specific endonuclease that is a unique site in the first genome. In this embodiment, the sequences of the modified genome that comprises the first viral genome are homologous to a genome of a naturally occurring eukaryotic cytoplasmic DNA virus. Further, the sequences of this first virus are interrupted by a DNA sequence of interest as defined hereinabove.

To determine whether this sequence is inserted into a unique cleavage site in the first viral genome, as required for this embodiment of a modified viral genome, the sequences immediately flanking the insert are compared with sequences of cleavage sites for sequence-specific endonucleases.

In one form of this embodiment in which a DNA sequence is inserted into a unique cleavage site in the first viral genome, the inserted sequence in the first viral genome is flanked by two identical intact cleavage sites for a sequence-specific endonuclease and these two sites are the only sites for this nuclease in the complete modified genome. Each of these two sites is comprised of combined portions of cleaved sites from the first viral genome and the inserted DNA sequence.

More particularly, each strand of a double-stranded DNA comprised of a cleavage site for a sequence-specific endonuclease may be considered to comprise a complete cleavage site sequence ($S_LS_R$) consisting of a left cleavage site sequence ($S_L$) and a right cleavage site sequence ($S_R$) separated by the monophosphate linkage that is disrupted by cleavage with the appropriate nuclease. In certain forms of this embodiment, insertion of a DNA sequence into a unique restriction site reproduces two complete sites flanking the insert.

In other forms of this embodiment, however, insertion of the DNA sequence into a unique cleavage site does not recreate the original cleavage site at each end of the inserted DNA sequence. See, for instance, the method for elimination of a cleavage site described in Example 6. Thus, the inserted DNA may be flanked at one end (e.g., the left end) by a complete cleavage site ($S_LS_R$) while the right end terminates in a sequence that differs from $S_L$ directly linked to an $S_R$ sequence in the first viral genome. More generally, in any modified viral genome of this invention, the DNA sequence inserted into a unique site in a first viral genome will be flanked by two the matching parts ($S_L$ and $S_R$) of a cleaved site which does not occur in the modified viral genome outside of the inserted DNA.

In other embodiments, the modified viral genome is comprised of a DNA sequence that is inserted between two unique sites in the first viral genome. In this case, if the first viral genome is a naturally occurring genome of a eukaryotic cytoplasmic DNA virus, the insert will be encompassed by viral sequences separated from the foreign DNA sequence at least by recognizable $S_L$ and $S_R$ portions of the two different original cleavage sites.

In additional embodiments, the modified viral genome comprises a unique cleavage site located in a DNA sequence that is not naturally occurring in a genome of a eukaryotic cytoplasmic DNA virus. In this case, this foreign DNA is not separated from the natural viral DNA sequences by recognizable $S_L$ and $S_R$ portions of cleavage sites. In certain forms of this embodiment, the first foreign DNA sequence is interrupted by a second foreign DNA sequence inserted into a unique cleavage site in the first sequence or between two such sites in the first sequence. In these embodiments the second foreign DNA is separated from the first foreign DNA sequences by recognizable $S_L$ and $S_R$ portions of sequence-specific endonuclease cleavage sites. In this case, all sequences surrounding this second foreign DNA sequence comprise the genome of the first virus according to this invention.

Preferred embodiments of modified eukaryotic cytoplasmic DNA viruses of this invention include a first major embodiment in which the modified viral genome comprises (I) a first genome of a first eukaryotic cytoplasmic DNA virus that is comprised of a cleavage site for a sequence-specific endonuclease. This site is a unique site in the first viral genome. The modified viral genome of this embodiment also comprises (II) a first DNA sequence of interest. This DNA sequence is inserted into the unique site in the first cytoplasmic DNA virus genome.

In one variation of this first embodiment of a modified eukaryotic cytoplasmic DNA virus, the first viral genome comprised of the unique site is a naturally occurring viral genome. This variation is exemplified herein by a modified poxvirus genome comprised of a naturally occurring vaccinia virus genome which has unique cleavage sites for the bacterial restriction endonucleases NotI and SmaI, as described in Examples 1 and 3. In this embodiment, the first DNA sequence of interest, which is inserted into the unique site, is exemplified by an *E. coli* gpt gene driven by a naturally occurring vaccinia virus promoter inserted into the NotI site (Example 1) or into the SmaI site (Example 3) of a vaccinia virus genome.

In a second form of this first embodiment of a modified virus, the first viral genome comprised of the unique site also comprises a second DNA sequence not naturally occurring in a viral genome. Furthermore, this second DNA sequence includes the unique site for insertion of the first DNA sequence. This variation is exemplified herein by a modified fowlpox virus genome comprising a DNA sequence encoding an *Escherichia coli* β-galactosidase gene, as described in Example 2. This bacterial gene includes a cleavage site for the bacterial restriction endonuclease NotI that is unique in the modified fowlpox virus genome and, therefore, is particularly convenient for insertion of foreign DNA sequences.

In another variation of this first embodiment of a modified virus, at least a portion of the first DNA sequence that is inserted into the unique site is under transcriptional control of a promoter. In some instances, the promoter is located in the first DNA sequence that is inserted into the first viral genome. This holds, for instance, when the inserted DNA comprises a gene cassette including a promoter and a functionally linked gene, as described, inter alia, in Examples 1 and 2.

In a second embodiment of a modified cytoplasmic DNA virus of this invention, the modified viral genome comprises (I) a first viral genome comprised of a first and a second cleavage site for a sequence-specific endonuclease where each of these sites is unique in the first virus genome. In one preferred variation of this embodiment, the first viral genome comprises a multiple cloning site comprised of several unique cleavage sites.

In this second embodiment, the modified viral genome also comprises (II) a first DNA sequence not naturally occurring in a genome of a eukaryotic cytoplasmic DNA virus, and this first DNA sequence is inserted into the first viral genome between the first and second unique cleavage sites.

In a third embodiment of a modified cytoplasmic DNA virus of this invention, the modified viral genome comprises (I) a first viral genome comprised of a first DNA sequence not naturally occurring in a genome of a eukaryotic cytoplasmic DNA virus. This first DNA sequence is comprised of a cleavage site for a sequence-specific endonuclease that is a unique site in the modified viral genome. The modified viral genome of this embodiment further comprises (II) a promoter located such that a DNA sequence inserted into the unique site is under transcriptional control of the promoter. This first DNA sequence does not have a translation start codon between the promoter and the unique site used for insertion of a DNA sequence. This embodiment is exemplified by the vaccinia virus vector (vS4) described in Example 6, which has a "synthetic" poxvirus promoter located such that this promoter controls transcription of a DNA sequence inserted into a multiple cloning site designed for insertion of open reading frames.

Another aspect of the present invention relates to a DNA molecule comprising a modified viral genome of a modified eukaryotic cytoplasmic DNA virus of this invention. In a preferred embodiment, this DNA molecule is prepared by extraction of genomic DNA molecules from virions of a modified eukaryotic cytoplasmic DNA virus of this invention, or from cells infected with a modified virus of this invention. Methods suitable for extracting modified viral genomic DNAs from virions are known in the art. In addition, suitable methods for preparing DNA of eukaryotic cytoplasmic DNA viruses are described herein in Example 1.

Still another aspect of the present invention relates to genomic DNA arms of a eukaryotic cytoplasmic DNA virus of this invention. These genomic DNA arms are useful for direct molecular cloning of viral genomes comprising foreign DNAs. More particularly, this aspect of the invention relates to two DNA molecules, the left and right genomic arms of a modified viral genome of a eukaryotic cytoplasmic DNA virus. In the practice of the direct cloning method of this invention, described above, either one or both of these arms may consist entirely of a DNA sequence that is naturally occurring in a cytoplasmic DNA virus. But the novel DNA molecule of the present aspect of this invention is a modified arm of a viral genome, in other words, a DNA molecule comprising one end of a modified viral genome of a eukaryotic cytoplasmic DNA virus. This end of the modified viral genome comprises a DNA sequence of interest which distinguishes this DNA molecule from genomic arms consisting of only a sequence that is naturally occurring in a cytoplasmic DNA virus. In addition, the modified viral genome from which the novel arm derives is comprised of a unique cleavage site for a sequence-specific endonuclease. Furthermore, this DNA molecule has a terminus that is homologous to a product of cleaving the unique site in the modified viral genome with the sequence-specific endonuclease.

In a preferred embodiment, this DNA molecule comprising a genomic arm is produced by cleavage of genomic DNA of a modified virus at a unique site for a sequence-specific endonuclease. Alternatively, this DNA molecule may be produced by modifying another DNA molecule to produce a terminus that is homologous to a terminus produced by cleaving a unique site in a modified viral genome. For instance, a DNA molecule according to this aspect of the invention may be produced from an arm of a naturally occurring genomic viral DNA. The required DNA molecule may be produced from such a naturally occurring viral arm, for example, by ligation to a synthetic "adaptor" DNA segment comprised of a cohesive end derived from cleavage site that is not present in the first viral genome. In this instance the end of the first viral genome and the ligated adaptor together comprise one end of a modified viral genome. Accordingly, this particular DNA molecule is not produced by cleavage of a modified viral genomic DNA, but it does comprise a terminus that is homologous to a terminus that is produced by cleaving a unique site in a modified viral genome.

In another embodiment of a modified viral DNA arm of the present invention, the DNA sequence not naturally occurring in a genome of a eukaryotic cytoplasmic DNA virus is comprised of the cleavage site for a sequence-specific endonuclease that is unique in the modified viral genome. This cleavage site further comprises a left cleavage site sequence ($S_L$) for the left genomic arm, or the right cleavage site sequence ($S_R$) for the right genomic DNA arm, occurring complete cleavage site sequence ($S_L S_R$) being unique in the modified viral genome. This embodiment is exemplified, inter alia, by DNA arms produced from a fowlpox virus vector by the bacterial restriction endonuclease NotI, as described in Example 2, or by arms of a vaccinia virus vector (vS4) cleaved at any of several unique sites of an inserted multiple cloning site, as described in Example 6.

Yet another aspect of the present invention relates to a kit for direct molecular cloning of a modified viral genome of a eukaryotic cytoplasmic DNA virus. This kit comprises (I) purified DNA molecules of this invention. These DNA molecules comprise either genomic viral DNA arms of this invention or a complete, intact modified viral genome of this invention, or both. The viral DNA arms are useful for direct ligation to foreign DNA segments to be cloned, while the intact viral DNAs are useful for cloning after cleavage, for instance, with a sequence-specific endonuclease at a site that is unique in the modified viral genome.

The kit further comprises (II) a DNA ligase and (III) solutions of a buffer and other reagents suitable for ligation of DNA segments together to produce a modified DNA molecule comprising said modified viral genome. A suitable buffer and reagents for ligation are described, for instance, in Example 1.

In one embodiment, this kit further comprises a plasmid comprised of a gene expression cassette flanked by sites for cleavage with a sequence-specific endonuclease. When cleaved by the appropriate sequence-specific endonuclease, the sites flanking the cassette produce ends that are compatible for insertion of this cassette into a unique cleavage site of the modified viral genome that is encoded by the DNA molecule.

In another embodiment, the cloning kit further comprises a first host cell and a second (helper) virus suitable for packaging the modified viral genome into infectious virions.

Yet another aspect of the present invention relates to plasmids which are particularly suited to serve as intermediates in the construction of modified cytoplasmic DNA virus vectors of this invention. According to one embodiment of this aspect, there is provided a plasmid comprising a DNA segment having at each end the same cleavage site for a sequence-specific endonuclease. This site is also a unique site in a first cytoplasmic DNA virus genome according to the present invention. This DNA segment comprises a multiple cloning site comprised of several closely adjacent sequence-specific endonuclease cleavage sites that are unique in the plasmid and, therefore, useful for insertion of foreign DNA segments into the plasmid.

This plasmid is useful for insertion of genes into a unique cleavage site of the DNA segment for subsequent transfer of that segment into a unique cleavage site of a cytoplasmic DNA virus using the direct molecular cloning method of this invention. This plasmid is exemplified by the plasmid pN2 (see Example 1, FIG. 1.3) which has a DNA segment comprising a multiple cloning site flanked by NotI sites and containing the following additional bacterial restriction enzyme cleavage sites in the stated order: XbaI, SpeI, BamHI, SmaI, PstI, EcoRI, EcoRV, HindIII and ClaI.

Another plasmid of the present invention comprises a DNA segment having at each end a cleavage site that is a unique site in a cytoplasmic DNA virus. The DNA segment of this plasmid also comprises several restriction enzyme cleavage sites that are unique in the plasmid. This DNA segment further comprises a selective marker gene (e.g., an E. coli gpt gene) under transcriptional control of a cytoplasmic DNA virus promoter (e.g., the vaccinia virus P7.5 promoter). This plasmid is exemplified by two plasmids designated pN2-gpta and pN2-gptb which contain a DNA segment flanked by NotI sites and comprising an E. coli gpt gene under transcriptional control of a vaccinia virus P7.5 promoter. This plasmid was created by insertion of the promoter-gene cassette into the SmaI site of the plasmid pN2, as described in FIG. 1.3.

In a further modification of the above plasmid, the DNA segment further comprises a second poxvirus promoter operatively linked to a DNA sequence comprising a restriction endonuclease cleavage site. This plasmid, as exemplified by the plasmid pN2gpt-S3A (FIG. 4.6) can be used to insert open reading frames lacking their own initiation codon for transfer into a vaccinia virus vector. Similarly, the plasmid pN2gpt-S4 (FIG. 4.6) can be used to insert complete open reading frames including an AUG translation start codon.

In another embodiment, this plasmid further comprises a DNA sequence encoding human plasminogen, wherein the DNA sequence is operatively linked to the poxvirus promoter and start codon. This plasmid is exemplified by plasmid pN2gpt-GPg, encoding human glu-plasminogen, and by plasmid pN2gpt-LPg, encoding lys-plasminogen, in which the coding region for amino acids 1–77 of human plasminogen is deleted (FIGS. 5.2 and 5.3).

In a related form, this plasmid further comprises a DNA sequence encoding human immunodeficiency virus (HIV) gp160, wherein the DNA sequence is operatively linked to the poxvirus promoter and start codon. This is exemplified by plasmid pN2gpt-gp160, having the gp160 gene controlled by the synthetic vaccinia virus promoter S4 (FIG. 5.4).

Another plasmid of the present invention comprises a segment of a cytoplasmic DNA virus genome in which the viral thymidine kinase (tk) gene is located. In this plasmid, the coding region of the tk gene has been modified (deleted) to prevent expression of active tk enzyme. This plasmid is useful as an intermediate in construction of a cytoplasmic DNA virus vector having a defective tk gene, using conventional methods of marker rescue, as described for the vaccinia virus tk gene, using plasmid pHindJ-3. In a related embodiment, a plasmid comprising a modified tk gene region of a cytoplasmic DNA virus further comprises a multiple cloning site comprised of several closely adjacent sequence-specific endonuclease cleavage sites that are unique in the plasmid. Furthermore, each of these sites is absent in a cytoplasmic DNA virus into which the modified tk gene region is to be inserted. Therefore, after insertion of the modified tk gene region comprising these unique sites into that viral genome, these sites are useful for insertion of foreign DNA segments into the cytoplasmic DNA virus genome carrying the modified tk gene region, according to the direct cloning method of the present invention.

This plasmid comprising a modified tk gene region containing a multiple cloning site is exemplified by plasmid pHindJ-3 in which the modified vaccinia virus tk gene region of plasmid pHindJ-2 has inserted a multiple cloning site with the unique sites NotI, SmaI, ApaI and RsrII, flanked by SfiI sites (FIG. 4.2). To further facilitate forced cloning in a vaccinia virus vector, each of the two SfiI sites is also made unique in the vector by exploiting the variable nature of the SfiI recognition sequence, as detailed in Example 4.

In still another embodiment, a plasmid comprises a sequence-specific endonuclease cleavage site that is unique in the genome of that virus. Such plasmids are particularly suitable for construction of gene expressions cassettes for transfer into a vector having the aforementioned unique site. The plasmid pA0 exemplifies the basic plasmid that contains a master cloning site comprised of the unique sites of the master cloning site of the vdTK vaccinia virus vector (FIG. 4.3). The related plasmids pa1 and pA2 were designed for insertion of DNA segments, for instance, synthetic or natural promoter fragments and were constructed by inserting into the XhoI site of pA0 a linker comprising a second multiple cloning site of frequently cutting enzymes that do not cleave pA0. Both plasmids have the same structure except for the orientation of the second multiple cloning site (FIG. 4.3).

In yet another embodiment, a plasmid comprises a poxvirus promoter operatively linked to a translational start codon, wherein this start codon is immediately followed by a second restriction endonuclease cleavage site suitably arranged to permit translation of an open reading frame inserted into the second restriction endonuclease cleavage site. This plasmid is exemplified by plasmids pA1-S1 and pA2-S1 which provide the strong synthetic poxvirus promoter S1, including a translational start codon, followed by a single EcoRI site suitable for insertion of open reading frames that do not have an associated start codon (FIG. 4.4). Plasmids pA1-S2 and pA2-S2 are similar to pA1-S1 and pA2-S1 but have a different poxvirus promoter, S2 (FIG. 4.5).

In a related embodiment, the plasmid above further comprises a DNA sequence encoding human prothrombin, wherein said DNA sequence is operatively linked to said poxvirus promoter and said start codon. This plasmid is exemplified by the plasmid pA1S1-PT (FIG. 5.1) in which a modified prothrombin cDNA is inserted into the single EcoRI site of the plasmid pA1-S1.

Another plasmid of the present invention comprises a modified EcoRI K fragment of vaccinia virus DNA from which the K1L host range gene is deleted. The helper virus vdhr lacking both the K1L and C7L host range genes is constructed from the C7L-negative strain WR-6/2 by marker rescue with a modified EcoRI K fragment from which the K1L host range gene is deleted. See FIG. 8.1. This modified EcoRI K fragment comprises a selective marker gene (the E. coli gpt gene) to facilitate selection for recombinant WR-6/2 genomes comprising the modified EcoRI K fragment using intracellular marker rescue as described by Sam & Dumbell, 1981. The exemplifying plasmid is designated pEcoK-dhr (FIG. 8.1).

In a further step pEcoK-dhr is linearized with NotI and ligated with a 1.1 kb P7.5-gpt gene cassette derived from plasmid pN2-gpta (Example 4) by NotI digestion. The resulting plasmid pdhr-gpt (FIG. 8.1) is used in marker rescue experiments to generate the helper virus vdhr according to the marker rescue method of Sam & Dumbell, 1981.

The present invention is further described below with regard to the following illustrative examples.

EXAMPLE 1

Direct molecular cloning of foreign DNA comprising a selective marker gene (the gpt gene of E. coli) into a unique (NotI) cleavage site in the genome of an orthopoxvirus (vaccinia)

This example demonstrates direct molecular cloning of a gene expression cassette into a poxvirus genome, according to the present invention, by intracellular packaging of genetically engineered poxvirus DNA. In addition, this example illustrates use of a genetic selection procedure for efficient recovery of modified vaccinia viruses containing an inserted selective marker gene. The experimental results also reveal that recombination frequently occurs between the DNA to be packaged and that of the infecting helper virus during packaging when the helper virus DNA is homologous with the DNA to be packaged.

More particularly, a first direct molecular cloning experiment described below shows that a marker gene (gpt-gene) cassette can be inserted as a NotI restriction fragment in NotI-cleaved vaccinia virus DNA and subsequently packaged in vaccinia virus-infected mammalian cells. One of nine plaques examined comprised virus having the predicted structure for a single insert of the gpt-gene in the "a" orientation (see FIG. 1.11). The structure of this clone (designated vp7) was stable during large scale replication in the absence of the selection agent.

In a second series of cloning experiments, seven of twelve clones examined had the expected structure. In this series, however, four small plaques (E1–E4) of slowly replicating viruses were included, although preferably these are not normally selected in the practice of the present invention. Recombinants having multiple inserts of the selective marker gene were also obtained under selective conditions. The stability of these multiple inserts was not examined in the absence of the selective agent which is known to stabilize certain otherwise unstable structures. See Falkner & Moss, *J. Virol.* 64:3108–3111 (1990).

The relatively low yield of predicted structures is not expected given the known precision of genetic engineering methods for site-specific cleavage and ligation of DNA molecules. However, the particular sequence selected for insertion in this model system, the gpt-gene cassette, comprised vaccinia virus DNA sequences of the P7.5 promoter which are homologous to two endogenous promoters in the vaccinia vector which drive two vaccinia virus 7.5-kD polypeptide genes located within the inverted terminal repetitions of the vaccinia genome. See Venkatesan, B., Baroudy B. M. & Moss, B., *Cell* 25: 805–813 (1981). This P7.5 promoter has been used to construct vaccinia virus recombinants by conventional intracellular recombination and can be stably integrated into the vaccinia thymidine kinase gene. Mackett & Smith (1986). Occasionally, however, submolar amounts of DNA fragments appear during analyses of conventional recombinants, which may result from secondary recombination events. Where a P7.5 promoter is inserted near the endogenous P7.5 promoters (i.e., within several kilobases), only recombinants that have an inverted repeat structure are stable, and this observation has been exploited to develop a deletion procedure based on insertion of a tandemly repeated P7.5 promoter segment. Spehner, D., Drillien, R. & Lecocq, J. P. *J. Virol.* 64:527–533 (1990).

In the present case of insertion of the gpt-gene cassette into the NotI site of vaccinia virus, the distance between the P7.5 promoters of the left inverted terminal repetition and that of the inserted cassette is about 30 kb, probably close enough to cause destabilizing secondary recombination events. In fact, only the structures of a few slowly replicating, unstable clones had an insert in the "b" orientation which would produce a tandem repeat arrangement of the inserted and endogenous promoters. Thus, the rare occurrence of this structure can be explained most likely by the closeness of the locations of the P7.5 promoters of the gpt-gene cassette and the endogenous P7.5 promoters and the known instability of tandemly repeated copies of the P7.5 promoter.

In contrast, the virus vp7 and several other isolates (A1, A4, C1 and C2) had inserts in the "a" orientation and were stable. The structural analysis of one isolate, C4, was consistent with a head-to-tail double insert.

The titers of packaged gpt-gene positive viruses in the second series of cloning experiments (five different samples) were approximately $1 \times 10^5$ pfu per $8 \times 10^6$ cells, while in the first experiment a titer of $1-2 \times 10^2$ pfu was obtained from the same number of cells. The titer of modified viruses will be influenced by several factors, including ligation and packaging efficiencies, reaction and culture conditions in the cloning procedure, and by the amount of care taken to avoid shearing of the high molecular vector DNA during handling. Titers of about $10^5$ pfu per $8 \times 10^6$ cells are generally expected under the standard conditions described hereinbelow.

While the present example shows that the unique intergenic NotI site of vaccinia virus can be used for insertion of foreign DNA, it also illustrates the need to consider whether a proposed insert may contain viral sequences of a type and orientation that are known or likely to cause instability of modified viruses. Inserts lacking homology with viral sequences near the insertion site (e.g., within 30 kb) are to be preferred for stability. Accordingly, inserts comprising only short synthetic promoter sequences that are recognized by the transcription system of the vector are preferred to those containing large segments of viral DNA including natural promoters of the viral vector. See, for instance, the S1 promoter in Example 4, below.

The following materials and methods were used throughout this and all subsequent examples, except where otherwise specified.

Purification of orthopox virus and DNA: Vaccinia virus (wildtype Western Reserve (WR) strain; American Type Culture Collection No. VR119) was purified by two successive sucrose gradients according to Mackett, et al. in D. M. GLOVER, DNA CLONING: A PRACTICAL APPROACH, 191–211 (IRL Press, 1985). Viral DNA was prepared by the proteinase KSDS procedure according to Gross-Bellard et al., Eur. J. Biochem. 36:32–38 (1973).

Engineering of isolated poxvirus DNA: Viral DNA (typically 2 to 5 μg) was cleaved with appropriate amounts of one or more sequence-specific endonucleases (for example, the bacterial restriction endonuclease NotI), optionally treated with calf intestine alkaline phosphatase (Boshringer, Inc.), and purified by phenol extraction and ethanol precipitation, according to routine recombinant DNA methods. The resulting viral DNA arms were ligated with a five to fifty-fold molar excess of the DNA fragment to be inserted, having ends compatible for ligation with the viral arms. An aliquot of the ligation reaction was analyzed by field inversion gel electrophoresis.

More particularly, in the second series of experiments (A–E) described below, 2 μg of NotI-digested vaccinia DNA that was not treated with phosphatase were ligated with 200–600 ng of gpt-gene cassette insert in a volume of 30 μl with 5–15 units of T4 ligase for 48 h at 12° C., as summarized in Table 1.

In vivo packaging in mammalian cells: $8 \times 10^6$ African Green monkey (CV-1) cells were infected with helper virus (either vaccinia WR wildtype or WR6/2 virus, or other viruses as indicated) at 0.2 pfu/cell for 2 h. For the initial demonstration of packaging with intact DNA isolated from virions, 20 μg of viral (vPgD) DNA were used. For packaging of extracellularly engineered genomes, 1 μg of DNA purified from a ligation reaction were used. DNAs were transfected into cells by the calcium phosphate precipitation technique (Graham, F. L. & van der Eb, 1973). The cells were incubated for 15 min at room temperature and then nine ml of medium (DMEM, 10% fetal calf serum, glutamine and antibiotics) per one ml precipitate were added to the cells. After four hours the medium was changed and further incubated for two days.

Crude virus stocks were prepared according to standard procedures. Mackett et al., 1985. Plaque assays and selection conditions for the *E. coli* gpt gene are known in the art. See Falkner & Moss, *J. Virol.* 62: 1849–1854 (1988); and Boyle & Coupar, *Gene* 65:123–128 (1988).

Field inversion gel electrophoresis (FIGE). Viral DNA was separated on a 1% agarose gel in Tris-/Acetate/EDTA buffer (40 mM Tris/20 mM glacial acetic acid/2 mM EDTA, pH 8.0) with a microcomputer controlled power supply (Consort Model E790). To separate the whole range of fragments, four programs were run successively, as follows: program 1:5 h at 7 V/cm forward pulse (F) 6 sec, reverse pulse (R) 3 sec, pause 1 sec; program 2:5 h at 7 V/cm, F 4 sec, R 2 sec, pause 1 sec; program 3:5 h at 7 V/cm, F 2 sec, R 1 sec, pause 1 sec; and program 4: 5–10 h at 7 V/cm, F 8 sec, R 4 sec, pause 1 sec.

Construction of plasmid pN2: The plasmid Bluescript II SK (Stratagens, Inc.) was digested with HindII and ligated to NotI linkers (Pharmacia, Inc.). The resulting plasmid, pN2, has a multiple cloning site flanked by NotI sites.

More particularly, the multiple cloning site of pN2 consists of the following sites in the stated order: NotI, XbaI, SpeI, BamHI, SmaI, PstI, EcoRI, EcoRV, HindIII, ClaI and NotI. The inserted NotI linker sequence of pN2 and twenty bases of the 5' and 3' flanking regions of pBluescript II SK-(Stratagens, Inc. La Jolla, USA) are shown in SEQ. ID. NO. 1. The insert sequence starts at position 21 and ends at position 28. (The first "T" residue at the 5'-end corresponds to position number 2266, the last "G" residue at the 3'-end to position number 2313 of the plasmid pN2).

Construction of plasmids pN2-gpta and pN2gptb: The 1.1 kb HpaI-DraI fragment (containing the P7.5 promoter-gpt gene cassette) was isolated from the plasmid pTKgpt-Fls (Falkner & Moss, 1988) and inserted into the SmaI site of the plasmid pN2 (FIG. 1.3). The two resulting plasmids are orientational isomers and were designated pN2-gpta and pN2-gptb. The vaccinia virus P7.5 promoter-*E. coli* gpt-gene cassette and twenty bases of the 5'-and 3'-flanking regions of pN2 are shown for pN2-gpta in SEQ. ID. NO. 2. The insert starts at position 21 and ends at position 1113. The A- residue of the translational initiation codon of the gpt-gene corresponds to position 519. The T-residue of the translational stop codon of the gpt-gene corresponds to position number 975. (The first "C" residue at the 5'-end corresponds to the position number 2227, the last "T" residue at the 3'-end to position number 3359 of the plasmid pN2-gpta).

The reverse complementary form of the vaccinia virus P7.5 promoter-*E. coli* gpt-gene cassette and twenty bases of the 5'- and 3'-flanking regions of pN2 are shown for pN2-gptb in SEQ. ID. NO. 3. The insert starts at position 21 and ends at position 1113. The T-residue of the (reverse complement of the) translational initiation codon CAT corresponds to position 615. The A-residue of the (reverse complement of the) translational stop codon of the gpt gene corresponds to the position number 159.

Other standard techniques of recombinant DNA analysis (Southern blot, PAGE, nick translation, for example) were performed as described. J. SAMBROOK et al., MOLECULAR CLONING (Cold Spring Harbor Laboratory Press, 1989).

Packaging of naked viral DNA: To establish conditions needed for packaging of naked poxvirus DNA by a helper virus, intact DNA isolated from virions of an exemplary recombinant vaccinia virus (vPgD) was transfected into monkey (CV-1) cells infected with a helper virus (vaccinia WR wildtype). The selected recombinant virus has several readily assayable phenotypic markers. Thus, the vPgD genome has incorporated into the viral thymidine kinase (tk) locus a gene for a drug resistance marker (a gene for the enzyme xanthine-guanine-phosphoribosyl-transferase of *Escherichia coli;* i.e., the "gpt" gene) and a gene for a conveniently detected marker protein (human plasminogen). This virus was originally constructed from a vaccinia virus strain [WR 6/2; Moss et al., *J. Virol.* 40:387-95 (1960), which has a deletion of about 9 kb and, consequently, does not express the viral major secreted 35K protein gene described by Kotwal et al., Nature 335: 176-178 (1988)]. The expected phenotype of the packaged virus, therefore, includes: tk-negative (i.e., replication in the presence of bromodeoxy-uridine); gpt-positive (i.e., replication in the presence of mycophenolic acid and xanthine); expressing the human plasminogen gene; and not expressing the secreted 35K protein.

Eight gpt-positive plaques from the above packaging experiment were analyzed. All were tk-negative, and, as shown in FIG. 1.1, all expressed plasminogen. Six of these isolates (lanes 5, 6, 7, 11, 12 and 14) did not express the 35K secreted vaccinia protein and thus showed all the characteristics of the transfected genomic DNA. Two of the plaques also expressed the 35K protein marker (lanes 4 and 13) and therefore were recombinants between the helper wild-type virus (lanes 8 and 15) and the input viral genomes.

This experiment established that naked poxvirus DNA extracted from virions is packaged when transfected into helper virus-infected cells under the tested conditions. Therefore, these conditions were employed for transfection of genomic poxvirus DNA that had been modified by direct molecular cloning, as outlined in FIG. 1.2.

Packaging of extracellularly engineered poxvirus DNA: The genome of vaccinia virus contains a single cleavage site for the NotI sequence-specific endonuclease in the region known as the HindIII F fragment. Inspection of the sequence around this site (Goebel et al., 1990) revealed that it is located in an intergenic region that is unlikely to be essential for viral replication. A marker gene expression cassette was constructed in two plasmids (pN2-gpta and pN2-gptb; FIG. 1.3) by insertion of the *E. coli* gpt gene in each of the two possible orientations. The gpt gene was controlled by the promoter of the vaccinia virus gene coding for the 7.5 kDa protein described in Cochran et al., *J. Virol.* 54:30-37 (1985) (labeled P1 in FIG. 1.2 and P7.5 in FIG. 1.3). The entire marker gene cassette resided on a single 1.1 kb NotI fragment of these plasmids. This restriction fragment from pN2gpta was ligated with NotI digested WR wildtype DNA and transfected into cells that had been infected with helper virus (WR).

In a first cloning experiment, Southern blot analyses of the genomic structures of phenotypically gpt-positive progeny plaques was carried out. The viral isolates were plaque-purified three times and amplified under gpt-selection. The HindIII-digested DNA fragments of cells (CV-1) infected with the different viruses were separated on a 1% agarose gel by a combination of normal electrophoresis and field inversion gel electrophoresis. The gel was then blotted and hybridized with $^{32}$P-labelled vaccinia WR DNA and a labelled probe containing gpt sequences. The results confirmed that all phenotypically marker-positive clones contained the 1.1 kb gpt insert.

FIG. 1.4 shows blots of HindIII DNA fragments from cells infected with the nine virus isolates (lanes 4–12); plaques 2.1.1 to 7.1.1 and 10.1.1 to 12.1.1). The expected 0.8 kb HindIII fragment that contains the gpt sequences can be observed. In lanes 2 and 3, where HindIII-digested wildtype virus DNA (100 and 50 ng, respectively) were loaded, no cross-hybridization to viral sequences was visible.

In the next experiment, total DNAs of CV-1 cell cultures infected with the nine different plaques were digested with NotI. The Southern blot of the separated fragments is shown in FIG. 1.5. Unexpectedly, two bands were visible in most virus isolates, the predicted 1.1 kb insert and a second, larger fragment. Only plaque number 7.1.1 (lane 8) showed the expected single 1.1 kb band. While the hybridization signal of the larger fragment is equally strong in all examined DNAs, the intensity of the 1.1 kb band varied from DNA to DNA, indicating that the 1.1 kb insert may be present in different molar amounts in different genomes. The wildtype virus control (lane 2) did not hybridize to the gpt-gene probe.

The same blot was also hybridized with a vaccinia virus DNA probe. Three fragments are expected, of about 145 kb, 45 kb and 1.1 kb. The blot patterns obtained included the expected bands but also showed an additional band at about 5 kb. Only plaque 7.1.1 did not have the unexpected 5 kb band.

The orientation of the DNA insert in selected engineered vaccinia genomes was also investigated by Southern blotting. As shown in FIG. 1.2, the insert in viral DNAs may be in either the "a" or "b" orientations which are distinguishable by digestion of the DNAs with appropriate restriction enzymes. Following preliminary analyses, isolate 7.1.1 was designated clone vp7, appeared to have the genomic structure of the expected modified virus and therefore was expanded and purified. The DNA of this clone was compared with that of wildtype virus by digestion with several restriction enzymes and separation on an agarose gel by field inversion gel electrophoresis (FIG. 1.6). In a NotI digest of vp7 stained with ethidium bromide (lane 2), only the 145 kb and 45 kb bands contained sufficient DNA mass to be visible, since the band for the 1.1 kb insert was estimated to contain only about 3 ng DNA. However, hybridization with a gpt-specific probe revealed a weak band at 1.1 kb (FIG. 1.7, lane 2).

In digests with HindIII, the expected bands at 1.4 and 0.8 kb were observed. As predicted, the 0.8 kb band hybridized with the gpt-gene probe (FIGS. 1.6 and 1.7, lanes 4). In double digests with NotI and HindIII, the expected 0.8 kb fragment was also observed (FIGS. 1.6 and 1.7, lanes 6).

In digests of vp7 DNA with PstI, a predicted 4.1 kb fragment containing gpt sequences was observed (FIGS. 1.6 and 1.7, lanes 8; the 4.1 kb ethidium bromide-stained band in FIG. 1.6 is actually a doublet of 4.1 kb fragments, one of which contains the gpt insert). Upon cleavage with both PstI and NotI, the gpt gene cassette was released as a 1.1 kb fragment (FIGS. 1.6 and 1.7, lanes 10).

The patterns of digests obtained with these and other restriction nucleases, including SalI (FIGS. 1.6 and 1.7, lanes 12), are consistent with the interpretation that vp7 is a stable modified virus that has the gpt-gene integrated into the NotI site of the vaccinia virus genome in the "a" orientation (see FIG. 1.11).

A second series of cloning experiments were done under slightly modified conditions (see Table 1 and methods, above). Five different ligation reactions (A-E) were set up containing constant amounts of NotI-cleaved vaccinia vector DNA and increasing amounts of insert DNA. Packaging was done under standard conditions in vaccinia virus-infected CV-1 cells. The titers of gpt-positive vaccinia viruses in all cases were about $1 \times 10^5$ pfu per $8 \times 10^6$ cells. The plaque population in all cloning experiments was heterogeneous in size: about half had a normal size while the other half were smaller than normal.

TABLE 1

Effect of ratio of insert to vector DNA on yield of modified viruses

| | Experiment | | | | |
|---|---|---|---|---|---|
| | A | B | C | D | E |
| NotI-cleaved vector DNA (μg) | 2 | 2 | 2 | 2 | 2 |
| gpt-gene insert (μg) | 0.2 | 0.2 | 0.4 | 0.4 | 0.6 |
| insert molar excess | 17 | 17 | 34 | 34 | 51 |
| T4 ligase (units) | 5 | 15 | 5 | 15 | 15 |
| gpt-positive virus ($10^5$) (pfu/8 × $10^6$ cells) | 1.12 | 0.88 | 0.96 | 0.96 | 1.16 |

Twelve gpt-positive plaques were isolated, four each in three series designated series A, C and E, comprising 8 normal-sized (large) plaques (A1-4 and C1-4) and 4 small plaques (E1-4). Each of these plaques was analyzed by infecting CV-1 cells in gpt-selective medium, isolating total cell DNAs and digesting them with restriction nucleases, separating the fragments by FIGE and blotting the onto a nitrocellulose membrane.

In FIG. 1.8, the NotI-digested DNA samples hybridized with the vaccinia virus DNA probe are shown (A1-4, lanes 1-4; C1-4, lanes 5-8; E1-4, lanes 9-12). Due to overloading of the gel, the bands smeared somewhat but the essential features are clearly visible. The 145 kb and the 45 kb bands provided the main signal. A weak band at about 5 kb of unknown origin can be seen in some of the samples. The 1.1 kb band, comprising the P7.5-promoter-gpt-gene cassette, makes up only 0.6% of the viral genome and contains only 300 bp of hybridizing sequence (i.e., the P7.5 promoter). Therefore, this band was not expected to give a detectable hybridization signal under the conditions used. In a longer exposure of the blot, when the larger bands are heavily overexposed, the 1.1 kb bands did become visible.

As to the nature of the small plaque phenotype, small plaques E1, E3 and E4 produced only weak hybridization signals (FIG. 1.8, lanes 9–12) indicating that the virus in these plaques had not replicated as extensively as those in normal-sized plaques (lanes 1–8), while isolate E2 failed to produce a detectable amount of DNA (lane 10).

The samples shown in FIG. 1.8 were also hybridized with the gpt-gene probe (FIG. 1.9). The expected single hybridization signal was obtained with plaques A1, A4, C1, C2, C4, E3 and E4 (FIG. 1.9, lanes 1, 4, 5, 6, 8, 11 and 12). The plaque A2 (lane 2) had the gpt-gene integrated into the 45 kb band. (The weak signal in the 145 kb band may be due to contamination with a second minor species or to secondary recombination events.) The plaque A3 (lane 3) has gpt-gene sequences integrated into the 145 kb and 45 kb bands, while the plaque C3 (lane 7) has an integration of those sequences into the 145 kb band and into the NotI site. The plaques A2, A3 and C3 are probably recombinants that arose by illegitimate intracellular recombination of homologous sequences present in the model gene cassette insert and in the inverted repetitions of the viral DNA.

As with the vaccinia virus DNA probe, the small plaques E1-E4 produced only weak hybridization signals (FIG. 1.9, lanes 9–12) indicating that the virus in these plaques had not replicated as extensively as those in normal-sized plaques. The wildtype virus DNA and uninfected CV-1 cell DNA did not hybridize with the gpt-gene probe (FIG. 1.9, lanes 13 and 15).

The orientation and copy number of the gpt-gene inserts were determined by digesting the samples shown in FIG. 1.9 with PstI and Southern blot analysis. The expected sizes of new PstI fragments resulting from insertion of the gpt-gene are shown in FIG. 1.11. Hybridization with the gpt-gene probe revealed that the patterns of plaques A1, A4, C1 and C2 (FIG. 1.10 lanes 1, 4, 5 and 6) comprised a single PstI fragment of 4.1 kb as expected for a single insert in the "a" orientation (FIG. 1.11). For plaque E1, a weak hybridization signal from a 21 kb band, which was observed only in long exposures of the blot, was consistent with the "b" orientation of the gpt-gene insert.

The structures of the viral DNAs from plaques C4 and E3 (FIG. 1.10, lanes 8 and 11) were consistent with double tandem inserts in the "b" orientation. In this case hybridizing fragments of 21 and 1.1 kb are expected (FIG. 1.11). The structure of the virus in plaque E4, comprising two fragments of 4.1 and 1.1 kb, is consistent with a tandem insertion of two gpt-genes in the "a" orientation. The DNA from plaques A2, A3 and C3 exhibited more complex patterns indicative of insertions at multiple sites which were not further analyzed.

In summary, in the second cloning experiment five of eight normal-sized plaques had genomic structures expected for insertion of a single gpt-gene cassette into the unique NotI site of the vaccinia virus genome. The slower growing small-sized plaques exhibited unstable structures which were lost during subsequent plaque purification steps.

EXAMPLE 2

Direct molecular cloning of a selective marker gene (*E. coli* gpt) into a unique (NotI) cleavage site of a modified avipoxvirus genome (fowlpox virus clone f-TK2a)

This example illustrates the general applicability of direct molecular cloning of modified cytoplasmic DNA virus genomes by illustrating an application to modified avipoxvirus genomes that are engineered in vitro and packaged in vivo. Avipoxviruses have the largest genomes of the poxvirus family. The genome of fowlpox virus (FPV) is about 300 kb in size, and heretofore FPV recombinants expressing foreign genes have been constructed only by marker rescue techniques [see, for instance, Boyle and Coupar, *Virus Res.* 120: 343–356 (1988); Taylor et al., *Vaccine* 5: 497–503 (1988)].

The present example illustrates production of a modified fowlpox virus by direct molecular cloning of a gene expression cassette consisting of a poxvirus promoter driving the *E. coli* gpt gene into a unique NotI site in the genome of a recombinant fowlpox virus, f-TK2a. This NotI site is located in a lacZ gene which was previously inserted into this recombinant by intracellular recombination. Engineered DNA is packaged in primary chicken embryo fibroblasts infected with the HP2 helper fowlpox virus which replicates more slowly than the f-TK2a recombinant. Selection for gpt-positive plaques leads to isolation of engineered fowlpox viruses. Since the lacZ marker gene is inactivated by an insertion at the NotI site, the progeny virus are distinguished from vector virus lacking an insert, by a colorless phenotype in the blue plaque assay for lacZ gene expression.

Purification of fowlpox virus and DNA: The fowlpox virus (FPV) strain HP1 [Mayr & Malicki, *Zentralblatt f. Veterinarmedizin, Reihe B,* 13:1–12 (1966)]and the attenuated strain HP1.441 (passage number 441 of HP1) were obtained from A. Mayr, Munich. The fowlpox virus strain HP2 was derived from HP1.441 by plaque purification. Primary chicken embryo fibroblasts (CEF) were prepared as described in European patent application publ. #0 338 807. The cells were grown in tissue culture medium 199 (TCM 199; Gibco BRL) supplemented with 5% fetal calf serum, glutamine and antibiotics. Fowlpox virus was purified by two successive sucrose gradients according to Joklik, W. K., *Virology* 18: 9–18 (1962). Viral DNA was prepared by the proteinase K/SDS procedure according to Gross-Bellard et al., *Eur. J. Biochem.* 36:32–38 (1973).

Construction of a fowlpox virus vector (fTK-2a) having a unique (NotI) cleavage site in an inserted DNA segment: The vaccinia virus tk-gene, together with the *E. coli* lacZ gene was inserted into the intergenic region between the tk-gene and the 3'-orf of fowlpox virus. The plasmids pTKm-VVtka and pTKm-VVtkb were constructed by cloning the functional vaccinia virus tk-gene into the intermediate plasmid pTKm-sP11. Upon intracellular recombination of pTKm-VVtka and pTKm-VVtkb with wildtype fowlpox virus DNA two novel FPV vectors, termed f-TK2a and f-TK2b, respectively, were created. Each vector contains two functional tk-genes, the endogenous FPV gene and the inserted vaccinia virus tk-gene, in addition to the inserted lacZ gene, any of which can be used as a nonessential site for insertion of foreign DNA. In particular, the NotI site in the lacZ gene is a unique cleavage site in the f-TK2a and b vectors and, therefore, is advantageous for direct molecular cloning of foreign DNA into these vectors. Complete details of the construction of the fowlpox virus vectors f-TK2a and f-TK2b are disclosed in a U.S. application entitled "Recombinant Fowlpox Virus" by Scheiflinger et al., which claims priority of an equivalent European application filed concurrently with this application, the entire disclosure of which is hereby incorporated herein by reference.

In vivo packaging in avian cells: $8\times10^6$ CEF cells are infected with 0.2 pfu/cell of helper virus (HP2) for 2 h. For packaging engineered FPV genomes, 1 μg of purified ligation reaction product is used. Cells are transfected with DNAs by the calcium phosphate precipitation technique (Graham and van der Eb, 1973) and incubated for 15 min at room temperature. Nine ml medium (TCM 199, 10% fetal calf serum, glutamine and antibiotics) per one ml precipitate are added to the cells. After four hours the medium is changed and further incubated for two days. Crude virus stocks are prepared according to standard procedures (Mackett et al. 1985). Plaque assays and gpt-selection are done as described by Scheiflinger et al., 1991.

Direct molecular cloning into a unique NotI cleavage site of a fowlpox virus genome: The recombinant FPV strain f-TK2a (Scheiflinger et al., 1991) is suitable as a vector for directly cloning a gene cassette, for instance a model gpt gene cassette as described herein, into a unique NotI cleavage site. This NotI site of the vector is in the coding region of a lacZ gene, which serves as a color screening marker that is inactivated upon gene insertion. Thus, lacZ-positive viruses form blue plaques in the presence of the chromogenic substrate X-Gal, while viruses with inserts in this NotI site show a white plaque phenotype. The genome of the fTK-2a vector also has incorporated the vaccinia virus thymidine kinase (tk) gene that also serves as an alternate gene insertion region. Both the lacZ and tk genes were inserted into the fowlpox virus genome in the intergenic region between the fowlpox thymidine kinase gene and the 3'-open reading frame, by conventional methods (Scheiflinger et al., 1991).

Patterns of DNA cleavage by NotI were established for the genomic DNAs of FPV viruses HP1.441 and the vector strain f-TK2a (FIG. 2.1). HP1,441 was derived from a virulent FPV strain through attenuation by serial passage in chicken embryo fibroblasts. HP1.441 is the 441th passage of HP1 and is used as a vaccine strain against fowlpox (Mayr & Malicki, 1966) and is well adapted for rapid replication in cell culture.

DNA from HP1.441 was analyzed as a reference for the FPV vector strain f-TK2a which is a derivative of HP1.441. The restriction analysis of the HP1.441 DNA (FIG. 2.1, lanes 1 and 2) showed that this strain has no NotI sites. Cleavage of vector f-TK2a DNA with NotI resulted in two large fragments of about 100 and 200 kb (FIG. 2.1, lane 4).

Direct molecular construction of a fowlpox virus expressing the gpt gene: A model gene expression cassette comprising the *E. coli* gpt gene was constructed in the plasmid pN2-gpta which contains the gpt gene driven by an early/late poxvirus promoter flanked by NotI sites (FIG. 1.3).

For cloning into the vector f-TK2a, the gpt-gene cassette is excised from its plasmid and ligated with NotI cleaved genomic DNA of f-TK2a as outlined in FIG. 2.2. Ligated DNA is transfected into fowlpox helper virus-infected CEF cells. Gpt-positive plaques that remain white under an overlay containing X-Gal are further analyzed by Southern blotting after infection of chicken embryo fibroblasts. Total cell DNA is isolated and the separated NotI fragments are subjected to Southern blotting with $^{32}$P-labelled DNAs of the helper fowlpox (HP2) and gpt gene sequences, as described in Example 1. Gpt-positive viruses containing the gpt gene on the 1.1 kb NotI fragment indicating that correct ligation has occurred in the cloning step.

Production of modified viruses with both insert orientations in one construction step: The present example also illustrates how viruses having a single copy of the inserted gene cassette in either orientation, as well as viruses containing multiple copies of the inserted gene, can be recovered from a single direct molecular cloning step. The orientation of the DNA insert in selected engineered fowlpox genomes is determined by Southern blotting of DNAs cleaved with appropriate restriction enzymes. As shown in FIG. 2.2, the DNA inserted into a viral DNA may be in either the "a" or "b" orientations. For preliminary analyses of insert number and orientation with the present model gene cassette, for instance, total DNA of cells infected with selected plaques is digested with the restriction endonuclease ClaI and NotI and separated on a 0.8% agarose gel. The blot is hybridized with a gpt gene probe and a fowlpox virus probe.

In the NotI-digested DNA samples of recombinant viruses, the gpt cassette is excised as a 1.1 kb fragment. Cleavage with ClaI of DNAs having an insert in the a or b orientation also results in different characteristic fragments hybridizing with a gpt gene probe, as determined from the structures presented in FIG. 2.2.

EXAMPLE 3

Heterologous packaging of engineered orthopox (vaccinia) virus genomic DNA by an avipox (fowlpox) helper virus and subsequent selection for recombinants in host cells of a species in which the helper virus cannot replicate Heterologous packaging of poxvirus DNA, for instance, packaging of an orthopoxvirus DNA by an avipox virus, has not been reported. However, the present example demonstrates that in vivo packaging of extracellularly engineered vaccinia virus DNA can be achieved by fowlpox virus in chicken embryo fibroblasts. The use of a vector virus having a different host range from that of the helper virus provides a simple and efficient procedure for purifying an engineered virus in one plaque assay step. Thus, in the present example, the recombinant orthopoxvirus was recovered by plaque assay on mammalian (CV-1) cells which do not support full replication of the avipox helper virus. Inclusion of a dominant selective marker in the DNA inserted into the vector advantageously facilitates the use of selective plaque assay conditions for elimination of viruses comprising vector DNA lacking the desired insert.

Another advantage of the heterologous packaging approach is the reduced potential for recombination between vector and helper viruses. For example, orthopox and avipox viruses belong to different genera, have different morphologies and replication facilities, and share only minimal sequence homology as demonstrated by a lack of cross-hybridization under standard hybridization conditions. Therefore, homologous recombination of the genomes of avipox and orthopox viruses is exceedingly unlikely and use of these two viruses can practically eliminate undesirable recombination events that frequently occur between homologous sequences of closely related viruses [Fenner & Comben, *Virology* 5:530–548 (1958); Fenner, *Virology* 8: 499–507 (1959)]. An alternative approach for preventing vector-helper recombination during packaging is to use recombination deficient virus strains or host cells.

In this example, a model expression cassette comprising a marker gene (the *E. coli* gpt gene driven by a poxvirus promoter) was inserted extracellularly into a unique SmaI site of vaccinia virus DNA. The use of this restriction enzyme to cleave the viral DNA produces blunt ends which advantageously may be ligated to blunt-ended DNA inserts prepared by any other nuclease that produces blunt ends, or, for example by using a polymerase or exonuclease to create blunt ends from an insert having single-stranded ends.

For packaging, the engineered genomic DNA was transfected into fowlpox virus-infected host cells in which both vaccinia and fowlpox viruses can replicate (chicken embryo fibroblasts). Since the host range of the fowlpox helper virus is restricted to avian cells, vaccinia virus clones were selected by plaque-purification of progeny from the transfected cells on mammalian host cells (African Green Monkey Kidney CV-1 cells). Simultaneous selection for gpt gene expression was used to isolation of only modified vaccinia viruses. In contrast to the conventional method of producing poxvirus recombinants where in one intracellular genetic cross usually only one copy of a foreign gene can be inserted in a single orientation, in the present example, both possible orientations of a single insert, as well as double insertions of the model gene cassette were identified as products of a single extracellular genomic modification reaction.

The experimental results in the present example show that the packaging efficiency of ligated vaccinia virus DNAs by fowlpox helper virus was low compared to packaging of intact vaccinia virus DNA with fowlpox virus, which produces yields in the range of $5\times10^3$ to $1\times10^4$ pfu per $6\times10^6$ chicken embryo fibroblasts after three days of replication. In one packaging experiment (producing plaques designated the "F12" series, infra) the yield of packaged modified virus was $9\times10^2$ pfu, and in a second experiment (producing the "F13" series), $5\times10^2$ pfu, per $6\times10^6$ chicken cells. One source of this relatively low packaging frequency in these experiments is the lack of dephosphorylation treatment of the vector DNA arms which, therefore, were able to religate efficiently without any insert. Such treatment was omitted because dephosphorylation of blunt-ended DNA fragments is usually inefficient. This problem can be overcome by construction of host virus strains having multiple cleavage sites with "sticky" ends that enable directional ("forced") cloning, thereby making the insertion of foreign DNA fragments much more efficient.

Another factor influencing the packaging efficiency is interference at the cellular level between the helper and the packaged virus. Under standard packaging conditions, within three days of incubation the helper virus (fowlpox) usually replicates to titers of about $1\times10^8$ pfu per $6\times10^6$ chicken embryo fibroblasts. The large excess of fowlpox virus compared to packaged vaccinia virus creates conditions that produce negative interference phenomena and inhibits replication of the packaged virus.

This interference is minimized by using mammalian cells for packaging in combination with fowlpox helper virus as described in Example 7. In that case, the host cells do not support full replication of the helper fowlpox virus. Although, no testing of ligated vaccinia virus DNA for packaging efficiency by fowlpox virus has been made in a mammalian host cell, a packaging yield of $2 \times 10^6$ pfu per $8 \times 10^6$ mammalian (CV-1) cells was obtained with uncleaved vaccinia virus DNA.

In each viral recombinant generated by intracellular recombination with a given insertion plasmid an insert has one orientation depending on the polarity of the homologous flanking regions in that plasmid. Due to transcriptional interference phenomena, for instance (Ink & Pickup, 1989), expression levels for genes inserted into a poxvirus vector depend on the orientation of the foreign gene relative to the viral genome. Therefore, it is desirable to obtain in one reaction step modified viruses having either possible orientation. One of the advantages of the procedure in this example is that both possible orientations of the inserted DNA are obtained in one ligation reaction, allowing immediate screening for variants having the highest expression level. The preferred orientation of the cassette of this example in the selected SmaI insertion site of vaccinia virus is the "b" orientation, as evidenced by the fact that the majority of modified viruses had this genomic structure. In this cassette the P7.5 promoter controlling the foreign gene is in the inverted repeat orientation relative to the endogenous 7.5 kDa polypeptide gene. As discussed in Example 1, the endogenous 7.5 kDa polypeptide genes are located in the inverted terminal repetitions of the vaccinia genome. The distance of the P7.5 promoter of the gpt-gene and the P7.5 promoter in the left terminal repetition is about 20 kb. The "a" orientation should therefore be less stable and less frequently obtained, in accordance with the observation that this orientation was found only twice. However, the viral isolates F13.4 (orientation a) and vF12.5 (orientation b) were propagated to large scale with gpt-selection and were found to have stable predicted structures. The stability of the various structures comprising multiple inserts without selection remains to be determined.

The ligations contained several-fold excess of insert over the vector, thereby favoring insertion of multiple copies of the cassette as observed. However, it is unclear why in this example double insertions were more frequent than in Example 1. Due to internal recombination events only certain configurations of multiple inserts are expected to be stable. Further studies to evaluate stability of viruses with multiple inserts and the optimal ratio of vector to insert for stability and expression level which depends on copy number can all be conducted as necessary for each construct, according to the teachings of this application. Purification of virus and DNA: The viruses and methods of Examples 1 and 2 were used.

Engineering of vital DNA: Viral DNA purified from virions was cleaved with SmaI and purified by one phenol extraction and three chloroform extractions. In the first experiment below, 2 μg of cleaved virus DNA were ligated with 400 ng (34 fold molar excess) of the insert fragment (the 1.1 kb HpaI-DraI fragment excised from plasmid pTKgpt-Fls) in a volume of 30 μl for 40 h with 15 units of T4 ligase (Boshringer, Inc.). The second ligation experiment was done under the same conditions except that a seventeen-fold molar excess of the 1.1 kb SmaI insert and 5 units of ligase were used.

In vivo heterologous packaging in avian cells: Chicken embryo fibroblasts ($6 \times 10^6$) infected with the helper virus (0.5 pfu/cell of HP1.441) and incubated for 2 h. Two μg of ligated DNA was transfected into the infected cells and treated further as described for the homologous packaging procedure in Example 1. The initial plaque assay was done in CV-1 cells as described in Example 1.

Demonstration of packaging of modified vaccinia virus DNA by fowlpox helper virus: The design of this experiment is shown in FIG. 3.1. Vaccinia virus genomic DNA was prepared from sucrose gradient purified virions, cut with the restriction endonuclease SmaI, and ligated with the blunt-ended foreign gene cassette. Ligated DNA was transfected into fowlpox virus-infected chicken embryo fibroblasts for packaging. Progeny virus was identified by plaque assay on mammalian (CV-1) cells which do not support complete replication of fowlpox virus to produce infectious virions.

In more detail, first, the HpaI-DraI fragment bearing the model gene cassette (containing the gpt gene driven by the vaccinia virus P7.5 promoter) was excised from the plasmid pTKgpt-Fls (Falkner & Moss, 1988) and ligated directly into the unique SmaI site of vaccinia wildtype virus (WR strain). The gpt gene was selected to permit positive selection of modified viruses (Boyle & Coupar, 1988; Falkner & Moss, 1988). The single SmaI site in vaccinia virus DNA is located in the open reading frame A51R in the HindIII A fragment of the genome. The A51R gene is non-essential for viral replication in cell culture (Goebel et al., 1990).

Ligated material was transfected into chicken embryo fibroblasts infected with fowlpox helper virus. After three days the cells were harvested and a crude virus stock was prepared. Packaged vaccinia virus was identified by plaque assay on an African Green monkey kidney cell line (CV-1) in medium that selects for cells infected with a virus carrying the gpt gene. This selection scheme prevents viruses containing self-ligated wildtype vaccinia virus DNA from forming plaques while allowing modified viruses containing an inserted model gpt gene cassette to do so.

The packaging frequency was low in initial experiments. The titer of gpt-positive vaccinia virus in the crude stock prepared from $6 \times 10^6$ chicken embryo fibroblasts was in the range of $1 \times 10^2$ to $1 \times 10^3$ pfu.

Thirteen gpt-positive plaques were amplified under gpt-selection in CV-1 cells. Total DNA of infected cells was isolated, digested with HindIII, separated on a 0.7% agarose gel and further processed for analysis by Southern blotting with a gpt-gene probe. As shown in FIG. 3.2, several viruses having blot patterns predicted for different modified genomic structures were obtained.

In lanes 2, 4, 11 and 13 (corresponding to plaques #F12.3, F12.5, F13.3 and F13.5) a single hybridizing fragment of about 45 kb is visible, that is expected when one copy of the gene cassette is inserted into the viral genome in the "b" orientation into the viral genome (see FIG. 3.3). An expected novel fragment of 5.2 kb is also present in all cases, and also appears when the same DNAs are tested as in FIG. 3.2 using a vaccinia virus probe.

Two viruses having patterns consistent with the "a" orientation were obtained in lanes 7 and 12 (corresponding to plaques #F12.8 and F13.4), where a single gpt-hybridizing fragment of about 5.7 kb is expected. The 5.7 kb fragment in lane 7 is more visible in longer exposures of the autoradiograph. The pattern seen in lane 5 (plaque F12.6) may represent a single insert in the "a" orientation, but the expected 5.7 kb band is somewhat larger for unknown reasons.

The pattern of three viral isolates is consistent with a tandem insertion in the "a" orientation (lanes 1, 6 and 10, corresponding to plaques #F12.2, F12.7 and F13.2). In these cases two gpt-positive hybridizing fragments, of 5.7 and 1.1 kb, are expected (see also FIG. 3.3). Fragments of 5.7 and 1.1 kb were also observed in equimolar amounts with the viral DNA in a blot hybridized with a vaccinia virus probe.

The genome of the isolate in lane 3 (plaque F12.4) probably contains a tandem duplicate insert in the "b" orientation. In this case two fragments, of 45 kb and 1.1 kb, are expected to hybridize with the gpt-gene.

The viral DNA in lane 9 (plaque F13.1) may comprise a head-to-head double insertion. In this case a 45 kb and a 5.7 kb fragment hybridizing with a gpt-gene probe are expected. However, in addition such a DNA should contain a novel 0.6 kb fragment that hybridizes with a vaccinia DNA probe, and, in fact, this fragment was detected on a blot hybridized with a vaccinia probe. Nevertheless, the expected 5.7 kb fragment was somewhat smaller than predicted and produced a hybridization signal that was weaker than expected. Therefore, confirmation of the structure of this recombinant requires more detailed analysis.

EXAMPLE 4

Construction of an orthopoxvirus (vaccinia) vector (vdTK) with a directional master cloning site and plasmids with compatible expression cassettes This example demonstrates application of the methods of the present invention to create novel poxvirus cloning vectors by direct molecular modification and cloning of existing poxvirus genomes. In particular, this example describes a vaccinia virus vector (vdTK) which allows directional insertion (i e., "forced cloning") of foreign genes into a short "multiple cloning site" segment comprised of several different endonuclease cleavage sites each of which is unique in the vector genome. Forced cloning eliminates the need for selection or screening procedures to distinguish the desired recombinants from vector virus lacking an insert because incompatibility of DNA ends cleaved by different nucleases prevents religation of the vector arms without a foreign insert. Consequently, the forced cloning approach is the most efficient way to insert a foreign gene into a viral vector.

The directional vector vdTK is created by inserting a multiple cloning site (comprised of unique NotI, SmaI, ApaI and RsrII sites) in place of the thymidine kinase (tk) gene of vaccinia virus (see FIG. 4.1A). This nonessential locus is the site most frequently used for insertion of foreign genes into vaccinia virus, mainly because positive selection for tk-negative viruses is available. Thus, when ligated vdTK vector DNA is packaged by a tk-positive helper virus, the vector virus may be positively selected from the excess of helper virus. Further, insertion of foreign DNA into the vaccinia virus tk-locus by conventional methods generally results in stable recombinants.

The multiple cloning site of the new vdTK vector is comprised of NotI and SmaI cleavage sites which are unique in the vector. Prior to insertion of the multiple cloning site, NotI and SmaI cleavage sites preexisting in the wildtype vaccinia virus (WR strain) are deleted by direct molecular modifications according to the present invention. Viruses having the desired modifications are detected by screening techniques based on the polymerase chain reaction (PCR) method for amplification of specific nucleic acid sequences.

This example also describes a set of plasmids which facilitate expression of DNAs encoding complete or partial open reading frames in the vdTK vaccinia vector. The present invention comprehends insertion of open reading frames directly into a poxvirus expression vector having all appropriate regulatory elements suitably placed for expression of the inserted open reading frame. However, the instant vdTK vector is not equipped with such regulatory sequences for expression of an inserted open reading frame that lacks its own transcription and translation signals. Accordingly, the plasmids of this example provide convenient gene expression cassettes for routine linkage of open reading frames to poxvirus promoters and, optionally, to a translation start codon. An open reading frame and associated regulatory sequences are then efficiently transferred into the vdTK vector master cloning site by forced cloning. Modified viruses having the insert in either orientation can be obtained by using one of two plasmids having the expression cassette in the desired orientation within its master cloning site. The gene expression cassettes of the plasmids exemplified here have two nested sets of restriction enzyme cleavage sites to facilitate cloning of open reading frames into the vdTK vector. The cassettes have a master cloning site comprised of the same unique sites as the master cloning site of the vdTK vector. In addition, in the middle of this master cloning site the cassettes contain a variety of sites for frequently cutting enzymes that are useful for insertion of open reading frames into the cassettes. Thus, DNAs inserted into a cassette by means of the frequent cutter sites are flanked on either side by several different unique sites which are suitable for forced cloning of the cassette into the master cloning site of the vdTK vector.

This example also describes gene expression cassettes suitable for insertion into a single unique site in the vaccinia virus vector vdTK. To overcome the reduced cloning efficiency of using a single enzyme for cleaving the vector DNA, the expression cassettes of these plasmids include the E. coli gpt gene as a selective marker.

The vdTK vaccinia vector system is preferentially used in conjunction with the heterologous packaging procedure described in Example 3. The plasmids containing the gpt marker can also be used with homologous helper virus lacking the gpt marker. Examples of constructs for expression of polypeptides using the vdTK vector and related plasmid system are presented hereinbelow in Example 5.

In addition to the above advantages, the expression cassette plasmids of this invention also provide a means of overcoming a general problem of incompatibility between the ends of cleaved poxvirus vector DNAs and many insert DNAs, as a convenient alternative to the common use of synthetic adaptor DNA segments. Thus, isolation of DNA fragments encoding open reading frames usually is facilitated by use of restriction endonucleases having recognition sequences which are short and, consequently, randomly occur at high frequencies in all natural DNA sequences. On the other hand, such frequently cutting enzymes generally are not suitable for efficient direct cloning into genomes as large as those of poxviruses, for instance, because such enzymes cleave large DNAs into many fragments. Religation of these fragments would occur in random order, producing few intact viral genomes. Therefore, insertion sites in a vaccinia vector preferably are cleavage sites of infrequently cutting restriction endonucleases which are unlikely to be used for isolation of open reading frame fragments or insert DNAs in general. The present plasmids overcome this general incompatibility by allowing efficient insertion of fragments from frequent cutters into the plasmid followed by efficient transfer into the vaccinia vector using infrequently cutting enzymes.

Deletion of the unique NotI cleavage site from wildtype vaccinia (WR) virus: The unique NotI site of vaccinia virus may be eliminated by insertion into this site of a "NotI deletion adaptor" segment having cohesive ends compatible for ligation with NotI-cleaved DNA but lacking sequences required for recognition by the NotI endonuclease. Thus, the sequences formed by the ligated cohesive ends of the NotI-cleaved viral DNA and viral DNA and adaptor are not cleavable by NotI. This adaptor also contains several selected restriction endonuclease cleavage sites for directed insertion of DNA fragments.

More particularly, one μg of vaccinia virus WR wild type DNA is cut with NotI and ligated with one μg of the double-stranded NotI-deletion adaptor. The adaptor consists of two partially complementary strands: odN1 (SEQ. ID. NO. 16) and odN2 (SEQ. ID. NO. 23). The central part of the adaptor contains the restriction endonuclease cleavage sites StuI, DraI, SspI and EcoRV. Annealed adaptor oligonucleotides are used for the ligation reaction. The ligated material is transfected into fowlpox virus-infected chicken embryo fibroblasts and packaged as described in Examples 3 and 7.

An alternative procedure for deleting the single NotI site of vaccinia virus (WR strain) is outlined in FIG. 4.1, panel B. In the first step, vaccinia virus DNA is cut with SacI, the SacI "I" fragment is isolated from low melting point agarose and cloned into the SacI site of a suitable plasmid, such as pTZ1gR (obtainable from Pharmacia, Inc.). The resulting plasmid, pTZ-SacI, is cut with NotI, treated with Klenow polymerase to fill in the sticky ends and religated. The ligated material is transfected into E. coli cells (HB101). The colonies are isolated according to standard cloning procedures. The resulting plasmid, pTZ-SacIdN has the NotI site deleted and is used in a reverse gpt-selection experiment as described by Isaacs, S. N.. Kotwal, G. & Moss B. Virology 178: 626–630 (1990), modified as follows:

CV-1 cells ($8 \times 10^6$) are infected with 0.2 pfu of the recombination with a given insertion plasmid an insert has one orientation depending on the polarity of the homologous flanking regions in that plasmid. Due to transcriptional interference phenomena, for instance (Ink & Pickup, 1989), expression levels for genes inserted into a poxvirus vector depend on the orientation of the foreign gene relative to the viral genome. Therefore, it is desirable to obtain in one reaction step modified viruses having either possible orientation. One of the advantages of the procedure in this example is that both possible orientations of the inserted DNA are obtained in one ligation reaction, allowing immediate screening for variants having the highest expression level. The preferred orientation of the cassette of this example in the selected SmaI insertion site of vaccinia virus is the "b" orientation, as evidenced by the fact that the majority of modified viruses had this genomic structure. In this cassette the P7.5 promoter controlling the foreign gene is in the inverted repeat orientation relative to the endogenous 7.5 kDa polypeptide gene. As discussed in Example 1, the endogenous 7.5 kDa polypeptide genes are located in the inverted terminal repetitions of the vaccinia genome. The distance of the P7.5 promoter of the gpt-gene and the P7.5 promoter in the left terminal repetition is about 20 kb. The "a" orientation should therefore be less stable and less frequently obtained, in accordance with the observation that this orientation was found only twice. However, the viral isolates vF13.4 (orientation a) and vF12.5 (orientation b) were propagated to large scale with gpt-selection and were found to have stable predicted structures. The stability of the various structures multiple insertions without gpt-selection remains to be determined.

The ligations contained several-fold excess of insert over the vector, thereby favoring insertion of multiple copies of the cassette as observed. However, it is unclear why in this example double insertions were more frequent than in Example 1. Due to internal recombination events only certain configurations of multiple inserts are expected to be stable. Further studies to evaluate stability of viruses with multiple inserts and the optimal ratio of vector to insert for stability and expression level which depends on copy number can all be conducted as necessary for each construct, according to the teachings of this application.

Purification of virus and DNA: The viruses and methods of Examples 1 and 2 were used.

Engineering of viral DNA: Viral DNA purified from virions was cleaved with SmaI and purified by one phenol extraction and three chloroform extractions. In the first experiment below, 2 μg of cleaved virus DNA were ligated with 400 ng (34 fold molar excess) of the insert fragment (the 1.1 kb HpaI-DraI fragment excised from plasmid pTKgpt-Fls) in a volume of 30 μl for 40 h with 15 units of T4 ligase (Boehringer, Inc.). The second ligation experiment was done under the same conditions except that a seventeen fold molar excess of the 1.1 kb SmaI insert and 5 units of ligase were used.

In vivo heterologous packaging in avian cells: Chicken embryo fibroblasts ($6 \times 10^6$) infected with the helper virus (0.5 pfu/cell of HP1.441) and incubated for 2 h. Two μg of ligated DNA was transfected into the infected cells and treated further as described for the homologous packaging procedure in Example 1. The initial plaque assay was done in CV-1 cells as described in Example 1.

Demonstration of packaging of modified vaccinia virus DNA by fowlpox helper virus: The design of this experiment is shown in FIG. 3.1. Vaccinia virus genomic DNA was prepared from sucrose gradient purified virions, cut with the restriction endonuclease SmaI, and ligated with the blunt-ended foreign gene cassette. Ligated DNA was transfected into fowlpox virus-infected chicken embryo fibroblasts for packaging. Progeny virus was identified by plaque assay on mammalian (CV-1) cells which do not support complete replication of fowlpox virus to produce infectious virions.

In more detail, first, the HpaI-DraI fragment bearing the model gene cassette (containing the gpt gene driven by the vaccinia virus P7.5 promoter) was excised from the plasmid pTKgpt-Fls (Falkner & Moss, 1988) and ligated directly into the unique SmaI site of vaccinia wildtype virus (WR strain). The gpt gene was selected to permit positive selection of modified viruses (Boyle & Coupar, 1988; Falkner & Moss, 1988). The single SmaI site in vaccinia virus DNA is located in the open reading frame A51R in the HindIII A fragment of the genome. The A51R gene is non-essential for viral replication in cell culture (Goebel et al., 1990).

Ligated material was transfected into chicken embryo fibroblasts infected with fowlpox helper virus. After three days the cells were harvested and a crude virus stock was prepared. Packaged vaccinia virus was identified by plaque assay on an African Green monkey kidney cell line (CV-1) in medium that selects for cells infected with a virus carrying the gpt gene. This selection scheme prevents viruses containing self-ligated wildtype vaccinia virus DNA from forming plaques while allowing modified viruses containing an inserted model gpt gene cassette to do so.

The packaging frequency was low in initial experiments. The titer of gpt-positive vaccinia virus in the crude stock prepared from $6 \times 10^6$ chicken embryo fibroblasts was in the range of $1 \times 10^2$ to $1 \times 10^3$ pfu.

Thirteen gpt-positive plaques were amplified under gpt-selection in CV-1 cells. Total DNA of infected cells was isolated, digested with HindIII, separated on a 0.7% agarose gel and further processed for analysis by Southern blotting with a gpt-gene probe. As shown in FIG. 3.2, several viruses having blot patterns predicted for different modified genomic structures were obtained.

In lanes 2, 4, 11 and 13 (corresponding to plaques #F12.3, F12.5, F13.3 and F13.5) a single hybridizing fragment of about 45 kb is visible, that is expected when one copy of the gene cassette is inserted into the viral genome in the "b" orientation into the viral genome (see FIG. 3.3). An expected novel fragment of 5.2 kb is also present in all cases, and also appears when the same DNAs are tested as in FIG. 3.2 using a vaccinia virus probe.

Two viruses having patterns consistent with the "a" orientation were obtained in lanes 7 and 12 (corresponding to plaques #F12.8 and F13.4), where a single gpt-hybridizing fragment of about 5.7 kb is expected. The 5.7 kb fragment in lane 7 is more visible in longer exposures of the autoradiograph. The pattern seen in lane 5 (plaque F12.6) may represent a single insert in the "a" orientation, but the expected 5.7 kb band is somewhat larger for unknown reasons.

The pattern of three viral isolates is consistent with a tandem insertion in the "a" orientation (lanes 1, 6 and 10, corresponding to plaques #F12.2, F12.7 and F13.2). In these cases two gpt-positive hybridizing fragments, of 5.7 and 1.1 kb, are expected (see also FIG. 3.3). Fragments of 5.7 and 1.1 kb were also observed in equimolar amounts with the viral DNA in a blot hybridized with a vaccinia virus probe.

The genome of the isolate in lane 3 (plaque F12.4) probably contains a tandem duplicate insert in the "b" orientation. In this case two fragments, of 45 kb and 1.1 kb, are expected to hybridize with the gpt-gene.

The viral DNA in lane 9 (plaque F13.1) may comprise a head-to-head double insertion. In this case a 45 kb and a 5.7 kb fragment hybridizing with a gpt-gene probe are expected. However, in addition such a DNA should contain a novel 0.6 kb fragment that hybridizes with a vaccinia DNA probe, and, in fact, this fragment was detected on a blot hybridized with a vaccinia virus probe. Nevertheless, the expected 5.7 kb fragment was somewhat smaller than predicted and produced a hybridization signal that was weaker than expected. Therefore, confirmation of the structure of this recombinant requires more detailed analysis.

EXAMPLE 4

Construction of an orthopoxvirus (vaccinia) vector (vdTK) with a directional master cloning site and plasmids with compatible expression cassettes This example demonstrates application of the methods of the present invention to create novel poxvirus cloning vectors by direct molecular modification and cloning of existing poxvirus genomes. In particular, this example describes a vaccinia virus vector (vdTK) which allows directional insertion (i.e., "forced cloning") of foreign genes into a short "multiple cloning site" segment comprised of several different endonuclease cleavage sites each of which is unique in the vector genome. Forced cloning eliminates the need for selection or screening procedures to distinguish the desired recombinants from vector virus lacking an insert because incompatibility of DNA ends cleaved by different nucleases prevents religation of the vector arms without a foreign insert. Consequently, the forced cloning approach is the most efficient way to insert a foreign gene into a vital vector.

The directional vector vdTK is created by inserting a multiple cloning site (comprised of unique NotI, SmaI, ApaI and RsrII sites) in place of the thymidine kinase (tk) gene of vaccinia virus (see FIG. 4.1A). This nonessential locus is the site most frequently used for insertion of foreign genes into vaccinia virus, mainly because positive selection for tk-negative viruses is available. Thus, when ligated vdTK vector DNA is packaged by a tk-positive helper virus, the vector virus may be positively selected from the excess of helper virus. Further, insertion of foreign DNA into the vaccinia virus tk-locus by conventional methods generally results in stable recombinants.

The multiple cloning site of the new vdTK vector is comprised of NotI and SmaI cleavage sites which are unique in the vector. Prior to insertion of the multiple cloning site, NotI and SmaI cleavage sites preexisting in the wildtype vaccinia virus (WR strain) are deleted by direct molecular modifications according to the present invention. Viruses having the desired modifications are detected by screening techniques based on the polymerase chain reaction (PCR) method for amplification of specific nucleic acid sequences.

This example also describes a set of plasmids which facilitate expression of DNAs encoding complete or partial open reading frames in the vdTK vaccinia vector. The present invention comprehends insertion of open reading frames directly into a poxvirus expression vector having all appropriate regulatory elements suitably placed for expression of the inserted open reading frame. However, the instant vdTK vector is not equipped with such regulatory sequences for expression of an inserted open reading frame that lacks its own transcription and translation signals. Accordingly, the plasmids of this example provide convenient gene expression cassettes for routine linkage of open reading frames to poxvirus promoters and, optionally, to a translation start codon. An open reading frame and associated regulatory sequences are then efficiently transferred into the vdTK vector master cloning site by forced cloning. Recombinants having the insert in either orientation can obtained by using one of two plasmids having the expression cassette in the desired orientation within its master cloning site.

The gene expression cassettes of the plasmids exemplified here have two nested sets of restriction enzyme cleavage sites to facilitate cloning of open reading frames into the vdTK vector. The cassettes have a master cloning site comprised of the same unique sites as the master cloning site of the vdTK vector. In addition, in the middle of this master cloning site the cassettes contain a variety of sites for frequently cutting enzymes that are useful for insertion of open reading frames into the cassettes. Thus, DNAs inserted into a cassette by means of the frequent cutter sites are flanked on either side by several different unique sites which are suitable for forced cloning of the cassette into the master cloning site of the vdTK vector.

This example also describes gene expression cassettes suitable for insertion into a single unique site in the vaccinia virus vector vdTK. To overcome the reduced cloning efficiency of using a single enzyme for cleaving the vector DNA, the expression cassettes of these plasmids include the *E. coli* gpt gene as a selective marker.

The vdTK vaccinia vector system is preferentially used in conjunction with the heterologous packaging procedure described in Example 3. The plasmids containing the gpt marker can also be used with homologous helper virus lacking the gpt marker. Examples of constructs for expression of polypeptides using the vdTK vector and related plasmid system are presented hereinbelow in Example 5.

In addition to the above advantages, the expression cassette plasmids of this invention also provide a means of overcoming a general problem of incompatibility between the ends of cleaved poxvirus vector DNAs and many insert DNAs, as a convenient alternative to the common use of synthetic adaptor DNA segments. Thus, isolation of DNA fragments encoding open reading frames usually is facilitated by use of restriction endonucleases having recognition sequences which are short and, consequently, occur randomly at high frequencies in all natural DNA sequences. On the other hand, such frequently cutting enzymes generally are not suitable for efficient direct cloning into genomes as large as those of poxviruses, for instance, because such enzymes cleave large DNAs into many fragments. Religation of these fragments would occur in random order, producing few intact viral genomes. Therefore, insertion sites in a vaccinia vector preferably are cleavage sites of infrequently cutting restriction endonucleases which are unlikely to be used for isolation of open reading frame fragments or insert DNAs in general. The present plasmids overcome this general incompatibility by allowing efficient insertion of fragments from frequent cutters into the plasmid followed by efficient transfer into the vaccinia vector using infrequently cutting enzymes.

Deletion of the unique NotI cleavage site from wild-type vaccinia (WR) virus: The unique NotI site of vaccinia virus may be eliminated by insertion into this site of a "NotI deletion adaptor" segment having cohesive ends compatible for ligation with NotI-cleaved DNA but lacking sequences required for recognition by the NotI endonuclease. Thus, the sequences formed by the ligated cohesive ends of the NotI-cleaved viral DNA and adaptor are not cleavable by NotI. This adaptor also contains several selected restriction endonuclease cleavage sites for directed insertion of DNA fragments.

More particularly, one $\mu$g of vaccinia virus WR wild type DNA is cut with NotI and ligated with one $\mu$g of the double-stranded NotI-deletion adaptor. The adaptor consists of two partially complementary strands: odN1 (SEQ. ID. NO. 16) and odN2 (SEQ. ID. NO. 23). The central part of the adaptor contains the restriction endonuclease cleavage sites StuI, DraI, SspI and EcoRV. Annealed adaptor oligonucleotides are used for the ligation reaction. The ligated material is transfected into fowlpox virus-infected chicken embryo fibroblasts and packaged as described in Examples 3 and 7.

An alternative procedure for deleting the single NotI site of vaccinia virus (WR strain) is outlined in FIG. 4.1, panel B. In the first step, vaccinia virus DNA is cut with SacI, the SacI "I" fragment is isolated from low melting point agarose and cloned into the SacI site of a suitable plasmid, such as pTZ1gR (obtainable from Pharmacia, Inc.). The resulting plasmid, pTZ-SacI, is cut with NotI, treated with Klenow polymerase to fill in the sticky ends and religated. The ligated material is transfected into *E. coli* cells (HB101). The colonies are isolated according to standard cloning procedures. The resulting plasmid, pTZ-SacIdN has the NotI site deleted and is used in a reverse gpt-selection experiment as described by Isaacs, S. N.. Kotwal, G. & Moss B. *Virology* 178: 626–630 (1990), modified as follows:

CV-1 cells ($8 \times 10^6$) are infected with 0.2 pfu of the viral isolate vp7, a vaccinia virus that has integrated into the single NotI site a gpt-gene cassette (see Example 1). Subsequently, a calcium-phosphate precipitate containing 20 $\mu$g of DNA from the modified SacI fragment prepared from the plasmid pTZ-SacIdN is transfected into the cells. The cells are further treated as described in the packaging procedure in Example 1. Crude virus stocks are used to infect mouse STO cells (obtained from the American Type Culture Collection, Rockville, Md.; ATCC# CRL 1503) in the presence of 6-thioguanine (6TG). This is a negative selection procedure that requires the loss of the gpt-gene for a virus to replicate (Isaacs et al., 1990) and, therefore, leads in the present case to integration of the modified SacI "I" fragment and, thereby, deletion of the gpt gene. All plaques growing in the presence of 6-TG should lack the gpt gene and contain a modified SacI F fragment. The estimated yield is in the range of 0.1–0.2% of the total plaques (i.e., the normal frequency of recombinants in this type of marker rescue experiment). Since the selection procedure is extremely efficient (Isaacs et al., 1990) identification of the correct structures is not expected to require examination of large numbers of clones. However, whether the first procedure above or this alternative procedure is used to delete the single NotI of vaccinia virus, the following screening procedure may be used to identify the desired construct.

Identification by PCR-screening of virus (vdN) having the NotI site deleted: Vaccinia virus clones having the NotI site deleted may be identified by analysis of plaques growing in a cell line (CV-1) that does not support the growth of the fowlpox helper virus. The DNAs of viruses in individual plaques are analyzed by a PCR-based screening method, as follows.

The first primer for the PCR reaction is the oligonucleotide odN1, (SEQ. ID. NO. 16), and the second primer was odN3 (SEQ. ID. NO. 24). The sequence of second primer is located in the vaccinia virus genome about 770 bp downstream of the first primer sequence. The template is total DNA from $1 \times 10^6$ CV-1 cells infected with half the virus of a single plaque. DNA is prepared by standard techniques and about 50 ng is used for the PCR reaction. The PCR reactions are carried out according to standard techniques using commercially available PCR kits. Positive PCR reactions produce a DNA fragment of about 770. Such a virus having the NotI site deleted is designated "vdN".

Deletion of the unique SmaI restriction site from vaccinia virus vdN: The WR strain of vaccinia virus contains a single SmaI site in an open reading frame (A51R) which is not essential for virus replication in cell cultures (Goebel et al., 1990). Although this site may be used for foreign gene insertion, in the present example, however, this site is deleted in favor of creating a more versatile vaccinia virus vector by introducing a new unique SmaI site as part of a multiple cloning site cassette.

Accordingly, vdN virus DNA (1 μg) is cut with SmaI and ligated with an excess of a hexamer linker having the recognition sequence for the restriction nuclease HindIII (odS1, 5'-AAGCTT-3'). Insertion of this linker into the vaccinia virus SmaI cleavage site results in destruction of the SmaI recognition sequence and the introduction of a new HindIII recognition sequence. The ligated material is packaged by transfection into chicken embryo fibroblasts that have been infected with fowlpox virus, as described in Example 7.

Alternatively, the single SmaI site of vaccinia virus (WR strain) is deleted according to the procedure outlined in FIG. 4.1, panel C, by modifying a cloned fragment of vaccinia virus DNA instead of directly modifying the complete vaccinia virus DNA. In a first step, vaccinia virus DNA is cut with SalI, the SalI F-fragment is isolated from low melting point agarose and cloned into the SalI site of a suitable plasmid, such as pTZgR (obtainable from Pharmacia, Inc.). The resulting plasmid, pTZ-SalF, has two SmaI sites, one in a multiple cloning site and the other in the vaccinia sequences (FIG. 4.1, panel C). pTZ-SalF is partially digested with SmaI and I-SceI linkers are added, as follows: first strand, I-SceI linker 1 (SEQ. ID. NO. 25) and its complementary strand, ISceI linker 2 (SEQ. ID. NO. 26). The correct plasmid having the SmaI site deleted from the vaccinia sequences is identified by cleavage with SmaI and I-SceI. The final plasmid, pTZ-SalFdS, is used to introduce the SmaI deletion into a vaccinia virus genome using the reverse gpt-gene selection experiment as described for deletion of the NotI site, except that preferred virus to be modified is the isolate F12.5, a virus that has integrated into the single SmaI site a gpt-gene cassette (see Example 3).

The resulting insertion of a site for endonuclease I-SceI advantageous for direct molecular cloning because this enzyme, isolated from yeast, recognizes an 18mer site and, therefore, cuts random DNA sequences extremely infrequently. For instance, I-SceI cuts the yeast genome only once. Thierry, A., Perrin, A., Boyer, J., Fairhead, C., Dujon, B., Frey, B. & Schmitz, G. *Nucleic Acids Res.* 19: 189–190 (1991). I-SceI is commercially available from Boehringer, Inc. Advantageously, an I-SceI site is introduced into a vector having no preexisting sites for that enzyme, thereby creating a new vector with a single site that can be used for gene insertions. Whether a vaccinia virus DNA or other vector DNA contains a site for I-SceI cleavage can be determined by routine restriction analyses of the vector DNA.

Where this alternative procedure for deletion of the SmaI site from vaccinia virus DNA is used, the order of steps for constructing the vector vdTK is as follows: deletion of the SmaI site resulting in virus vdS (see above); deletion of the NotI site by insertion of the NotI gpt-gene cassette (see Example 1) into the single NotI site of vdS by cloning and packaging, resulting in the virus vdSNgpt and reverse gpt-selection as described above, using vdSNgpt and pTZ-SacIdN as substrates for the marker rescue experiment; and deletion of the tk-gene as outlined in below in the present example.

Identification by PCR-screening of virus (vdSN) having the SmaI site deleted: Clones of the vdSN vaccinia virus having the SmaI site deleted are identified by PCR screening as follows.

The first primer for the PCR reaction is the oligonucleotide odS2 (SEQ. ID. NO. 27) and the second primer is the oligonucleotide odS3 (SEQ. ID. NO. 28). The sequence of oligonucleotide odS2 is located in the vaccinia genome about 340 bp upstream of the SmaI site, while that of oligonucleotide odS3 is located about 340 bp downstream of this site. The template is total DNA of CV-1 cells infected with a virus plaque as described above for vdN identification. The PCR-amplified band of about 680 bp is tested for susceptibility to SmaI, with resistance to SmaI cleavage indicating insertion of the HindIII or I-SceI linker, while wildtype control DNA is cut into two pieces of about 340 bp. A vaccinia virus having the desired insertion of a linker in the SmaI site is designated vdSN.

Deletion of the coding region of the thymidine kinase gene from vaccinia virus vdSN: From vaccinia virus vdSN, a novel vector strain (designated vdTK) is developed by replacing the thymidine kinase (tk) gene, which is located in a genetically stable region of the vaccinia genome, with a segment comprised of several unique restriction endonuclease cleavage sites (FIG. 4.1A).

The thymidine kinase (tk) coding sequence is first deleted from a plasmid (pHindJ-1) comprising a segment of the vaccinia genome (the HindIII J segment) in which the tk gene is located (see FIG. 4.2). In place of the tk-gene, a multiple cloning site with the unique sites NotI, SmaI, ApaI and RsrII, flanked by SfiI sites is then inserted. Finally, the modified virus segment is transferred into the vaccinia virus genome vdSN which was then designated vdTK (FIG. 4.1A). To further facilitate forced cloning, each of the two SfiI sites also may be made unique in the vector by exploiting the variable nature of the SfiI recognition sequence (GGCCNNNN'NGGCC). The sequences of two SfiI sites are as follows: SfiI(1), GGCCGGCT'AGGCC (SEQ. ID. NO. 29) and SfiI(2), GGCCATAT'AGGCC (SEQ. ID. NO. 30). This plasmid containing the final modification of the tk gene (pHindJ-3) is constructed from precursor plasmid pHindJ-1 by loop-out mutagenesis, and deletion of the tk-gene is confirmed by sequence analysis.

Construction of precursor plasmid pHindJ-1: Vaccinia wildtype virus DNA was cut with HindIII and the resulting fragments were separated on a 0.8% low melting point agarose gel. The HindIII J fragment was excised under UV-light and prepared according to standard techniques. The fragment was inserted into the single HindIII site of the plasmid pTZ19R (Pharmacia, Inc.) resulting in pHindJ-1.

Construction of plasmid pHindJ-2: Plasmid pHindJ-1 is transfected into *E. coli* strain NM522 and single-stranded DNA is prepared by superinfection with the helper phage M13K07 according to the protocol supplied by Pharmacia. The single-stranded DNA serves as the template for site directed mutagenesis with the primer odTK1 (SEQ. ID. NO. 31). This primer is complementary to the promoter region and the region around the translational stop codon of the tk-gene. In its central part it contains the unique restriction sites BamHI, HpaI, NruI and EcoRI. The mutagenesis procedure is carried out with a mutagenesis kit provided by Amersham, Inc., according to the manual provided by the supplier.

For construction of pHindJ-2, the tk-gene sequence has been described in Weir J. P. & Moss B. *J. Virol.* 46:530–537 (1983). The tk-gene sequence is accessible in the EMBL Data Library under the identifier (ID) PVHINLJ. The sequence of the vector part (pTZ19R) of the plasmid is available from Pharmacia, Inc. The sequence around the deleted vaccinia virus thymidine kinase (tk)-gene in the plasmid pHindJ-2 is shown in SEQ. ID. NO. 4. The 5' region of the tk-gene (bases #1–19 in the present listing; bases #4543-#4561 in ID PVHINLJ) is followed by the unique restriction sites BamHI, HpaI, NruI and EcoRI and the 3' region of the tk-gene (bases #44–#67 present listing; bases #5119-#5142 in ID PVHINLJ). Bases #4562 to 5118 in ID PVHINLJ, which contain part of the tk-promoter and the tk-gene coding region, are deleted in pHindJ-2.

Construction of the plasmid pHindJ-3: Plasmid pHindJ-2 is digested with BamHI and EcoRI and a double-stranded linker containing the unique restriction sites NotI, SmaI, RsrII and ApaI, flanked by SfiI sites is inserted. The linker consists of oligonucleotides P-J(1) (SEQ. ID. NO. 32) and P-J(2) (SEQ. ID. NO. 33).

The modified sequence of pHindJ-3 is shown in SEQ. ID. NO. 5. The inserted multiple cloning site corresponds to oligonucleotide P-J(1). The inserted sequence starts at position 21 and ends at position 99. The flanking sequences are the same as described in pHindJ-2, supra.

To insert the tk-deletion into vaccinia virus, plasmid pHindJ-3 is digested with HindIII and a shortened HindIII J fragment having a tk-gene deletion is used for a marker rescue experiment as described by Sam and Dumbell, 1981. Viruses having the tk-gene deleted are isolated by tk-negative selection (Mackett et al., 1982) and identified by subsequent PCR screening.

More particularly, the modified HindIII fragment present in pHindJ-3 is excised with HindIII and isolated with a low melting point agarose gel. The marker rescue is performed essentially as described by Sam and Dumbell (1981) with the following modifications. $5 \times 10^6$ CV-1 cells are infected with 0.2 pfu per cell of vaccinia virus vdSN. After one hour of incubation, one ml of a calcium-phosphate precipitate containing 1 $\mu$g of the modified HindIII J fragment is transfected into the infected cells. After two days growth a crude virus stock is prepared as described in Example 1 and titrated on human 143B tk-negative cells in the presence of bromodeoxy-uridine (BrdU) as described by Mackett et al., 1982. Tk-negative plaques may be further analyzed by PCR screening.

Identification of the thymidine kinase deletion virus (vdTK) by PCR-screening: The first primer for the PCR reaction is oligonucleotide odTK2 (SEQ. ID. NO. 34), the sequence of which is located about 300 bp upstream of the tk-gene. The second primer, odTK3 (SEQ. ID. NO. 35), is located about 220 bp downstream of the stop codon of the tk-gene. The template is total DNA of CV-1 cells infected with a virus plaque, as described for vdN screening. The amplification product resulting from virus having the tk-gene deletion is about 520 bp, while the wildtype control produces a fragment of about 1.1 kb.

Construction of plasmids comprising gene expression cassettes for transfer to the vdTK vector: The plasmid pA0 is the basic plasmid that contains a master cloning site comprised of the unique sites of the master cloning site of the vdTK vaccinia virus vector. Plasmid pA0 was constructed by replacing the multiple cloning site of a commercially available plasmid with a segment comprised of the unique sites of the vdTK vector and an XhoI site, as illustrated in FIG. 4.3.

More in particular, to delete the multiple cloning site of the pBluescript II SK- phagemid (Stratagene), the plasmid was digested with SacI and Asp718. The large vector fragment was ligated with an adaptor consisting of the annealed oligonucleotides P-A(0.1) (SEQ. ID. NO. 36) and P-A(0.2) (SEQ. ID. NO. 37).

The multiple cloning site of pA0 (corresponding to the oligonucleotide P-A(0.1)) and twenty bases of the 5'- and 3'-flanking regions of pBluescriptII SK- are shown in SEQ. ID. NO. 6. The insert starts at position 21 and ends at position 95. (The first "A" residue at the 5'-end corresponds to position number 2187, the last "G" residue at the 3'-end corresponds to position number 2301 of the plasmid pA0).

Construction of the plasmids paI and pA2: The plasmids paI and pA2 were designed for insertion of DNA segments, e.g., synthetic or natural promoter fragments. They were constructed by inserting into the XhoI site of pA0 a linker comprising a second multiple cloning site of frequently cutting enzymes that do not cleave pA0. Both plasmids have the same structure except for the orientation of the second multiple cloning site (FIG. 4.3).

The pA0 plasmid was digested with XhoI and ligated with an adaptor consisting of the annealed oligonucleotides P-A(1.1) and P-A(1.2). Plasmids of both possible orientations of the adaptor were isolated and designated paI and pA2.

The multiple cloning site of paI (corresponding to the oligonucleotide P-A(1.1)) and twenty bases of the 5'- and 3'-flanking regions of pA0 are shown in SEQ. ID. NO. 7. The insert starts at position 21 and ends at position 83. (The first "C" residue at the 5'-end corresponds to position number 2222, the last "C" residue at the 3'-end corresponds to position number 2324 of the plasmid pA).

The multiple cloning site of pA2 (corresponding to the oligonucleotide P-A(1.2)) and twenty bases of the 5' and 3'-ends of pA2 are shown in SEQ. ID. NO. 10. The insert starts at position 21 and ends at position 195. (The first "C" residue at the 5'-end corresponds to position number 2252, the last "G" residue at the 3'-end corresponds to position number 2466 of the plasmid pA2-S1).

Construction of plasmids pA1-S2 and pA2-S2: The plasmids pA1-S2 and pA2-S2 contain the strong synthetic promoter S2, a modified version of a strong late synthetic poxvirus promoter described by Davison & Moss, *J. Mol. Biol.* 210:771–784 (1989). These plasmids do not provide a translational start codon with the promoter and, therefore, are suited for insertion of complete open reading frames that include a start codon. The promoters have different orientations with respect to the vdTK master cloning site in these two plasmids.

Plasmids pA1-S2 and pA2-S2 are obtained by forced cloning of a second double-stranded promoter fragment into the HpaI and EcoRI sites of paI and pA2, respectively (FIG. 4.5, panel A). More particularly, plasmid pal is digested with the enzymes HpaI and EcoRI, and ligated with a synthetic linker sequence consisting of annealed oligonucleotides P-artP(5) and P-artP(6). The resulting plasmid is designated pA1-S2.

The synthetic promoter sequence of pA1-S2 (corresponding to the oligonucleotide P-artP(5) and twenty bases of the 5'- and 3'-flanking regions of pa1 are shown in SEQ. ID. NO. 11. The insert sequence starts at position 21 and ends at position 68. (The first "T" residue at the 5'-end corresponds to position number 2240, the last "A" residue at the 3'-end corresponds to position number 2327 of the plasmid pA1-S2).

Similarly, the plasmid pA2 is digested with the enzymes HpaI and EcoRI, and ligated with the annealed oligonucleotides P-artP(5) and P-artP(6) as for pA1-S2. The resulting plasmid is designated pA2-S2. The synthetic promoter sequence of pA2-S2 (corresponding to the oligonucleotide P-artP(6) and twenty bases of the 5'- and 3'-flanking regions of pA2 are shown in SEQ. ID. NO. 12. The insert starts at position 21 and ends at position 72. (The first "T" residue at the 5'-end corresponds to position number 2263, the last "A" residue at the 3'-end corresponds to position number 2354 of the plasmid pA2-S2).

After insertion of an open reading frame into any of the plasmids pA1-S1, pA2-S1, pA1-S2 or pA2-S2, the entire expression cassette can be excised and inserted by forced cloning into corresponding sites in the virus vector vdTK. The cassette can be inserted into the virus genome in either orientation depending on the cloning plasmid used.

Construction of plasmids comprising expression cassettes with a selective marker Besides plasmids (pN2gpt-S3A and pN2gpt-S4): designed for forced cloning, described hereinabove, two additional plasmids were constructed for transferring genes into one unique (NotI) site in a poxvirus vector with the help of the *E. coli* gpt selectable marker gene. They also provide two additional poxvirus promoters besides the S1 and S2 promoters described hereinabove.

The plasmid pN2gpt-S3A (FIG. 4.6) can be used to insert open reading frames lacking their own initiation codon. The genes to be transferred into vaccinia virus (the gpt marker and the open reading frame) can be excised either with NotI alone or with two enzymes, for example, NotI and SmaI (or RsrII or ApaI). The excised fragment is then inserted into the corresponding site(s) of the virus vector vdTK.

The plasmid pN2gpt-S4 (FIG. 4.6) can be used to insert complete open reading frames including an AUG translation start codon. The cassettes consisting of the gpt-marker gene and the open reading frame can be excised as described for pN2gpt-S3A. The promoters S3A and S4 are modified versions of strong poxvirus late promoters.

These plasmids were constructed by first making plasmids pN2-gpta and pN2-gptb which contain an *E. coli* gpt gene driven by the vaccinia virus P7.5 promoter, flanked by several unique restriction sites including NotI (FIG. 1.3). Insertion of the S3A or S4 promoter-fragment into the unique PstI and ClaI sites in pN2-gptb resulted in the plasmids pN2gpt-S3A and pN2gpt-S4.

Construction of plasmids pN2-gpta and pN2-gptb: See Example 1.

Construction of plasmid pN2gpt-S3A: The parental plasmid pN2-gptb was digested with PstI and ClaI and ligated with a synthetic linker sequence consisting of the oligonucleotides P-artP(7) and P-artP(8) (SEQ. ID. NO. 40). The resulting plasmid was designated pN2gpt-S3A.

The synthetic promoter sequence of pN2gpt-S3A (corresponding to the oligonucleotide P-artP(7)) and twenty bases of the 5'- and 3'-flanking regions of pN2-gptb are shown for pN2gpt-S3A in SEQ. ID. NO. 13. The inserted DNA sequence starts at position 21 and ends at position 107. (The first T-residue at the 5'-end corresponds to position number 3328, the last A-residue at the 3'-end to position number 3454 of the plasmid pN2gpt-S3A).

Construction of plasmid pN2gpt-S4: The plasmid pN2-gptb was digested with PstI and ClaI and ligated with an adaptor sequence consisting of the oligonucleotides P-artP(9) and P-artP(10) (SEQ. ID. NO. 41). The resulting plasmid was designated pN2gpt-S4.

The synthetic promoter sequence of pN2gpt-S4 (corresponding to the oligonucleotide P-artP(9)) and twenty bases of the 5'- and 3'-flanking regions of pN2-gptb are shown for pN2gpt-S4 in SEQ. ID. NO. 14. The inserted DNA sequence starts at position 21 and ends at position 114. (The first "T" residue at the 5'-end corresponds to base #3328, the last "A" residue at the 3'-end to position base #3461 of the plasmid pN2gpt-S4).

EXAMPLE 5

Expression of polypeptides in a vaccinia virus vector (vdTK) by direct molecular insertion of gene expression cassettes This example demonstrates the facility with which cloned genes can be inserted into a vaccinia virus vector (vdTK) of the present invention for rapid creation of poxvirus expression constructs using direct molecular insertion of gene expression cassettes described in Example 4. Here, use of the vdTK vector-cassette system to make constructs for expressing several particular model polypeptides is described, including human blood proteins (prothrombin and variants of plasminogen) and a human virus antigen (HIV gp160).

Construction of a modified vaccinia virus (vPT1) expressing human prothrombin: Human prothrombin (PT) serves as a model for foreign protein expression in a vaccinia virus vector of the present invention. A cDNA encoding prothrombin has been shown previously to be expressible by a conventionally constructed recombinant vaccinia virus, as disclosed in Patent Application PCT/EP91/00139 by Falkner et al. ("the Falkner application"), the entire disclosure of which is hereby incorporated herein by reference.

A modified prothrombin cDNA is excised as a 2.0 kb EcoRI fragment from the plasmid pTKgpt-PTHBb, and inserted into the single EcoRI site of the plasmid pA1-S1 (Example 4, FIG. 4.4) resulting in the plasmid pA1S1-PT (FIG. 5.1). In the expression cassette of this plasmid, the prothrombin cDNA is driven by the synthetic poxvirus promoter S1 which also provides a translation initiation codon.

The sequence of human prothrombin has been published: Degen S. J. F., MacGillivray R. T. A. & Davie, E. *Biochemistry* 22:2087–2097 (1983). This sequence is accessible in the EMBO Data Library under the Identifier (ID) HSTHR1. The sequence in ID HSTHR1 is not complete; it lacks the first 19 bp of the prothrombin coding region. The present inventors have sequenced the missing part of the cDNA in ID HSTHR1 and present this hereinbelow.

Due to the many modifications and base changes, the full sequence of the present human prothrombin cDNA clone including the S1 promoter and 20 bases of plasmid flanking sequences is shown in SEQ. ID. NO. 15.

By the engineering steps outlined in the Falkner application (PCT/EP-91/00139), the cDNA was modified as follows: two additional codons (bases #22–27) were introduced resulting in the incorporation of two new amino acids; the 3'-untranslated sequence was removed by introduction of an EcoRI site: bases #1963–1965 (#1920–1922 ID HSTHR1) were changed from TGG to GAA by site directed mutagenesis.

One base pair change was found in the present PT-cDNA, that results in a novel NcoI site: base #525 (#482 in ID HSTHR1) is changed from C to A. This is a silent mutation because the CCC codon (Pro) is changed to CCA (Pro) which results in a new NcoI site. (The first base of SEQ. ID. NO. 15 from pA1S1-PT corresponds to base #2394 and the last base to #4381 of the full sequence of plasmid pA1S1-PT).

For transfer into the vaccinia virus vector vdTK, the cassette is excised from the plasmid pA1S1-PT with NotI and RsrII endonucleases and isolated after separation on a low melting point agarose gel. The virus vector vdTK DNA is cleaved with NotI and RsrII, extracted with phenol and precipitated with ethanol. The small NotI-RsrII connecting fragment of the multiple cloning site of the vector DNA is lost during the ethanol precipitation step. The vaccinia vector arms are ligated with a twenty-fold molar excess of cassette. Packaging of ligated vaccinia virus DNA with fowlpox helper virus in chicken cells is described in Example 3. Packaged viruses from plaques produced by infection of in CV-1 cells are plaque purified again and small crude stocks are prepared. The virus isolates may be further analyzed by Southern blotting and expression analysis as described in the Falkner application. A viral isolate having the correct genomic structure for insertion of the prothrombin cDNA is designated vPT1. A similar recombinant vaccinia virus produced by marker rescue induced prothrombin expression in Vero cells at levels of activity of about 50–60 mU/ml of cell culture supernatant. See the Falkner application.

Construction of a vaccinia virus (vGPg1) expressing human glu-plasminogen: The native form of plasminogen (Pg) has an amino terminus starting with the amino acid glutamic acid (glu) and is therefore called glu-plasminogen (glu-Pg). A partially processed form of plasminogen that lacks the first 77 amino terminal amino acids (the activation peptide) is called lys-plasminogen (lysPg). The affinity of lys-Pg for its substrate fibrin is much higher than that of glu-Pg. In addition, recombinant lys-Pg is considerably more stable than glu-Pg in supernatants of cell cultures infected with a (conventional) vaccinia recombinant carrying the glu-Pg gene.

The complete human plasminogen cDNA (including its translational start and stop codons) was excised from a plasmid (phPlas-6) as a BalI-SmaI fragment. The sequence of human plasminogen has been published by Forsgren M, Raden B, Israelsson M, Larsson K & Heden L-O. FEBS Letters 213: 254–260 (1987) and is accessible in the EMBO Data Library (GenBank) under the Identifier (ID) HSPMGR. Therefore sequences of this plasmid have not been included in the instant Sequence Listing because this plasmid is not a unique source of the plasminogen DNA sequence. However, the coding region of the present plasminogen sequence differs from the published sequence in at least one nucleotide: the "A" residue at position #112 (ID HSPMGR) is a "G" residue in the instant DNA, resulting in an amino acid substitution (Lys→Glu).

The plasminogen cDNA was inserted into the HpaI site of the plasmid pN2gpt-S4 (Example 4, FIG. 4.6), which was selected for constructing a gene expression cassette with a selectable marker because the plasminogen cDNA contains two ApaI sites and one RsrII site and therefore does not allow the use of the expression cassettes designed for forced cloning. The resulting plasmid was designated pN2gpt-GPg (FIG. 5.2).

The joining region of the S4 promoter including the initiation codon of plasminogen (base #32 this listing; base #55 in ID HSPMGR) is shown for pN2gpt-GPg in SEQ. ID. NO. 17. The coding region of glu-plasminogen was omitted in the sequence listing. The sequence continues with the stop codon (base #35 this listing; base #2485 in ID HSPMGR) and 25 bases of the 3'-untranslated plasminogen sequence. This sequence is followed by 29 bases of the multiple cloning site of phPlas6 and by 20 bases of the multiple cloning site of plasmid pN2gpt-S4.

To transfer the glu-plasminogen gene cassette into a vaccinia virus genome, the NotI fragment of pN2gpt-GPg containing the two genes and their promoters (the P7.5 promoter controlling the gpt-selection marker, and the S4-promoter controlling the glu-plasminogen gene) is isolated from a low melting point agarose gel and purified. This cassette is ligated with arms of vaccinia virus vdTK DNA cut with NotI. Packaging and plaque purification are described in Example 3. A virus having the correct structure for the inserted plasminogen-gene cassette is designated vN2gpt-GPg. This virus is used for expression of plasminogen in CV-1 cells as described for an analogous vaccinia virus constructed by marker rescue techniques. Secreted glu-Pg in cell culture supernatants was detected at a level of about 1.5 $\mu g/10^6$ cells after 24 hours of infection with a conventionally constructed vaccinia virus under standard conditions for cultivation of vaccinia virus vectors for expression of foreign proteins in cell culture. The glu-plasminogen in the cell culture supernatant was detectable only in the presence of a protease inhibitor (50 $\mu$g/ml of aprotinin).

Construction of a vaccinia virus (vLPg1) expressing human lys-plasminogen: A sequence encoding lys-plasminogen was prepared by deletion of the 231 bp coding region for the first 77 amino acids (Glu1 to Lys77) of plasminogen from the complete plasminogen cDNA as shown in FIG. 5.3. This sequence was inserted into the gene expression cassette of a plasmid (pN2gpt-S4) having a selectable marker gene (*E. coli* gpt), resulting in the plasmid designated pN2gpt-LPg (FIG. 5.3).

In this plasmid, the pre-sequence (coding for the signal peptide that mediates secretion) is directly fused with the first nucleotide of lysine residue 78 in plasminogen. The novel signal peptide cleavage site created by the fusion is similar to many known signal cleavage sites. See, for instance, yon Heinje, *Eur. J. Biochem.* 133: 17–21 (1983).

In addition, an NcoI site was introduced at the site of the initiation codon of the Pg cDNA to facilitate cloning into the single NcoI site of the plasmid pN2gpt-S4 and to achieve the optimal context of the promoter and the Pg-coding region. To facilitate excision of Pg cDNA with NcoI, one of two internal NcoI sites (NcoI(2); FIG. 5.3) was deleted from the Pg cDNA, as follows.

The plasmid phPlas6 was transferred into *E. coli* strain NM522 and single-stranded DNA was prepared by superinfection with the helper phage M13K07. The first round of mutagenesis was done with two oligonucleotides, oNco1 and oNco2, using the single-stranded phPlas6 DNA as a template with a commercially available mutagenesis kit (Amersham, Inc.). The oligonucleotide Nco1 converts two A-residues upstream of the plasminogen start codon into two C-residues, resulting in an NcoI site around the start codon without changing the coding region of the plasminogen pre-sequence. The oligonucleotide oNco2 converts a T into a C residue within the internal NcoI site (NcoI(2)) of the Pg cDNA, producing a silent mutation that inactivates this NcoI site.

The coding region for amino acids 1–77 of plasminogen was deleted by second loop-out mutagenesis step using 42-base oligonucleotide oNco3. All mutations were confirmed by sequencing and restriction analysis.

The plasmid having the three mutations, phLplas, was linearized with SmaI and partially digested with NcoI. The 2.2 kb NcoI-SmaI fragment was isolated and inserted into plasmid pN2gpt-S4 that had been cut with NcoI and SmaI. The resulting plasmid was designated pN2gpt-LPg.

Due to the many modifications of the plasminogen cDNA in pN2gpt-LPg, the full sequence of the NcoI-SmaI fragment of pLplas including 20 bases of the S4 promoter and 20 bases of the downstream plasmid region of pN2gpt-S4 is shown in SEQ. ID. NO. 18. The plasminogen cDNA sequence was modified as follows: the former two A-residues at positions #19 and #20 (bases #53 and 54 in ID HSPMGR) were changed into two C-residues, resulting in an NcoI site; base #21 this listing (#55 in ID HSPMGR) is the A-residue of the plasminogen start codon; base #2220 (base #2485 in ID HSPMGR) is the T-residue of the stop codon; base #111 in ID HSPMGR (base #77 this listing) was joined with base #343 in ID HSPMGR (base #78 this listing) resulting in the deletion of the sequence coding for the "activation peptide"; the T-residue #926 (base #1191 in ID HSPMGR) was changed into a C residue (conservative exchange) resulting in the disappearance of an internal NcoI site.

To transfer the lys-plasminogen gene cassette into a vaccinia virus genome, the NotI fragment of pN2gpt-LPg containing the gene expression cassette comprised of two promoter-gene combinations (the P7.5 promoter-gpt gene and the S4 promoter-lys-plasminogen gene) is ligated with NotI cleaved vaccinia virus vdTK vector DNA and packaged as described in Example 7. An isolate having the proper structure for the inserted gene cassette, designated vN2gpt-LPg, is used for expression of lys-plasminogen in CV-1 cells under conditions used previously for a conventionally constructed recombinant under standard conditions for cultivation of vaccinia virus expression vectors for production of proteins in cell culture. Secreted lys-Pg in cell culture supernatants was detected at a level of about 1.0–2.0 $\mu g/10^6$ cells after 24 hours of infection with the conventional recombinant. The lys-plasminogen in the cell culture supernatant was stable without addition of a protease inhibitor.

Construction of a vaccinia virus (vgp160-1) for expressing human immunodeficiency virus glycoprotein 160 (HIV gp160): The complete open reading frame of HIV gp160 is obtained on a 2.5 kb EcoRV fragment containing excised from replicative form (RF) DNA of an M13 phage [mpPEenv; Fuerst et al., *Mol. Cell. Biol.* 7:2538–2544 (1987)]. This fragment is inserted into the plasmid pN2gpt-S4 as outlined in FIG. 5.4. In the resulting plasmid, pN2gpt-gp160, the gp160 gene is controlled by the synthetic vaccinia virus promoter S4.

The sequence of HIV gp160 has been published by Ratner, L. et al. *Nature* 313: 277–284 (1985). The sequence of clone BH8 is accessible in the EMBO Data Library (GenBank) under the Identifier (ID) HIVH3BHS. Therefore, the gp160 sequence is not included in SEQ. ID. NO. 19, but the joining region of the S4 promoter and an EcoRV HIV-gp160 fragment including the initiation codon of gp160 gene (base #28 this listing; base 226 in ID HIVH3BHS) is shown. The EcoRV HIV-gp160 fragment stems from the M13 phage (replicative form) mpPEenv described in Fuerst, T. R., Earl, P. & Moss, B. *Mol. Cell. Biol.* 7: 2538–2544 (1987). The sequence continues with the stop codon (base #31 this listing; base #2779 in ID HIVH3BH8) and one half of the downstream EcoRV site. This sequence is followed by 20 bases of the multiple cloning site of plasmid pN2gpt-S4. The first base (T) of this listing corresponds to base #3368, the last base (G), to #5973 in the sequence of pN2gpt-gp160.

To transfer the HIV gp160 gene-expression cassette into a vaccinia virus genome, the NotI fragment containing both gene-promoter combinations (the P7.5 promoter-gpt selection marker and the S4 promoter-gp160 gene) is ligated with NotI-cleaved DNA of the vaccinia virus vector vdTK and packaged as described in Example 7. An isolate having the correct structure of insertion of the cassette, designated vN2gpt-gp160, is used for expression of gp160 in African green monkey (Vero) cells under conditions used previously for a conventionally constructed recombinant. Barrett et al., *AIDS Research and Human Retroviruses* 6:159–171 (1989).

Construction of a vaccinia virus vector providing for screening for modified viruses carrying insertions by coinsertion of a lacZ gene: To demonstrate the screening for insertion by coinsertion of an *E. coli* lacZ gene in combination with the direct cloning approach, the plasmid pTZgpt-S3AlacZ provides a useful model construct (FIG. 5.5). The plasmid pTZ19R (Pharmacia, Inc.) was cut with PvuII, and the large 2.5 kb vector fragment was prepared and ligated with NotI linkers (Boehringer, Inc.). The resulting plasmid, pTZ-N, has a deletion of the multiple cloning site that is located within the sequences of the alpha complementation peptide in the pT219R plasmid. Therefore, possible recombination events between the lacZ gene to be inserted into pTZ-N and the sequences of the alpha complementation peptide are excluded.

To construct a gene expression cassette for direct molecular cloning, the 1.2 kb NotI fragment, containing the gpt-gene cassette and the S3A promoter, is excised from pN2gpt-S3A (Example 4) and inserted into pTZ-N resulting in the plasmid pTZgpt-S3A. The 3.0 kb EcoRI lacZ fragment (excised from plasmid pTKgpt-F1s$\beta$; Falkner & Moss, 1988) is inserted into the single EcoRI site of pTZgpt-S3A. The resulting plasmid designated pTZgpt-S3AlacZ.

The 4.4 kb NotI fragment of this plasmid, consisting of the two marker genes (*E. coli* gpt and lacZ), is ligated with NotI cleaved DNA of the virus vdTK (Example 4). The ligation and packaging conditions are described in Example 3. The estimated yield of modified viruses in the case of gpt-selection is described in Example 3.

The combination of lacZ and gpt-selection in a single cloning step offers no advantage because all gpt-positive plaques will contain the lacZ gene. However, for the construction of viruses having insertions in different sites, a second screening procedure is desirable. The marker of first choice is the gpt marker, but lacZ screening offers an alternative method for detection of inserts, for instance, when the target viral genome already contains a copy of a selectable marker such as the E. coli gpt gene.

For such screening, two ml of 1/10, 1/100 and 1/1000 dilutions of crude virus stocks prepared after packaging (see Example 3) is plated on 30 large (diameter of 8.5 cm) petri dishes (10 petri dishes per dilution). The blue plaque assay is done according to standard procedures. Chakrabarti, S., Brechling, K. & Moss, B. Mol. Cell. Biol. 5: 3403–3409 ( 1985).

EXAMPLE 6

Construction of a vaccinia virus vector (vs4) with a directional master cloning site under transcriptional control of a strong late vaccinia virus promoter The present example describes a vaccinia virus cloning vector (vS4) that is designed for direct molecular insertion of a complete open reading frame into a master cloning site that is functionally linked to a vaccinia virus promoter. Accordingly, use of this vector according to methods of the present invention enables insertion of genes directly into a poxvirus vector without separate construction of an insertion plasmid, as required in conventional construction of recombinant poxviruses by intracellular recombination. This vector also obviates the need for separate construction of a gene expression cassette for transfer into a vaccinia virus vector by direct molecular insertion, as described hereinabove.

The master cloning site of vector S4 is located in the genetically stable central region of the vaccinia virus genome and is comprised of several cleavage sites that are unique in the vector, thus permitting directional insertion. The S4 promoter immediately upstream of the master cloning site is a strong synthetic variant of a late vaccinia virus promoter. This expression vector is suitable for direct cloning and expression of large open reading frames which include a translation start codon, as illustrated here by a cDNA encoding a human blood protein, the von Willsbrand factor (vWF).

Construction of the vaccinia virus vector vS4: An adaptor containing the synthetic vaccinia virus promoter S4 is inserted into the vaccinia virus vector vdTK (Example 4, FIG. 4.1) at the unique NotI site (FIG. 6.1). Insertion of the selected adaptor oligonucleotides inactivates the upstream NotI site while the downstream NotI site remains functional as a unique cloning site.

More particularly, DNA (1 μg) of the vector vdTK (Example 4, FIG. 4.1) is cleaved with NotI and ligated with (0.5 μg) annealed oligonucleotides P-artP(11) (SEQ. ID. NO. 38 and P-artP(12) (SEQ. ID. NO. 39). The ligation mix is packaged and plaques are identified as described in Example 3. Plaques are subjected to PCR screening as described (Example 4, Identification of the virus vdTK by PCR screening). An isolate having the insert in the correct orientation is designated vS4.

Insertion of the yon Willebrand factor cDNA into vS4: Plasmid pvWF contains the complete yon Willebrand factor cDNA flanked by NotI sites. The sequence of human vWF has been published: Bonthron, D. et al., Nucl. Acids Res. 14: 7125–7128 1986). The sequence is accessible in the EMBO Data Library under the Identifier (ID) HSVWFR1. SEQ. ID. NO. 20 shows the junction in the virus genome of vvWF of the viral S4 promoter and the 5'-untranslated region of the present vWF cDNA in the plasmid pvWF up to the translational start codon (base #249 in this listing; base #100 in ID HSVWFR1). The coding region of vWF was omitted in the instant sequence listing. The sequence continues with the stop codon (base #252; base #8539 in ID HSVWFR1) and the 3'-untranslated sequence up to the NotI site (base #304) and twenty bases of overlap with the 3'-region of the viral genome of vvWF.

The vWF cDNA fragment is released with NotI, isolated and ligated with vS4 vector DNA that has been cleaved with NotI and treated with phosphatase, as illustrated in FIG. 6.2.

One μg of ligated DNA is packaged as described in Example 7. Plaques are picked and analyzed by PCR screening. The first primer for the PCR reaction is oligonucleotide odTK2 which is located about 300 bp upstream of the tk-gene; the reverse primer ovWF1 is located in the vWF gene about 50 bp downstream of the initiation codon. PCR amplification occurs only when the vWF insert is in the correct orientation relative to the S4 promoter in the vector. PCR-positive plaques are identified and analyzed further. Alternatively, if the yield of desired modified virus is low, on the order of 0.1 to 0.01%, then they may be identified by in situ plaque hybridization methods adapted from those known in the art. See, for instance, Villareal, L. P. & Berg, P. Science 196:183–185 (1977).

A virus clone having the cDNA insert by PCR or hybridization and further showing the expected restriction pattern with PvuII is designated vvWF. Such vectors may be tested for expression of von Willebrand factor as described for other human proteins in Example 5, modified as appropriate according to genetic engineering principles well known by one skilled in this art.

EXAMPLE 7

Heterologous packaging of orthopox (vaccinia) virus genomic DNA by an avipox (fowlpox) helper virus and simultaneous selection for modified virus in host cells of a species in which the helper virus cannot replicate Example 3 describes packaging of modified vaccinia virus DNA with fowlpox helper virus in avian cells and subsequent isolation of progeny virus plaques in mammalian (CV-1) cells in which the avipox helper virus cannot replicate. The present example illustrates packaging of vaccinia virus DNA by fowlpox directly in CV-1 cells, thereby permitting simultaneous packaging and host range selection for packaged virus. Besides eliminating helper virus from the initial stock of progeny, this procedure circumvents the tedious requirement for producing primary cultures of chicken embryo fibroblasts for each packaging experiment. Instead, continuous mammalian cell lines that are commonly used for vaccinia virus replication also can be used for packaging vaccinia virus with fowlpox helper virus.

It is known that fowlpox virus (FPV) replicates completely only in avian cells; no viable progeny virus is obtained from infected mammalian cells. The precise point in the life cycle of FPV at which replication is aborted in mammalian cells is not known. However, FPV is known to produce viral proteins in mammalian cells and even to induce protective immunity in mammals when used as a live vaccine. Taylor et al., *Vaccine* 6:497-503 (1988). Nevertheless, FPV has not been shown previously to have a capacity for packaging heterologous poxvirus genomic DNA, particularly directly engineered vaccinia virus DNA.

In an initial experiment, CV-1 cells ($5 \times 10^6$) were infected with one pfu/cell of fowlpox virus (strain HP1.441) and incubated for one hour. Subsequently, a calcium-phosphate precipitate (one ml containing one µg of vaccinia virus wildtype DNA) was transfected into the infected cells. After 15 min at room temperature, 10 ml of medium (DMEM, 10% fetal calf serum) were added. The cells were incubated for four hours, and the medium was changed. The cells were then incubated for six days, and a crude virus stock was prepared. The progeny virus were titered on CV-1 cells. Typical vaccinia plaques were visible after two days.

The dependence of packaging efficiency on the amount of genomic viral DNA was determined over a range of DNA amounts from 0.1 to 10 µg per $5 \times 10^6$ CV-1 cells. See FIG. 7.1. Amounts of DNA in excess of 1 µg (e.g., 10 µg) produced a coarse calcium-phosphate precipitate that reduced the efficiency of transfection in terms of pfu/µg of input DNA. FIG. 7.1.

The dependence of the packaged vaccinia virus yield on the incubation time for packaging was analyzed using a constant amount of vaccinia virus wildtype DNA (1 µg) and a constant amount of FPV helper virus (1 pfu/cell) under the conditions described above for the initial experiment in this example except that the medium added 15 minutes after transfection was changed after four hours, and the cells were then incubated for an additional 1 to 5 days before preparing a crude virus stock (total volume of 2 ml). Virus stock from control cells infected with FPV only and incubated for 5 days produced no visible plaques. This experiment was repeated three times and a typical outcome is shown in Table 1, below.

TABLE 1

Effect of incubation time on yield of vaccinia virus from DNA packaging by fowlpox helper virus in mammalian (CV-1) cells.

| Incubation Time (hours) | Titer (pfu/ml) |
| --- | --- |
| 24 | $1.0 \times 10^2$ |
| 48 | $4.6 \times 10^4$ |
| 72 | $5.0 \times 10^5$ |
| 96 | $5.6 \times 10^6$ |
| 120 | $2.1 \times 10^7$ |

The titer of packaged vaccinia virus, detected by plaque assay on mammalian (CV-1) cells, rose continually from about $10^2$ pfu/ml at 24 hours to about $2 \times 10^7$ after 120 hours. Incubation times in the range of 48 to 72 hours produced convenient levels of packaged vaccinia virus (between $10^4$ and $10^6$ pfu/ml) and, therefore, are suitable for routine packaging of vaccinia virus DNA by fowlpox virus in mammalian cells.

EXAMPLE 8

Homologous packaging of engineered vaccinia virus genomic DNA by a vaccinia virus host range mutant (vdhr) that is unable to replicate in a human cell line The present example illustrates construction and utilization of a helper poxvirus comprised of deletions that limit its host range, particularly the ability to replicate in certain human cell lines. Therefore, modified vaccinia virus free of helper virus can be prepared by packaging of vector DNA with this mutant helper virus and isolating clones of the engineered virus by infecting appropriate human cells.

This mutant helper virus is derived from host range mutants of vaccinia virus which are unable to replicate in a variety of human cells and which display altered cytopathic effects on many other cells that are permissive for infection by wildtype vaccinia virus. See, for example, Drillien et al., *Virology* 111: 488-499 (1981). In particular, the genome of this helper virus comprises mutations of two host range genes which together prevent it from replicating in human (MRC 5) cells in which only vaccinia virus genomes having at least one intact host range gene can replicate.

Construction of the host range mutant vaccinia virus vdhr: The genomic location and DNA sequence of one vaccinia virus gene required for replication in human cells has been described by Gillard et al., *Proc. Natl. Acad. Sci. USA* 83: 5573-5577 (1986). Recently, this gene has been designated K1L (Goebel et al., 1990). A second vaccinia virus host range gene has been mapped [Perkus et al., *J. Virology* 63: 3829-2836 (1990)]. This second gene (designated C7L according to Goebel et al., 1990) lies in a region encompassing parts of the HindIII C and HindIII N fragments. This region is deleted in the vaccinia virus WR6/2 strain [Moss et al., *J. Virol.* 40:387-395 (1981)]. Strain WR-6/2 therefore lacks the C7L host range gene.

The helper virus vdhr lacking both the K1L and C7L host range genes is constructed from the C7L-negative strain WR-6/2 by marker rescue with a modified EcoRI K fragment from which the K1L host range gene is deleted. See FIG. 8.1. This modified EcoRI K fragment comprises a selective marker gene (the *E. coli* gpt gene) to facilitate selection for modified WR-6/2 genomes comprising the modified EcoRI K fragment using intracellular marker rescue as described by Sam & Dumbell, 1981. A conditional lethal mutant which lacks the ability to grow on human cell lines has also been described by Perkus et al., 1989.

More particularly, the 5.2kb EcoRI K fragment of vaccinia virus wildtype DNA is subcloned into the plasmid pFP-tk1Si. The resulting plasmid is designated pFP-EcoK1. The vaccinia virus host range gene K1L (Gillard et al., 1986) is deleted and simultaneously a unique NotI site is introduced by loopout mutagenesis using the oligonucleotide P-hr(3) (SEQ. ID. NO. 42). The resulting plasmid is designated pEcoK-dhr.

The plasmid pFP-tk18i was constructed by modification of the plasmid pFP-tk-10.4 (see Falkner et al., European patent application number 89303887.7, publication EPA 0 338,807, Example 3 at 8, the entire disclosure of which is hereby incorporated herein by reference). Plasmid pFP-tk10.4 was digested with NcoI and ligated with an adaptor consisting of annealed nucleotides P-NcoI(1) and P-NcoI(2), resulting in the introduction of a multiple cloning site into the single NcoI site of the FPV tk-gene with the restriction endonuclease cleavage sites EcoRI, NotI and HindIII.

The sequence of vaccinia virus has been published by Goebel, S. J. et al., *Virology* 179: 247-266 (1990). It is accessible in the EMBO Data Library (GenBank) under the Accession Number M35027. The sequence of the vaccinia virus host range gene K1L has been published by Gillard. S. et al., *Proc. Natl. Acad. Sci. USA* 83: 5573–5577 (1986) and is accessible in the EMBO Data Library (GenBank) under the Identifier (ID) PXVACMHC. Therefore, the coding sequence of the K1L gene is not included in SEQ. ID. NO. 21. In pEcoK-dhr the K1L gene is deleted and replaced by a NotI site. The joining region between the PXVACMHC sequence and the NotI site insert is shown (bases #1–20 of this listing correspond to bases #72–91 in ID PXVACMHC). The coding region of K1L was deleted and replaced by a NotI site followed by two G residues (bases #21–30 in the sequence listing). The sequence continues with 20bp flanking region (bases #31–50 this listing; bases #944–963 in ID PXVACMHC).

In a further step pEcoK-dhr is linearized with NotI and ligated with a 1.1 kb P7.5-gpt gene cassette derived from plasmid pN2-gpta (Example 4) by NotI digestion. The resulting plasmid pdhr-gpt is used generate the helper virus vdhr.

The NotI cassette (comprising the P7.5 promoter-gpt-gene cassette) inserted into pEcoK-dhr and twenty bases of the 5′ and 3′ flanking regions are shown for pdhr-gpt in SEQ. ID. NO. 22. The flanking region (bases #1–20 this listing) correspond to bases #72–91 in ID PXVACMHC (see SEQ. ID. NO. 21 for pEcoK-dhr). The inserted DNA sequence starts at position 21 (the first "G" of a NotI site) and ends at position 1189 (the last "C" residue of a NotI site). The A-residue of the translational initiation codon of the gpt-gene corresponds to position #548. The T-residue of the translational stop codon of the gpt gene corresponds to position number #1004. The sequence continues with 20 bases of flanking region (bases #1192–1209 this listing; bases #944–961 in ID PXVACMHC). The two "G" residues #1190 and 1191 in this listing, correspond to position 29 and 30 of pEcoK-dhr.

To transfer the Eco K fragment into vaccinia virus, the plasmid is transfected into primary chicken embryo fibroblasts cells infected with the vaccinia virus deletion mutant WR-6/2. Modified viruses are selected as gpt-positive (using mycophenolic acid). A gpt-positive is plaque-purified three times in CEF cells and designated vdhr.

Characterization of the vdhr helper virus: The structure of gpt-positive vaccinia virus vdhr is analyzed by Southern blotting and host range tests. The vdhr virus is capable of forming plaques on chicken embryo fibroblasts and two monkey cell lines (BSC40 and Vero) but is defective for replication in the human cell line MRC-5.

Packaging of engineered vaccinia virus DNA using the host range mutant vdhr as a helper virus: A construct for expression of a cDNA encoding human prothrombin demonstrates the utility of this approach. The product from a ligation mixture described in Example 5, FIG. 5.1, is transfected into chicken embryo fibroblasts infected with vdhr as a helper virus. After 2 days the cells are harvested and a crude virus stock is prepared. Packaged virus is assayed for plaque formation on human (MRC 5) cells in which the desired vaccinia virus replicates but the mutant vdhr helper virus does not.

After three days the cells are stained with neutral red and plaques are selected for further analysis by Southern blotting. Modified vaccinia virus clones having the desired structure are identified. Viruses which have undergone recombination with the highly homologous helper virus are also expected.

What is claimed is:

1. A method for producing a modified chordopoxvirus by direct molecular cloning of a modified chordopox viral genome, wherein said method comprises the steps of (I) modifying under extracellular conditions a purified DNA molecule comprising a first genome of a first chordopoxvirus to produce a modified DNA molecule comprising said modified viral genome;

(II) infecting a first host cell with a second chordopoxvirus that is not from the same genus as said first chordopoxvirus, said second chordopoxvirus comprising a second viral genome which is expressed to package said modified first viral genome into infectious virions;

(III) introducing said modified DNA molecule into said first host cell, which packages said modified viral genome into infectious virions; and (IV) recovering from said first host cell infectious virions comprised of said modified viral genome.

2. The method according to claim 1 wherein the step of modifying said DNA molecule under extracellular conditions comprises a step of cleaving said DNA molecule with a sequence-specific endonuclease.

3. The method according to claim 1 wherein the step of modifying said DNA molecule comprises a step of inserting a first DNA sequence into said first genome.

4. The method according to claim 3 wherein said first DNA sequence is inserted into said first genome at a cleavage site for a sequence-specific endonuclease.

5. The method according to claim 4 wherein said cleavage site for a sequence-specific endonuclease is a unique site in said first genome.

6. The method according to claim 5, wherein the step of modifying said DNA molecule comprises a step of using a phosphatase to remove a phosphate moiety from an end of a DNA segment that is produced by cleaving said DNA molecule with a sequence-specific endonuclease at said unique site.

7. The method according to claim 6, wherein said first genome is a vaccinia virus genome and said unique site is a cleavage site for the bacterial restriction endonuclease NotI or for the bacterial restriction endonuclease SmaI.

8. The method according to claim 7, wherein said first genome comprises a second DNA sequence not naturally occurring in a chordopoxvirus genome and said second DNA sequence is comprised of said unique site.

9. The method according to claim 8, wherein said first genome is a fowlpox virus genome comprising a sequence of an *Escherichia coli* β-galactosidase gene and said unique site is a cleavage site for the bacterial restriction endonuclease NotI.

10. The method according to claim 3, wherein said first DNA sequence is inserted into said first genome between a first cleavage site for a first sequence-specific endonuclease and a second cleavage site for a second sequence-specific endonuclease.

11. The method according to claim 10, wherein each of said first and said second cleavage sites is unique in said first genome.

12. The method according to claim 3, wherein at least a portion of said first DNA sequence which is inserted into said first genome is under transcriptional control of a promoter.

13. The method according to claim 12, wherein said promoter is located in said first DNA sequence that is inserted into said first genome.

14. The method according to claim 12, wherein said promoter is located in said modified viral genome upstream of said first DNA sequence that is inserted into said first genome.

15. The method according to claim 12, wherein said promoter is utilized by an RNA polymerase encoded by said modified viral genome.

16. The method according to claim 15, wherein said promoter is suitable for initiation of transcription by an RNA polymerase of said chordopoxvirus.

17. The method according to claim 16, wherein said promoter comprises a modification of a naturally occurring promoter of said chordopoxvirus.

18. The method according to claim 1 wherein the step of modifying said DNA molecule comprises a step of deleting a DNA sequence from said first genome.

19. The method according to claim 1 wherein the step of modifying said DNA molecule comprises a step of substituting a DNA sequence of said first genome.

20. The method according to claim 1, wherein the step of introducing said modified DNA molecule into said first host cell is carried out about one hour after the step of infecting said first host cell with said second chordopoxvirus.

21. The method according to claim 1, wherein expression of said second genome in said first host cell does not produce infectious virions comprised of said second genome.

22. The method according to claim 1, wherein said modified viral genome is a modified vaccinia virus genome, said second genome is a fowlpox virus genome, and said first host cell is a mammalian cell.

23. The method according to claim 1, wherein the step of recovering infectious virions comprised of said modified viral genome comprises a step of infecting a second host cell with infectious virions produced by said first host cell under conditions such that expression of said second genome in said second host cell does not produce infectious virions comprised of said second genome.

24. The method according to claim 23, wherein said modified viral genome is a modified vaccinia virus genome, said second genome is a fowlpox virus genome, and said second host cell is a mammalian cell.

25. The method according to claim 23, wherein said modified viral genome comprises a selective marker gene, said second genome lacks said selective marker gene, and the step of infecting said second host cell is carried out under conditions that select for a genome expressing said selective marker gene.

26. The method according to claim 25, wherein expression of said selective marker gene in said second host cell confers on said second host cell resistance to a cytotoxic drug which is present during infection of said second host cell at a level sufficient to select for a genome expressing said selective marker gene.

* * * * *

UNITED STATES PATENT AND TRADEMARK OFFICE
CERTIFICATE OF CORRECTION

Page 1 of 3

PATENT NO. : 5,445,953
DATED : August 29, 1995
INVENTOR(S) : Friedrich DORNER et al.

It is certified that error appears in the above-indentified patent and that said Letters Patent is hereby corrected as shown below:

Column 1, line 34, delete "C"; column 2, line 34, "vital" should read --viral--; column 6, line 53, after "comprises" insert line 54; column 8, line 24, "pA1S1PT" should read --PA1S1-PT--; column 9, line 39, delete "A" and insert --λ--; column 10, line 13, delete "A" and insert --λ--; line 58, delete "HP1,441" and insert --HP1.441--; column 13, line 28, after "viruses" insert line 29; column 19, line 3, after "for" insert line 4; column 27, line 11, "pal" should read --pA1--; column 28, line 68, "J. P." should read --J.-P.--; column 29, line 56, "KSDS" should read --K-SDS--; column 30, line 36, "1:5" should read --1: 5--; line 38, "2:5" should read

UNITED STATES PATENT AND TRADEMARK OFFICE
CERTIFICATE OF CORRECTION

PATENT NO. : 5,445,953
DATED : August 29, 1995
INVENTOR(S) : Friedrich DORNER et al.

It is certified that error appears in the above-indentified patent and that said Letters Patent is hereby corrected as shown below:

--2: 5--; line 39, "3:5" should read --3: 5--; line 43, "Stratagens" should read --Stratagene--; line 52, "Stratagens" should read --Stratagene--; line 58, "pN2gptb" should read --PN2-gptb--; column 33, line 58, "the" should read --them--; column 39, lines 55-57 should read as a subheading; line 58, "vital" should read --viral--; column 43, line 22, delete "and viral DNA"; column 52, lines 27, 28, 40, 41 and 68 "pal" should read --pA1--; line 48, "pA" should read --pA1--; column 53, lines 2 and 8, "pal" should read --pA1--; line 34, after "marker" insert --(pN2gpt-S3A and pN2gpt-S4):--; column 58, lines 12 and 16, "HIVH3BHS" should read --HIVH3BH8--; column 59, line 60, after "38" insert --)--; lines 67 and 68, "yon" should read --von--; column 62, line 47, "pFP-tk1Si" should read --pFP-tk18i--.

UNITED STATES PATENT AND TRADEMARK OFFICE
CERTIFICATE OF CORRECTION

PATENT NO. : 5,445,953
DATED : August 29, 1995
INVENTOR(S) : Friedrich DORNER et al.

It is certified that error appears in the above-indentified patent and that said Letters Patent is hereby corrected as shown below:

Column 53, line 35, "(pN2gpt-S3A and pN2gpt-S4): should be deleted.

Signed and Sealed this

Eleventh Day of June, 1996

*Attest:*

BRUCE LEHMAN

*Attesting Officer*     *Commissioner of Patents and Trademarks*